United States Patent
Klinguer-Hamour et al.

(10) Patent No.: US 11,340,233 B2
(45) Date of Patent: May 24, 2022

(54) UNIVERSAL METHOD TO CAPTURE AND ANALYZE ADCS FOR CHARACTERIZATION OF DRUG DISTRIBUTION AND THE DRUG-TO-ANTIBODY RATIO IN BIOLOGICAL SAMPLES

(71) Applicant: PIERRE FABRE MEDICAMENT, Boulogne-Billancourt (FR)

(72) Inventors: Christine Klinguer-Hamour, Groisy (FR); Marie-Claire Janin-Bussat, Saint-Julien-en-Genevois (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 162 days.

(21) Appl. No.: 16/082,708

(22) PCT Filed: Mar. 7, 2017

(86) PCT No.: PCT/EP2017/055362
§ 371 (c)(1),
(2) Date: Sep. 6, 2018

(87) PCT Pub. No.: WO2017/153432
PCT Pub. Date: Sep. 14, 2017

(65) Prior Publication Data
US 2019/0079099 A1    Mar. 14, 2019

Related U.S. Application Data

(60) Provisional application No. 62/304,549, filed on Mar. 7, 2016.

(51) Int. Cl.
*G01N 33/68* (2006.01)
*G01N 33/543* (2006.01)
*G01N 33/577* (2006.01)
*G01N 33/94* (2006.01)

(52) U.S. Cl.
CPC ... *G01N 33/6848* (2013.01); *G01N 33/54326* (2013.01); *G01N 33/577* (2013.01); *G01N 33/6854* (2013.01); *G01N 33/94* (2013.01)

(58) Field of Classification Search
CPC .. G01N 33/6848; G01N 33/94; G01N 33/577; G01N 33/6854; G01N 33/54326
See application file for complete search history.

(56) References Cited

U.S. PATENT DOCUMENTS

| | | |
|---|---|---|
| 4,970,198 A | 11/1990 | Lee et al. |
| 5,079,233 A | 1/1992 | Lee |
| 5,530,101 A | 6/1996 | Queen et al. |
| 5,585,089 A | 12/1996 | Queen et al. |
| 5,606,040 A | 2/1997 | McGahren et al. |
| 5,639,641 A | 6/1997 | Pedersen et al. |
| 5,693,761 A | 12/1997 | Queen et al. |
| 5,693,762 A | 12/1997 | Queen et al. |
| 5,739,116 A | 4/1998 | Hamann et al. |
| 5,767,285 A | 6/1998 | Hamann et al. |
| 5,773,001 A | 6/1998 | Hamann et al. |
| 5,792,632 A | 8/1998 | Dujon et al. |
| 5,830,729 A | 11/1998 | Jaisser et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 6,238,924 B1 | 5/2001 | Dujon et al. |
| 8,541,178 B2 * | 9/2013 | Kaur ................. G01N 33/6854 435/7.1 |
| 10,633,448 B2 * | 4/2020 | Rilatt ................. C07K 16/2863 |
| 2017/0112943 A1 * | 4/2017 | Goetsch ............. A61K 47/6849 |

FOREIGN PATENT DOCUMENTS

| | | |
|---|---|---|
| EP | 0682040 A1 | 11/1995 |
| EP | 0451216 B1 | 1/1996 |
| EP | 0939127 A2 | 9/1999 |
| WO | WO 92/11018 A1 | 7/1992 |
| WO | WO 03/025183 A2 | 3/2003 |
| WO | WO 2004/067753 A2 | 8/2004 |
| WO | WO 2009/054985 A1 | 4/2009 |
| WO | WO 2015/162291 A1 | 10/2015 |

OTHER PUBLICATIONS

Chames et al. Therapeutic antibodies: successes, limitations and hopes for future. British J. Pharmacology 2009, vol. 157, pp. 220-233. (Year: 2009).*
"Immunoprecipitation Kit Dynabeads® Protein G," Life Technologies, Jan. 2012, Catalog No. 10007D, 2 pages total.
"CaptureSelect™ Biotin Anti-IgG-Fc (Hu) Conjugate," Product Information Sheet, retrieved from URL:https://tools.thermofisher. com/content/sfs/manuals/MAN0010061.pdf, Oct. 19, 2015, 4 pages.
Alley et al., "Contribution of Linker Stability to the Activities of Anticancer Immunoconjugates," Bioconjugate Chem., vol. 19, No. 3, 2008 (published online Mar. 4, 2008), pp. 759-765.
Alley et al., "The Pharmacologic Basis for Antibody-Auristatin Conjugate Activity," The Journal of Pharmacology and Experimental Therapeutics, vol. 330, No. 3, 2009, pp. 932-938.
Bebbington et al., "High-Level Expression of a Recombinant Antibody From Myeloma Cells Using a Glutamine Synthetase Gene as an Amplifiable Selectable Marker," Bio/Technology, vol. 10, Feb. 1992, pp. 169-175.

(Continued)

*Primary Examiner* — Shafiqul Haq

(74) *Attorney, Agent, or Firm* — Birch, Stewart, Kolasch & Birch, LLP

(57) ABSTRACT

The present invention relates to a new method for capturing and analysing antibody-drug conjugates (ADCs) in biological samples, such as e.g., serum. Methods for analysing the structure of an antibody-drug conjugate (ADC) in a biological sample and methods for assessing the stability of an ADC are also provided.

6 Claims, 11 Drawing Sheets

Figure 1A:
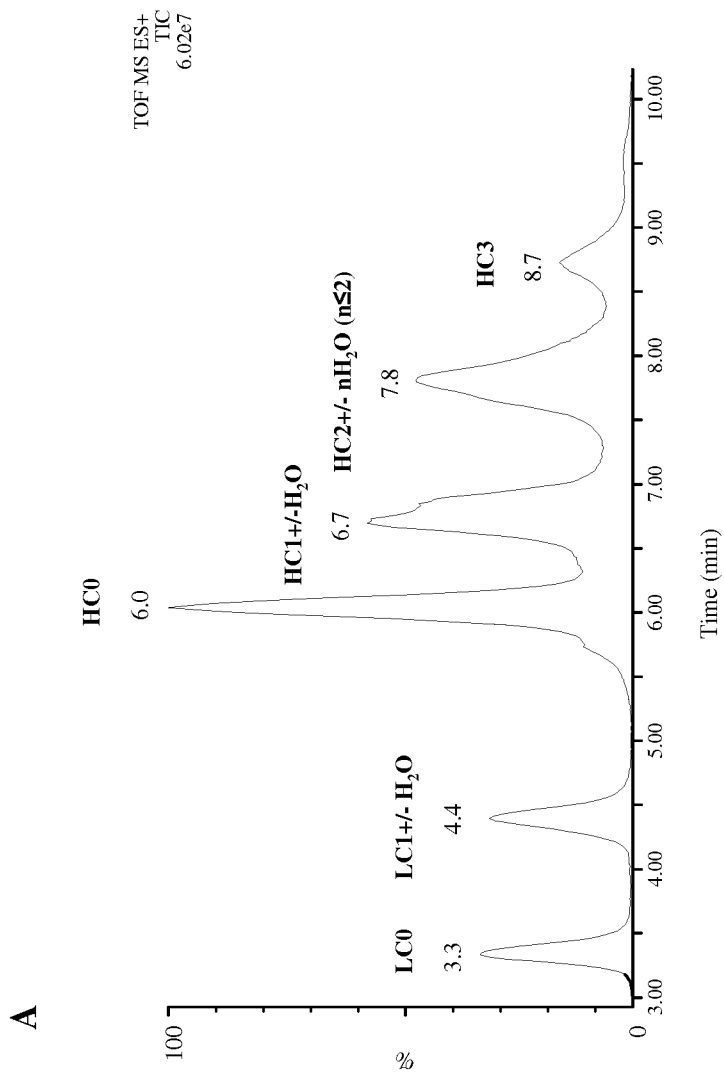

Specification includes a Sequence Listing.

(56) References Cited

OTHER PUBLICATIONS

Beck et al., "Antibody-Drug Conjugates," mAbs, vol. 6, No. 1, 2014 (published online Dec. 5, 2013), pp. 15-17 (4 pages total).
Beck et al., "Characterization of Therapeutic Antibodies and Related Products," Analytical Chemistry, vol. 85, Nov. 7, 2012, pp. 715-736.
Beck et al., "Cutting-Edge Mass Spectrometry Methods for the Multi-Level Structural Characterization of Antibody-Drug Conjugates," Expert Review of Proteomics, vol. 13, No. 2, 2016 (published online Jan. 22, 2016), pp. 157-183 (28 pages total).
Beck et al., "The Next Generation of Antibody-Drug Conjugates Comes of Age," Discovery Medicine, vol. 10, No. 53, Oct. 2010, pp. 329-339.
Birch et al., "Antibody Production," Advanced Drug Delivery Reviews, vol. 58, 2006 (published online May 22, 2006), pp. 671-685.
Birdsall et al., "A Sensitive Multidimensional Method for the Detection, Characterization, and Quantification of Trace Free Drug Species in Antibody-Drug Conjugate Samples Using Mass Spectral Detection," MABS, vol. 8, No. 2, 2016, pp. 306-317.
Burton et al., "Immunoglobulin G: Functional Sites," Molecular Immunology, vol. 22, No. 3, 1985, pp. 161-206.
Chari et al., "Antibody-Drug Conjugates: An Emerging Concept in Cancer Therapy," Angew. Chem. Int. Ed., vol. 53, 2014, pp. 3796-3827.
Cockett et al., "High Level Expression of Tissue Inhibitor of Metalloproteinases in Chinese Hamster Ovary Cells Using Glutamine Synthetase Gene Amplification," Bio/Technology, vol. 8, Jul. 1990, pp. 662-667.
Crouse et al., "Expression and Amplification of Engineered Mouse Dihydrofolate Reductase Minigenes," Molecular and Cellular Biology, vol. 3, No. 2, Feb. 1983, pp. 257-266.
Debaene et al., "Innovative Native MS Methodologies for Antibody Drug Conjugate Characterization: High Resolution Native MS and IM-MS for Average DAR and DAR Distribution Assessment," Analytical Chemistry, vol. 86, Sep. 30, 2014, pp. 10674-10683.
Deisenhofer, "Crystallographic Refinement and Atomic Models of a Human Fc Fragment and Its Complex with Fragment B of Protein A from *Staphylococcus aureus* at 2.9- and 2.8-Å Resolution," Biochemistry, vol. 20, No. 9, Apr. 28, 1981, pp. 2361-2370.
Foecking et al., "Powerful and Versatile Enhancer-Promoter Unit for Mammalian Expression Vectors," Gene, vol. 45, 1986, pp. 101-105.
Fontaine et al., "Long-Term Stabilization of Maleimide-Thiol Conjugates," Bioconjugates Chemistry, vol. 26, Dec. 12, 2014, pp. 145-152.
Fraker et al., "Protein and Cell Membrane Iodinations with a Sparingly Soluble Chloroamide, 1,3,4,6-Tetrachloro-3a,6a-Diphenylglycoluril," Biochemical and Biophysical Research Communications, vol. 80, No. 4, Feb. 28, 1978, pp. 849-857.
Hengel et al., "Measurement of in Vivo Drug Load Distribution of Cysteine-Linked Antibody-Drug Conjugates Using Microscale Liquid Chromatography Mass Spectrometry," Analytical Chemistry, vol. 86, Feb. 27, 2014, pp. 3420-3425.
International Search Report (Form PCT/ISA/210) for International Application No. PCT/EP2017/055362, dated Jun. 1, 2017.
Janin-Bussat et al., "Characterization of Antibody Drug Conjugate Positional Isomers at Cysteine Residues by Peptide Mapping LC-MS Analysis," Journal of Chromatography B, vol. 981-982, 2015 (published online Dec. 24, 2014) pp. 9-13.
Jones et al., "Replacing the Complementarity-Determining Regions in a Human Anitbody with Those From a Mouse," Nature, vol. 321, May 29, 1986, pp. 522-525.
Kaur et al., Bioanalytical Assay Strategies for the Development of Antibody-Drug Conjugate Biotherapeutics, Bioanalysis, vol. 5, No. 2, 2013, pp. 201-226.
Klinguer-Hamour et al., "World Antibody-Drug Conjugate Summit," mAbs, vol. 6, Issue 1, Oct. 15-16, 2013, pp. 18-29.
Köhler et al., "Continuous Cultures of Fused Cells Secreting Antibody of Predefined Specificity," Nature, vol. 256, Aug. 7, 1975, pp. 495-497.
Ledford, "Toxic Antibodies Blitz Tumours," Nature, vol. 476, Aug. 25, 2011, pp. 380-381.
Lowy et al., "Isolation of Transforming DNA: Cloning the Hamster aprt Gene," Cell, vol. 22, Dec. 1980, pp. 817-823.
Lyon et al., "Conjugation of Anticancer Drugs Through Endogenous Monoclonal Antibody Cysteine Residues," Methods in Enzymology, vol. 502, 2012, pp. 123-138.
Lyon et al., "Self-Hydrolyzing Maleimides Improve the Stability and Pharmacological Properties of Antibody-Drug Conjugates," Nature Biotechnology, vol. 32, No. 10, Oct. 2014 (published online Sep. 7, 2014), pp. 1059-1062 (7 pages total).
Marcoux et al., "Native Mass Spectrometry and Ion Mobility Characterization of Trastuzumab Emtansine, a Lysine-Linked Antibody Drug Conjugate," Protein Science, vol. 24, 2015 (published online Feb. 18, 2015), pp. 1210-1223.
Moehle et al., "Targeted Gene Addition into a Specified Location in the Human Genome Using Designed Zinc Finger Nucleases," PNAS, vol. 104, No. 9, Feb. 27, 2007, pp. 6090, 3055-3060 (with correction as published in vol. 104, No. 14, Apr. 3, 2007).
Mountain et al., "Engineering Antibodies for Therapy," Biotechnology and Genetic Engineering Reviews, vol. 10, Dec. 1992, pp. 1-142.
Mulligan et al., "Selection for Animal Cells that Express the *Escherichia coli* Gene Coding for Xanthine-Guanine Phosphoribosyltransferase," Proc. Natl. Acad. Sci. USA, vol. 78, No. 4, Apr. 1981, pp. 2072-2076.
Pacholarz et al., "Use of a Charge Reducing Agent to Enable Intact Mass Analysis of Cysteine-Linked Antibody-Drug-Conjugates by Native Mass Spectrometry," EuPA Open Proteomics, vol. 11, 2016 (published online Mar. 4, 2016), pp. 23-27.
Phillips et al., "Targeting HER2-Positive Breast Cancer with Trastuzumab-DM1, an Antibody-Cytotoxic Drug Conjugate," Cancer Res, vol. 68, No. 22, Nov. 15, 2008, pp. 9280-9290 (12 pages total).
Reik et al., "Enhanced Protein Production by Engineered Zinc Finger Proteins," Biotechnology and Bioengineering, vol. 97, No. 5, Aug. 1, 2007, pp. 1180-1189.
Riechmann et al., "Reshaping Human Antibodies for Therapy," Nature, vol. 332, Mar. 24, 1988, pp. 323-327.
Saber et al., "An FDA Oncology Analysis of Antibody-Drug Conjugates," Regulatory Toxicology and Pharmacology, vol. 71, 2015 (published online Feb. 7, 2015), pp. 444-452.
Sanderson et al., "Antibody-Conjugated Drug Assay for Protease-Cleavable Antibody-Drug Conjugates," Bioanalysis, vol. 8, No. 1, 2016, pp. 55-63.
Santerre et al., "Expression of Prokaryotic Genes for Hygromycin B and G418 Resistance as Dominant-Selection Markers in Mouse L Cells," Gene, vol. 30, 1984, pp. 147-156.
Shen et al., "Conjugation Site Modulates the in vivo Stability and Therapeutic Activity of Antibody-Drug Conjugates," Nature Biotechnology, vol. 30, No. 2, Feb. 2012 (published online Jan. 22, 2012), pp. 184-188 (8 pages total).
Singer et al., "Optimal Humanization of 1B4, an Anti-CD18 Murine Monoclonal Antibody, is Achieved by Correct Choice of Human V-Region Framework Sequences," The Journal of Immunology, vol. 150, No. 7, Apr. 1, 1993, pp. 2844-2857.
Szybalska et al., "Genetics of Human Cell Lines, IV. DNA-Mediated Heritable Transformation of a Biochemical Trait," Proc. Natl. Acad. Sci., vol. 48, Oct. 15, 1962, pp. 2026-2034.
Tibbitts et al., "Key Factors Influencing ADME Properties of Therapeutic Proteins: A Need for ADME Characterization in Drug Discovery and Development," mAbs, vol. 8, No. 2, 2016, pp. 229-245.
Tumey et al., "Mild Method for Succinimide Hydrolysis on ADCs: Impact on ADC Potency, Stability, Exposure, and Efficacy," Bioconjugate Chemistry, vol. 25, Sep. 12, 2014, pp. 1871-1880.
Valliere-Douglass et al., "Native Intact Mass Determination of Antibodies Conjugated with Monomethyl Auristatin E and F at Interchain Cysteine Residues," Analytical Chemistry, vol. 84, Feb. 15, 2012, pp. 2843-2849.

(56) References Cited

OTHER PUBLICATIONS

Verhoeyen et al., "Engineering of Antibodies," BioEssays, vol. 8, No. 2, Feb./Mar. 1988, pp. 74-78.

Verhoeyen et al., "Reshaping Human Antibodies: Grafting an Antilysozyme Activity," Science, vol. 239, Mar. 25, 1988, pp. 1534-1536.

Wagner-Rousset et al., "Antibody-Drug Conjugate Model Fast Characterization by LC-MS Following IdeS Proteolytic Digestion," mAbs, vol. 6, Issue 1, 2013, pp. 173-184.

Wakankar et al., "Analytical Methods for Physicochemical Characterization of Antibody Drug Conjugates," mAbs, vol. 3, Issue 2, 2011, pp. 161-172.

Wang et al., "Generation and Characterization of a Unique Reagent that Recognizes a Panel of Recombinant Human Monoclonal Antibody Therapeutics in the Presence of Endogenous Human IgG," mAbs, vol. 5, Issue 4, 2013, pp. 540-554.

Wiggins et al., "Characterization of Cysteine-Linked Conjugation Profiles of Immunoglobulin G1 and Immunoglobulin G2 Antibody-Drug Conjugates," Journal of Pharmaceutical Sciences, vol. 104, 2015 (published online Jan. 28, 2015), pp. 1362-1372.

Wigler et al., "Transfer of Purified Herpes Virus Thymidine Kinase Gene to Cultured Mouse Cells," Cell, vol. 11, May 1977, pp. 223-232.

Wigler et al., "Transformation of Mammalian Cells with an Amplifiable Dominant-Acting Gene," Proc. Natl. Acad. Sci. USA, vol. 77, No. 6, Jun. 1980. pp. 3567-3570.

Wiseman et al., "Ibritumomab tiuxetan radioimmunotherapy for patients with relapsed or refractory non-Hodgkin lymphoma and mild thrombocytopenia: a phase II multicenter trial," Blood, vol. 99, No. 12, Jun. 15, 2002, pp. 4336-4342 (8 pages total).

Wiseman et al., "Phase I/II $^{90}$Y-Zevalin (yttrium-90 ibritumomab tiuxetan, IDEC-Y2B8) radioimmunotherapy dosimetry results in relapsed or refractory non-Hodgkin's lymphoma," European Journal of Nuclear Medicine, vol. 27, No. 7, Jul. 2000, pp. 766-777 (13 pages total).

Witzig et al., "Randomized Controlled Trial of Yttrium-90-Labeled Ibritumomab Tiuxetan Radioimmunotherapy Versus Rituximab Immunotherapy for Patients With Relapsed or Refractory Low-Grade, Follicular . . . ," Journal Clinical Oncology, vol. 20, No. 10, May 15, 2002, pp. 2453-2463.

Witzig et al., "Treatment with Ibritumomab Tiuxetan Radioimmunotherapy in Patients with Rituximab-Refractory Follicular Non-Hodgkin's Lymphoma," Journal of Clinical Oncology, vol. 20, No. 15, Aug. 1, 2002, pp. 3262-3269.

Wright et al., "Optimizing Chromatography and High Resolution Time-of-Flight Mass Spectrometry for Antibody-Drug Conjugate DAR Characterization," retrieved from URL:https://sciex.com/Documents/posters/asms2014_271_Pharma_Wright_Simons.pdf, Jun. 11, 2014, 1 page.

Wu et al., "Delivery Systems for Gene Therapy," Biotherapy, vol. 3, 1991, pp. 87-95.

Xu et al., "Characterization of the Drug-to-Antibody Ratio Distribution for Antibody-Drug Conjugates in Plasma/Serum," Bioanalysis, vol. 5, No. 9, 2013, pp. 1057-1071.

* cited by examiner

UNIVERSAL METHOD TO CAPTURE AND ANALYZE ADCS FOR CHARACTERIZATION OF DRUG DISTRIBUTION AND THE DRUG-TO-ANTIBODY RATIO IN BIOLOGICAL SAMPLES

CROSS REFERENCE TO RELATED APPLICATIONS

This application is the National Phase of PCT International Application No. PCT/EP2017/055362, filed on Mar. 7, 2017, which claims priority under 35 U.S.C. 119(e) to U.S. Provisional Application No. 62/304,549, filed on Mar. 7, 2016, all of which are hereby expressly incorporated by reference into the present application.

INTRODUCTION

The present invention relates to a new method for capturing and analysing antibody-drug conjugates (ADCs) in biological samples, such as e.g., serum.

In oncology, there are multiple mechanisms by which mAbs (monoclonal antibodies) can exert their therapeutic efficacy. However, most often, their activity is not sufficient to produce a lasting benefit. Hence several strategies have been employed to enhance their activity particularly by combining them with drugs as chemotherapeutic agents. As an efficient alternative to combination protocols, immunotoxins become a novel therapeutic option for treating cancer [Beck A. et al. Discov. Med. (2010). 10, 329-339; Alley S. C. et al. J. Pharmacol. Exp. Ther. (2009). 330, 932-938]. Antibody-drug conjugates (ADCs) represent one approach where the ability to harness mAbs specificity and target the delivery of a cytotoxic agent to the tumour may significantly enhance both mAbs and drug activities. Ideally the mAb will specifically bind to an antigen with substantial expression on tumour cells but limited expression on normal cells.

ADCs are becoming a major class of oncology therapeutics. Two ADCs, brentuximab vedotin (Adcetris®) and ado-trastuzumab emtansine (Kadcyla®) are approved both by the US Food and Drug Administration and the European Medicine Agency[1], and near 60 are currently being investigated in clinical trials[2]. They combine monoclonal antibody specificity for over-expressed tumor antigens and the high cytoxicity of small molecular drugs (SMDs) and can therefore selectively kill tumor cells while minimizing toxicity to normal cells. Nevertheless, the premature deconjugation of ADCs in the circulation may trigger off target toxicity in patients.

The released free drug level must be low in circulation for an extended period of time as well as the de-conjugation rate to ensure an acceptable therapeutic window. As a result, the assessment of the stability of the linker between payload and mAb in the systemic circulation is of paramount importance before entering in clinical trial.

The primary sites used for protein-directed conjugation are the amino groups of lysine residues (near one third of ADC in clinical trials) or the sulfhydryl groups of the inter-chain cysteine residues (near two thirds)[3]. Conjugates like brentuximab vedotin are formed through partial reduction of the antibody interchain disulfide bonds (up to 4 in the case of chimeric, humanized and human IgG1 and 4; up to 6 in the case of IgG2), followed by alkylation with a preformed drug-linker maleimide activated species. They result in conjugates with a distribution of drug loading from 0, 2, 4, 6 or 8 drugs incorporated per antibody (IgG1 or IgG4) or from 0, 2, 4, 6, 8, 10, or 12 for IgG2[4].

Lysine conjugates are most commonly assembled via the formation of amide bonds between the epsilon amino group of endogenous lysine residues and activated esters[5].

Most of the maytansinoid- or auristatin-based immunoconjugates that are currently FDA approved or in clinical trials show an average drug to antibody ratio (DAR) of ~4 drugs/mAb[6]. Conjugation of drugs to mAbs increases the structural complexity of the resulting molecule[2], which triggers the need for improved characterization methods[7] for analysis of average DAR, drug distribution[8], size and charge variants, unconjugated drug[9], peptide mapping[10, 11], biophysical properties[12] as well as for bioanalysis[13].

Multiple-level structural assessment methods and protocols are needed to gain structural insights of highly complex biopharmaceuticals such as ADCs[14]. As a result, ADCs need to be characterized by orthogonal methods at different levels, those of the intact conjugated antibody, subunits thereof, peptides, and free small molecular drugs (the top, middle, bottom, and drug-linker levels, respectively)[2]. These assays can separately evaluate the ADC and may give different information due to assay measurement differences, heterogeneous nature of ADCs and biotransformations that occur in vivo[15].

Shawna Mae Hengel et al reported recently measurement of in vivo drug load distribution of cysteine-linked antibody-drug conjugates using microscale liquid chromatography mass spectrometry[16]. The cysteine-linked ADCs were affinity purified with custom affinity resins and analysed using native LCMS to determine the drug load distribution in vivo (top level). Russell J Sanderson et al reported an antibody-conjugated drug assay for (vcMMAE, cleavable linker) ADCs[17]. A stable isotope-labelled internal standard, protein A affinity capture and solid-phase cleavage of MMAE using papain was used prior to LC-MS/MS analysis (SMDs level).

Thus there is still a need for a reliable and simple method for assessing the stability of ADCs in biological samples.

DESCRIPTION

The present inventors have now devised a new method for assessing the in vivo stability of ADCs. This new universal alternative method is based on the binding of ADCs (e.g., by an immunocapture method) by reagents targeting the Fc (fragment crystallisable) domain of the antibody. This binding is preferentially followed by analysis by LC-MS. Even more preferably, the method of the invention comprises a reduction step of the captured ADCs, thus leading to LC-MS analysis of reduced hinge cysteine-linked ADCs, resulting in subunits (middle level) suitable for both cleavable and non-cleavable linkers.

The inventors have shown that this new method can be used for assessing easily and reliably the stability of ADCs in biological samples. Remarkably, they have shown that the in vivo behaviour of an ADCC can be accurately monitored with the present method. Moreover, the in vivo behaviour of an ADCC can be accurately mimicked in vitro, by adding said ADC to an unrelated biological sample. Furthermore, they demonstrated that this workflow can be applied to both ADCs with cleavable and non-cleavable linkers. Last but not least, the results obtained by the inventors in cynomolgus serum using immunoprecipitation and LC-MS analysis were cross validated using an ELISA orthogonal method. As the ligand used for immunoprecipitation targets the Fc part of mAb, this protocol can be applied to analyse the stability of any ADC in biological sample without the need to prepare specific molecular tools.

The invention thus relates to a method for analysing the structure of an ADC present in a biological sample of a subject, said method comprising the steps of:
a) contacting said biological sample with a reagent binding specifically the Fc domain of the antibody moiety of the ADC;
b) isolating the ADC molecules bound by said reagent; and
c) analysing the structure of the ADC thus isolated.

In a first embodiment, the subject is a subject to whom said ADC was previously administered. In another embodiment, the biological sample of the subject was previously added with said ADC. Such an embodiment may be useful for assessing the stability of an ADC in e.g., plasma, without actually administering said ADC to the subject.

As used herein, the term "subject" is intended to include living organisms in general, and specifically includes mammals, such as rabbits, dogs, cats, mice, rats, monkey, transgenic species thereof, and preferably humans. A human subject may be a "patient", i.e., a human subject to whom said ADC was injected in order to cure a disease or a condition such as e.g., a hyperproliferative disorder, including cancer.

The term "antibody-drug-conjugate" or "ADC" as used herein, refers to a binding protein, such as an antibody or antigen binding fragment thereof, chemically linked to one or more chemical drug(s) (also referred to herein as agent(s)) that may optionally be therapeutic and/or cytotoxic agents. In a preferred embodiment, an ADC includes an antibody, a chemical drug, i.e., a cytotoxic and/or therapeutic drug, and a linker that enables attachment or conjugation of the drug to the antibody. An ADC typically has anywhere from 1 to 8 drugs conjugated to the antibody, including drug loaded species of 2, 4, 6, or 8. Such compounds are also known in the art as "immunoconjugate" or "immuno-conjugate."

In a preferred embodiment, analysing the structure of the ADC in step c) involves determining the number of drug molecules bound per antibody moiety. This parameter is commonly used in the art and is designated "DAR" (for "drug-antibody ratio"). The behaviour of the DAR in a biological sample is representative of the stability of the ADC. A decrease in the DAR between two samples from the same subject indicates a dissociation of at least some ADC molecules.

An "antibody" is an immunoglobulin (Ig) molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding fragment") or single chain thereof, fusion proteins comprising an antibody, and any other modified configuration of the immunoglobulin molecule that comprises an antigen recognition site including, for example without limitation, scFv, single domain antibodies {e.g., shark and camelid antibodies), maxibodies, minibodies, intrabodies, diabodies, triabodies, tetrabodies, v-NAR and bis-scFv. As used herein, the term "antibody" encompasses both full-length antibodies and their antigen-binding fragments, as well as any derivative thereof. Preferably, the antibody according to the invention, or its derived compounds or antigen-binding fragments, is a monoclonal antibody.

A "monoclonal antibody", as used herein, means an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen. Since these antibodies are directed against a single epitope, they are highly specific.

An "epitope" is the site on the antigen to which an antibody binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

The generation of the antibody reactive with a specific antigen can be realized by any method known by the man skilled in the art, such as for example, fusion of a myeloma cell with spleen cells from immunized mice or other species compatible with the selected myeloma cells [Kohler Et Milstein, 1975, Nature, 256:495-497]. The immunized animals could include transgenic mice with human immunoglobulin loci which then directly produce human antibodies. Alternatively, an antibody can be generated by recombinant methods such as selection of libraries of recombinant antibodies in phage or similar vectors. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes.

A typical IgG antibody is composed of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

There are three heavy-chain CDRs and 3 light-chain CDRs. The term "CDR" or "CDRs" is used here in order to indicate, according to the case, one of these regions or several, or even the whole, of these regions which contain the majority of the amino acid residues responsible for the binding by affinity of the antibody for the antigen or the epitope which it recognizes.

As used herein, "VH" or "VH" refers to the variable region of an immunoglobulin heavy chain of an antibody, including the heavy chain of an Fv, scFv, dsFv, Fab, Fab', or F(ab')2 fragment. Reference to "VL" or "VL" refers to the variable region of the immunoglobulin light chain of an antibody, including the light chain of an Fv, scFv, dsFv, Fab, Fab', or F(ab')2 fragment.

Antibody constant domains are not involved directly in binding an antibody to an antigen, but exhibit various effector functions. The heavy chain constant regions that correspond to the different classes of immunoglobulins are called α, δ, ε, γ, and μ, respectively. Depending on the amino acid sequence of the constant region of their heavy chains, antibodies or immunoglobulins can be assigned to different classes, i.e., IgA, IgD, IgE, IgG, and IgM, and several of these may be further divided into subclasses (isotypes), e.g., IgG1, IgG2, IgG3, and IgG4; IgA1 and IgA2 (see, W. E. Paul, ed., 1993, Fundamental Immunology, Raven Press, New York, N.Y.).

Papain digestion of antibodies produces two identical antigen binding fragments, called Fab fragments, each with a single antigen binding site, and a residual "Fc" fragment. The crystal structure of the human IgG Fc domain has been determined (Deisenhofer, Biochemistry, 20, 2361-2370, 1981). As used in the specification and claims, "immunoglobulin Fc domain or Fc" means the carboxyl-terminal portion of the immunoglobulin heavy chain constant region. A "native sequence Fc domain", as used herein, comprises an amino acid sequence identical to the amino acid sequence of a Fc domain found in nature. Native sequence human Fc domains include a native sequence human IgG1 Fc domain (non-A and A allotypes); native sequence human IgG2 Fc domain; native sequence human IgG3 Fc domain; and native sequence human IgG4 Fc domain as well as naturally occurring variants thereof.

Although the boundaries of the Fc domain of an immunoglobulin heavy chain might vary, the human IgG heavy chain Fc domain is usually defined to stretch from an amino acid residue at position Cys226 or Pro230 in the hinge region, to the carboxyl-terminus thereof containing the CH2 and CH3 domain of the heavy chain. Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody.

The term "hinge region" is generally defined as stretching from Glu216 to Pro230 of human IgG1 (Burton, Mol Immunol, 22: 161-206, 1985). Hinge regions of other IgG isotypes may be aligned with the IgG1 sequence by placing the first and last cysteine residues forming inter-heavy chain S—S bonds in the same positions. The "CH2 domain" of a human IgG Fc portion (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule.

It has been speculated that the carbohydrate may provide a substitute for the domain-domain pairing and help stabilize the CH2 domain (Burton, *Mol Immunol,* 22: 161-206, 1985).

The "CH3 domain" comprises the stretch of residues C-terminal to a CH2 domain in an Fc portion (i.e., from about amino acid residue 341 to about amino acid residue 447 of an IgG).

The Fc domains are central in determining the biological functions of the immunoglobulin and these biological functions are termed "effector functions". These Fc domain-mediated activities are mediated via immunological effector cells, such as killer cells, natural killer cells, and activated macrophages, or various complement components. These effector functions involve activation of receptors on the surface of said effector cells, through the binding of the Fc domain of an antibody to the said receptor or to complement component(s). The antibody-dependent cellular cytotoxicity (ADCC) and complement-dependent cytotoxicity (CDC) activities involve the binding of the Fc domain to Fc-receptors such as FcγRI, FcγRII, FcγRIII of the effector cells or complement components such as C1q. Of the various human immunoglobulin classes, human IgG11 and IgG3 mediate ADCC more effectively than IgG2 and IgG4.

The antibodies of the invention also comprise chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. It will be appreciated that in this case, the Fc domain of the chimeric antibody is of human origin. Refer to Verhoeyn et al. (BioEssays, 8:74, 1988) for methods for preparing chimeric antibodies.

In addition, the invention also relates to humanized antibodies arising from the murine antibodies described above. "Humanized antibody" refers herein to an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988). The Fc domain of a humanized antibody will be of human origin, as in chimeric antibodies.

The humanized antibodies of the invention or fragments of same can be prepared by techniques known to a person skilled in the art (such as, for example, those described in the documents Singer et al., J. Immun., 150:2844-2857, 1992; Mountain et al., Biotechnol. Genet. Eng. Rev., 10:1-142, 1992; and Bebbington et al., Bio/Technology, 10: 169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566

647 or U.S. Pat. Nos. 5,530,101, 6,180,370, 5,585,089 and 5,693,761. U.S. Pat. Nos. 5,639,641 or 6,054,297, 5,886,152 and 5,877,293 can also be cited.

According to the invention, a variety of expression systems may be used to express the IgG antibody of the invention. In one aspect, such expression systems represent vehicles by which the coding sequences of interest may be produced and subsequently purified, but also represent cells which may, when transiently transfected with the appropriate nucleotide coding sequences, express an IgG antibody of the invention in situ.

The invention provides vectors comprising the polynucleotides of the invention. In one embodiment, the vector contains a polynucleotide encoding a heavy chain of an IgG antibody of the invention, i.e. an antibody which carries a mutation in the Fc domain. In another embodiment, said polynucleotide encodes the light chain of an IgG antibody of the invention. The invention also provides vectors comprising polynucleotide molecules encoding fusion proteins, modified antibodies, antibody fragments, and probes thereof.

In order to express the heavy and/or light chain of the an IgG antibody of the invention, the polynucleotides encoding said heavy and/or light chains are inserted into expression vectors such that the genes are operatively linked to transcriptional and translational sequences.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the heavy and/or light chains of the antibodies of the invention. The skilled man will realize that the polynucleotides encoding the heavy and the light chains can be cloned into different vectors or in the same vector. In a preferred embodiment, said polynucleotides are cloned into two vectors.

Polynucleotides of the invention and vectors comprising these molecules can be used for the transformation of a suitable host cell. The term "host cell", as used herein, is intended to refer to a cell into which a recombinant expression vector has been introduced in order to express the IgG antibody of the invention. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

Transformation can be performed by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

The host cell may be co-transfected with two or more expression vectors, including the vector expressing the protein of the invention. For example, a host cell can be transfected with a first vector encoding an IgG antibody, as described above, and a second vector encoding a glycosyltransferase polypeptide. Alternatively, the host cell can be transformed with a first vector encoding an antibody of the invention, a second vector encoding a glycosyltransferase, as described above, and a third vector encoding another glycosyltransferase. Mammalian cells are commonly used for the expression of a recombinant therapeutic immunoglobulins, especially for the expression of whole recombinant IgG antibodies. For example, mammalian cells such as HEK293 or CHO cells, in conjunction with a vector, containing the expression signal such as one carrying the major intermediate early gene promoter element from human cytomegalovirus, are an effective system for expressing the IgG antibody of the invention (Foecking et al., 1986, *Gene* 45:101; Cockett et al., 1990, *Bio/Technology* 8: 2).

In addition, a host cell is chosen which modulates the expression of the inserted sequences, or modifies and processes the gene product in the specific fashion desired. Such modifications (e.g., glycosylation) and processing of protein products may be important for the function of the protein. Different host cells have features and specific mechanisms for the post-translational processing and modification of proteins and gene products. Appropriate cell lines or host systems are chosen to ensure the correct modification and processing of the expressed antibody of interest. Hence, eukaryotic host cells which possess the cellular machinery for proper processing of the primary transcript, glycosylation of the gene product may be used. Such mammalian host cells include, but are not limited to, CHO, COS, HEK293, NS/0, BHK, Y2/0, 3T3 or myeloma cells (all these cell lines are available from public depositories such as the Collection Nationale des Cultures de Microorganismes, Paris, France, or the American Type Culture Collection, Manassas, Va., U.S.A.).

For long-term, high-yield production of recombinant proteins, stable expression is preferred. In one embodiment of the invention, cell lines which stably express the antibody may be engineered. Rather than using expression vectors which contain viral origins of replication, host cells are transformed with DNA under the control of the appropriate expression regulatory elements, including promoters, enhancers, transcription terminators, polyadenylation sites, and other appropriate sequences known to the person skilled in art, and a selectable marker. Following the introduction of the foreign DNA, engineered cells may be allowed to grow for one to two days in an enriched media, and then are moved to a selective media. The selectable marker on the recombinant plasmid confers resistance to the selection and allows cells to stably integrate the plasmid into a chromosome and be expanded into a cell line. Other methods for constructing stable cell lines are known in the art. In particular, methods for site-specific integration have been developed. According to these methods, the transformed DNA under the control of the appropriate expression regulatory elements, including promoters, enhancers, transcription terminators, polyadenylation sites, and other appropriate sequences is integrated in the host cell genome at a specific target site which has previously been cleaved (Moele et al., Proc. Natl. Acad. Sci. U.S.A., 104(9): 3055-3060; U.S. Pat. Nos. 5,792,632; 5,830,729; 6,238,924; WO 2009/054985; WO 03/025183; WO 2004/067753).

A number of selection systems may be used according to the invention, including but not limited to the Herpes simplex virus thymidine kinase (Wigler et al., Cell 11:223, 1977), hypoxanthine-guanine phosphoribosyltransferase (Szybalska et al., Proc Natl Acad Sci USA 48: 202, 1992), glutamate synthase selection in the presence of methionine sulfoximide (Adv Drug Del Rev, 58: 671, 2006, and website or literature of Lonza Group Ltd.) and adenine phosphoribosyltransferase (Lowy et al., Cell 22: 817, 1980) genes in tk, hgprt or aprt cells, respectively. Also, antimetabolite resistance can be used as the basis of selection for the following genes: dhfr, which confers resistance to methotrexate (Wigler et al., Proc Natl Acad Sci USA 77: 357, 1980); gpt, which confers resistance to mycophenolic acid (Mulligan et al., Proc Natl Acad Sci USA 78: 2072, 1981); neo, which confers resistance to the aminoglycoside, G-418 (Wu et al., Biotherapy 3: 87, 1991); and hygro, which confers resistance to hygromycin (Santerre et al., Gene 30: 147, 1984). Methods known in the art of recombinant DNA technology may be routinely applied to select the desired recombinant clone, and such methods are described, for example, in Ausubel et al., eds., Current Protocols in Molecular Biology, John Wiley Et Sons (1993). The expression levels of an antibody can be increased by vector amplification. When a marker in the vector system expressing an antibody is amplifiable, an increase in the level of inhibitor present in the culture will increase the number of copies of the marker gene. Since the amplified region is associated with the gene encoding the IgG antibody of the invention, production of said antibody will also increase (Crouse et al., *Mol Cell Biol* 3: 257, 1983). Alternative methods of expressing the gene of the invention exist and are known to the person of skills in the art. For example, a modified zinc finger protein can be engineered that is capable of binding the expression regulatory elements upstream of the gene of the invention; expression of the said engineered zinc finger protein (ZFN) in the host cell of the invention leads to increases in protein production (see e.g. Reik et al., *Biotechnol. Bioeng.*, 97(5): 1180-1189, 2006). Moreover, ZFN can stimulate the integration of a DNA into a predetermined genomic location, resulting in high-efficiency site-specific gene addition (Moehle et al, *Proc Natl Acad Sci USA*, 104: 3055, 2007).

The antibody of the invention may be prepared by growing a culture of the transformed host cells under culture conditions necessary to express the desired antibody. The resulting expressed antibody may then be purified from the culture medium or cell extracts. Soluble forms of the antibody of the invention can be recovered from the culture supernatant. It may then be purified by any method known in the art for purification of an immunoglobulin molecule, for example, by chromatography (e.g., ion exchange, affinity, particularly by Protein A affinity for Fc, and so on), centrifugation, differential solubility or by any other standard technique for the purification of proteins. Suitable methods of purification will be apparent to a person of ordinary skills in the art.

The invention relates to an ADC comprising the antigen binding protein as described in the present specification conjugated to a cytotoxic agent.

By "cytotoxic agent" or "cytotoxic", it is intended an agent which, when administered to a subject, treats or prevents the development of cell proliferation, preferably the development of cancer in the subject's body, by inhibiting or preventing a cellular function and/or causing cell death.

Many cytotoxic agents have been isolated or synthesized and make it possible to inhibit the cells proliferation, or to destroy or reduce, if not definitively, at least significantly the tumour cells. However, the toxic activity of these agents is not limited to tumour cells, and the non-tumour cells are also effected and can be destroyed. More particularly, side effects are observed on rapidly renewing cells, such as haematopoietic cells or cells of the epithelium, in particular of the mucous membranes. By way of illustration, the cells of the gastrointestinal tract are largely effected by the use of such cytotoxic agents.

One of the aims of the present invention is also to be able to provide a cytotoxic agent which makes it possible to limit the side effects on normal cells while at the same time conserving a high cytotoxicity on tumour cells.

More particularly, the cytotoxic agent may preferably consist of, without limitation, a drug (i.e "antibody-drug conjugate"), a toxin (i.e. "immunotoxin" or "antibody-toxin conjugate"), a radioisotope (i.e. "radioimmunoconjugate" or "antibody-radioisotope conjugate"), etc.

In a first preferred embodiment of the invention, the immunoconjugate consists of a binding protein linked to at least a drug or a medicament. Such an immunoconjugate is referred as an antibody-drug conjugate (or "ADC") when the binding protein is an antibody, or an antigen binding fragment thereof.

In a first embodiment, such drugs can be described regarding their mode of action. As non-limitative examples, it can be mentioned alkylating agents such as nitrogen mustard, alkyl-sulfonates, nitrosourea, oxazophorins, aziridines or imine-ethylenes, anti-metabolites, anti-tumour antibiotics, mitotic inhibitors, chromatin function inhibitors, anti-angiogenesis agents, anti-oestrogens, anti-androgens, chelating agents, iron absorption stimulant, cyclooxygenase inhibitors, phosphodiesterase inhibitors, DNA inhibitors, DNA synthesis inhibitors, apoptosis stimulants, thymidylate inhibitors, T cell inhibitors, interferon agonists, ribonucleoside triphosphate reductase inhibitors, aromatase inhibitors, oestrogen receptor antagonists, tyrosine kinase inhibitors, cell cycle inhibitors, taxane, tubulin inhibitors, angiogenesis inhibitors, macrophage stimulants, neurokinin receptor antagonists, cannabinoid receptor agonists, dopamine receptor agonists, granulocytes stimulating factor agonists, erythropoietin receptor agonists, somatostatin receptor agonists, LHRH agonists, calcium sensitizers, VEGF receptor antagonists, interleukin receptor antagonists, osteoclast inhibitors, radical formation stimulants, endothelin receptor antagonists, *vinca* alkaloid, anti-hormone or immunomodulators or any other new drug that fulfils the activity criteria of a cytotoxic or a toxin.

Such drugs are, for example, cited in the VIDAL 2010, on the page devoted to the compounds attached to the cancerology and haematology column "Cytotoxics", these cytotoxic compounds cited with reference to this document are cited here as preferred cytotoxic agents.

More particularly, without limitation, the following drugs are preferred according to the invention: mechlorethamine, chlorambucol, melphalen, chlorydrate, pipobromen, prednimustin, disodic-phosphate, estramustine, cyclophosphamide, altretamine, trofosfamide, sulfofosfamide, ifosfamide, thiotepa, triethylenamine, altetramine, carmustine, streptozocin, fotemustin, lomustine, busulfan, treosulfan, improsulfan, dacarbazine, cis-platinum, oxaliplatin, lobaplatin, heptaplatin, miriplatin hydrate, carboplatin, methotrexate, pemetrexed, 5-fluoruracil, floxuridine, 5-fluorodeoxyuridine, capecitabine, cytarabine, fludarabine, cytosine arabinoside, 6-mercaptopurine (6-MP), nelarabine, 6-thioguanine (6-TG), chlorodesoxyadenosine, 5-azacytidine, gemcitabine, cladribine, deoxycoformycin, tegafur, pentostatin, doxorubicin, daunorubicin, idarubicin, valrubicin, mitoxantrone, dactinomycin, mithramycin, plicamycin, mitomycin C, bleomycin, procarbazine, paclitaxel, docetaxel, vinblastine, vincristine, vindesine, vinorelbine, topotecan, irinotecan, etoposide, valrubicin, amrubicin hydrochloride, pirarubicin, elliptinium acetate, zorubicin, epirubicin, idarubicin and teniposide, razoxin, marimastat, batimastat, prinomastat, tanomastat, ilomastat, CGS-27023A, halofuginon, COL-3, neovastat, thalidomide, CDC 501, DMXAA, L-651582, squalamine, endostatin, SU5416, SU6668, interferon-alpha, EMD121974, interleukin-12, IM862, angiostatin, tamoxifen, toremifene, raloxifene, droloxifene, iodoxyfene, anastrozole, letrozole, exemestane, flutamide, nilutamide, spirironolactone, cyproterone acetate, finasteride, cimitidine, bortezomid, velcade, bicalutamide, cyproterone, flutamide, fulvestran, exemestane, dasatinib, erlotinib, gefitinib, imatinib, lapatinib, nilotinib, sorafenib, sunitinib, retinoid, rexinoid, methoxsalene, methylaminolevulinate, aldesleukine, OCT-43, denileukin diftitox, interleukin-2, tasonermine, lentinan, sizofilan, roquinimex, pidotimod, pegademase, thymopentine, poly I:C, procodazol, Tic BCG, *Corynebacterium parvum*, NOV-002, ukrain, levamisole, 131I-chTNT, H-101, celmoleukin, interferon alfa2a, interferon alfa2b, interferon gamma1a, interleukin-2, mobenakin, Rexin-G, teceleukin, aclarubicin, actinomycin, arglabin, asparaginase, carzinophilin, chromomycin, daunomycin, leucovorin, masoprocol, neocarzinostatin, peplomycin, sarkomycin, solamargine, trabectedin, streptozocin, testosterone, kunecatechins, sinecatechins, alitretinoin, belotecan hydrocholoride, calusterone, dromostanolone, elliptinium acetate, ethinyl estradiol, etoposide, fluoxymesterone, formestane, fosfetrol, goserelin acetate, hexyl aminolevulinate, histrelin, hydroxyprogesterone, ixabepilone, leuprolide, medroxyprogesterone acetate, megesterol acetate, methylprednisolone, methyltestosterone, miltefosine, mitobronitol, nadrolone phenylpropionate, norethindrone acetate, prednisolone, prednisone, temsirrolimus, testolactone, triamconolone, triptorelin, vapreotide acetate, zinostatin stimalamer, amsacrine, arsenic trioxide, bisantrene hydrochloride, chlorambucil, chlortrianisene, cis-diamminedichloroplatinium, cyclophosphamide, diethylstilbestrol, hexamethylmelamine, hydroxyurea, lenalidomide, lonidamine, mechlorethanamine, mitotane, nedaplatin, nimustine hydrochloride, pamidronate, pipobroman, porfimer sodium, ranimustine, razoxane, semustine, sobuzoxane, mesylate, triethylenemelamine, zoledronic acid, camostat mesylate, fadrozole HCl, nafoxidine, aminoglutethimide, carmofur, clofarabine, cytosine arabinoside, decitabine, doxifluridine, enocitabine, fludarabne phosphate, fluorouracil, ftorafur, uracil mustard, abarelix, bexarotene, raltiterxed, tamibarotene, temozolomide, vorinostat, megastrol, clodronate disodium, levamisole, ferumoxytol, iron isomaltoside, celecoxib, ibudilast, bendamustine, altretamine, mitolactol, temsirolimus, pralatrexate, TS-1, decitabine, bicalutamide, flutamide, letrozole, clodronate disodium, degarelix, toremifene citrate, histamine dihydrochloride, DW-166HC, nitracrine, decitabine, irinoteacn hydrochloride, amsacrine, romidepsin, tretinoin, cabazitaxel, vandetanib, lenalidomide, ibandronic acid, miltefosine, vitespen, mifamurtide, nadroparin, granisetron, ondansetron, tropisetron, alizapride, ramosetron, dolasetron mesilate, fosaprepitant dimeglumine, nabilone, aprepitant, dronabinol, TY-10721, lisuride hydrogen maleate, epiceram, defibrotide, dabigatran etexilate, filgrastim, pegfilgrastim, reditux, epoetin, molgramostim, oprelvekin, sipuleucel-T, M-Vax, acetyl L-carnitine, donepezil hydrochloride, 5-aminolevulinic acid, methyl aminolevulinate, cetrorelix acetate, icodextrin, leuprorelin, metbylphenidate, octreotide, amlexanox, plerixafor, menatetrenone, anethole dithiolethione, doxercalciferol, cinacalcet hydrochloride, alefacept, romiplostim, thymoglobulin, thymalfasin, ubenimex, imiquimod, everolimus, sirolimus, H-101, lasofoxifene, trilostane, incadronate, gangliosides, pegaptanib octasodium, vertoporfin, minodronic acid, zoledronic acid, gallium nitrate, alendronate sodium, etidronate disodium, disodium pamidronate, dutasteride, sodium stibogluconate, armodafinil, dexrazoxane, amifostine, WF-10, temoporfin, darbepoetin alfa, ancestim, sargramostim, palifermin, R-744, nepidermin, oprelvekin, denileukin diftitox, crisantaspase, buserelin, deslorelin, lanreotide, octreotide, pilocarpine, bosentan, calicheamicin, maytansinoids and ciclonicate.

For more detail, the person skilled in the art could refer to the manual edited by the "Association Française des Enseignants de Chimie Thérapeutique" and entitled "Traité de chimie thérapeutique, vol. 6, Médicaments antitumoraux et perspectives dans le traitement des cancers, edition TEC & DOC, 2003".

In a second preferred embodiment of the invention, the immunoconjugate consists of a binding protein linked to at least a radioisotope. Such an immunoconjugate is referred as an antibody-radioisotope conjugate (or "ARC") when the binding protein is an antibody, or an antigen binding fragment thereof.

For selective destruction of the tumour, the antibody may comprise a highly radioactive atom. A variety of radioactive isotopes are available for the production of ARC such as, without limitation, $At^{211}$, $C^{13}$, $N^{15}$, $O^{17}$, $Fl^{19}$, $I^{123}$, $I^{131}$, $I^{125}$, In$^{111}$, Y$^{90}$, Re$^{186}$, Re$^{188}$, Sm$^{153}$, tc$^{99}$m, Bi$^{212}$, P$^{32}$, Pb$^{212}$, radioactive isotopes of Lu, gadolinium, manganese or iron.

Any methods or processes known by the person skilled in the art can be used to incorporate such radioisotope in the ARC (see, for example "Monoclonal Antibodies in Immunoscintigraphy", Chatal, CRC Press 1989). As non-limitative examples, tc$^{99}$m or I$^{123}$, Re$^{186}$, Re$^{188}$ and In$^{111}$ can be attached via a cysteine residue. Y$^{90}$ can be attached via a lysine residue. I$^{123}$ can be attached using the IODO-GEN method (Fraker et al (1978) Biochem. Biophys. Res. Commun. 80: 49-57).

Several examples can be mentioned to illustrate the knowledge of the person skilled in the art in the field of ARC such as Zevalin® which is an ARC composed of an anti-CD20 monoclonal antibody and In$^{111}$ or Y$^{90}$ radioisotope bound by a thiourea linker-chelator (Wiseman et at (2000) Eur. Jour. Nucl. Med. 27(7):766-77; Wiseman et al (2002) Blood 99(12):4336-42; Witzig et at (2002) J. Clin. Oncol. 20(10):2453-63; Witzig et al (2002) J. Clin. Oncol. 20(15): 3262-69); or Mylotarg® which is composed of an anti-CD33 antibody linked to calicheamicin, (U.S. Pat. Nos. 4,970,198; 5,079,233; 5,585,089; 5,606,040; 5,693,762; 5,739,116; 5,767,285; 5,773,001). More recently, it can also be mentioned the ADC referred as Adcetris (corresponding to the Brentuximab vedotin) which has been recently accepted by the FDA in the treatment of Hodgkin's lymphoma (Nature, vol. 476, pp 380-381, 25 Aug. 2011).

In a third preferred embodiment of the invention, the immunoconjugate consists of a binding protein linked to at least a toxin. Such an immunoconjugate is referred as an antibody-toxin conjugate (or "ATC") when the binding protein is an antibody, or an antigen binding fragment thereof.

Toxins are effective and specific poisons produced by living organisms. They usually consist of an amino acid chain which can vary in molecular weight between a couple of hundred (peptides) and one hundred thousand (proteins). They may also be low-molecular organic compounds. Toxins are produced by numerous organisms, e.g., bacteria, fungi, algae and plants. Many of them are extremely poisonous, with a toxicity that is several orders of magnitude greater than the nerve agents.

Toxins used in ATC can include, without limitation, all kind of toxins which may exert their cytotoxic effects by mechanisms including tubulin binding, DNA binding, or topoisomerase inhibition.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Small molecule toxins, such as dolastatins, auristatins, a trichothecene, and CC1065, and the derivatives of these toxins that have toxin activity, are also contemplated herein. Dolastatins and auristatins have been shown to interfere with microtubule dynamics, GTP hydrolysis, and nuclear and cellular division and have anticancer and antifungal activity.

"Linker", "Linker Unit", or "link" means a chemical moiety comprising a covalent bond or a chain of atoms that covalently attaches a binding protein to at least one cytotoxic agent.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cytotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non-cleavable" or "cleavable" linker.

In a preferred embodiment, it consists in a "cleavable linker" facilitating release of the cytotoxic agent in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the cytotoxic agent from the binding protein in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyse dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a Val-Cit linker or a Phe-Lys linker. One advantage of using intracellular proteolytic release of the cytotoxic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolysable under acidic conditions. For example, an acid-labile linker that is hydrolysable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolysable linker is a thioether linker (such as, e.g., a thioether attached to the therapeutic agent via an acylhydrazone bond.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT.

As non-limitative example of non-cleavable or "non-reducible" linkers, it can be mentioned the immunoconjugate Trastuzumab-DM1 (TDM1) which combines trastuzumab with a linked chemotherapy agent, maytansin (Cancer Research 2008; 68: (22). Nov. 15, 2008).

In a preferred embodiment, the immunoconjugate of the invention may be prepared by any method known by the person skilled in the art such as, without limitation, i) reaction of a nucleophilic group of the antigen binding protein with a bivalent linker reagent followed by reaction with the cytotoxic agent or ii) reaction of a nucleophilic group of a cytotoxic agent with a bivalent linker reagent followed by reaction with the nucleophilic group of the antigen binding protein.

Nucleophilic groups on antigen binding protein include, without limitation, N-terminal amine groups, side chain amine groups, e.g. lysine, side chain thiol groups, and sugar hydroxyl or amino groups when the antigen binding protein is glycosylated. Amine, thiol, and hydroxyl groups are nucleophilic and capable of reacting to form covalent bonds with electrophilic groups on linker moieties and linker reagents including, without limitation, active esters such as NHS esters, HOBt esters, haloformates, and acid halides; alkyl and benzyl halides such as haloacetamides; aldehydes, ketones, carboxyl, and maleimide groups. The antigen binding protein may have reducible interchain disulfides, i.e. cysteine bridges. The antigen binding proteins may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antigen binding protein through any reaction known by the person skilled in the art. As non-limitative example, reactive thiol groups may be introduced into the antigen binding protein by introducing one or more cysteine residues.

Immunoconjugates may also be produced by modification of the antigen binding protein to introduce electrophilic moieties, which can react with nucleophilic substituents on the linker reagent or cytotoxic agent. The sugars of glycosylated antigen binding protein may be oxidized to form aldehyde or ketone groups which may react with the amine group of linker reagents or cytotoxic agent. The resulting imine Schiff base groups may form a stable linkage, or may be reduced to form stable amine linkages. In one embodiment, reaction of the carbohydrate portion of a glycosylated antigen binding protein with either galactose oxidase or sodium meta-periodate may yield carbonyl (aldehyde and ketone) groups in the protein that can react with appropriate groups on the drug. In another embodiment, proteins containing N-terminal serine or threonine residues can react with sodium meta-periodate, resulting in production of an aldehyde in place of the first amino acid.

In certain preferred embodiments, the linker unit may have the following general formula:

-Ta-Ww-Yywherein:
-T- is a stretcher unit;
a is 0 or 1;
-W- is an amino acid unit;
w is independently an integer ranging from 1 to 12;
-Y- is a spacer unit;
y is 0, 1 or 2.

The stretcher unit (-T-), when present, links the antigen binding protein to an amino acid unit (-W-). Useful functional groups that can be present on the antigen binding protein, either naturally or via chemical manipulation, include sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of the antigen binding protein, if present. Alternatively, sulfhydryl groups can be generated by reaction of an amino group of a lysine moiety of the antigen binding protein with 2-iminothiolane or other sulfhydryl generating reagents. In specific embodiments, the antigen binding protein is a recombinant antibody and is engineered to carry one or more lysine residues. More preferably, the antigen binding protein can be engineered to carry one or more Cysteines (cf. ThioMabs).

In certain specific embodiments, the stretcher unit forms a bond with a sulfur atom of the antigen binding protein. The sulfur atom can be derived from a sulfhydryl (—SH) group of a reduced antigen binding protein.

In certain other specific embodiments, the stretcher unit is linked to the antigen binding protein via a disulfide bond between a sulfur atom of the antigen binding protein and a sulfur atom of the stretcher unit.

In other specific embodiments, the reactive group of the stretcher contains a reactive site that can be reactive to an amino group of the antigen binding protein. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates.

In yet another aspect, the reactive function of the stretcher contains a reactive site that is reactive to a modified carbohydrate group that can be present on the antigen binding protein. In a specific embodiment, the antigen binding protein is glycosylated enzymatically to provide a carbohydrate moiety (to be noticed that, when the antigen binding protein is an antibody, said antibody is generally naturally glycosylated). The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

The amino acid unit (-W-) links the stretcher unit (-T-) to the Spacer unit (-Y-) if the spacer unit is present, and links the stretcher unit to the cytotoxic agent if the spacer unit is absent.

As above mentioned, -Ww- may be a dipeptide, tripeptide, tetrapeptide, pentapeptide, hexapeptide, heptapeptide, octapeptide, nonapeptide, decapeptide, undecapeptide or dodecapeptide unit In some embodiments, the amino acid unit may comprise amino acid residues such as, without limitation, alanine, valine, leucine, isoleucine, methionine, phenylalanine, tryptophan, proline, lysine protected with acetyl or formyl, arginine, arginine protected with tosyl or nitro groups, histidine, ornithine, ornithine protected with acetyl or formyl and citrulline. Exemplary amino acid linker components include preferably a dipeptide, a tripeptide, a tetrapeptide or a pentapeptide.

Exemplary dipeptides include: Val-Cit, Ala-Val, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-$N^9$-tosyl-Arg, Phe-$N^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO. 33), Ala-Leu-Ala-Leu (SEQ ID NO. 34).

Exemplary pentapeptide include: Pro-Val-Gly-Val-Val (SEQ ID NO. 35).

Amino acid residues which comprise an amino acid linker component include those occurring naturally, as well as minor amino acids and non-naturally occurring amino acid analogues, such as citrulline. Amino acid linker components can be designed and optimized in their selectivity for enzymatic cleavage by a particular enzyme, for example, a tumour-associated protease, cathepsin B, C and D, or a plasmin protease.

The amino acid unit of the linker can be enzymatically cleaved by an enzyme including, but not limited to, a tumour-associated protease to liberate the cytotoxic agent.

The amino acid unit can be designed and optimized in its selectivity for enzymatic cleavage by a particular tumour-associated protease. The suitable units are those whose cleavage is catalysed by the proteases, cathepsin B, C and D, and plasmin.

The spacer unit (-Y-), when present, links an amino acid unit to the cytotoxic agent. Spacer units are of two general types: self-immolative and non-self-immolative. A non-self-immolative spacer unit is one in which part or all of the spacer unit remains bound to the cytotoxic agent after enzymatic cleavage of an amino acid unit from the immunoconjugate. Examples of a non-self-immolative spacer unit include, but are not limited to a (glycine-glycine) spacer unit and a glycine spacer unit. To liberate the cytotoxic agent, an independent hydrolysis reaction should take place within the target cell to cleave the glycine-drug unit bond.

In another embodiment, a non-self-immolative the spacer unit (-Y-) is -Gly-.

In one embodiment, the immunoconjugate lacks a spacer unit (y=0). Alternatively, an immunoconjugate containing a self-immolative spacer unit can release the cytotoxic agent without the need for a separate hydrolysis step. In these embodiments, -Y- is a p-aminobenzyl alcohol (PAB) unit that is linked to -Ww- via the nitrogen atom of the PAB group, and connected directly to -D via a carbonate, carbamate or ether group.

Other examples of self-immolative spacers include, but are not limited to, aromatic compounds that are electronically equivalent to the PAB group such as 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional cytotoxic agents.

In a specific embodiment, the ADC of the invention is ADCα.

The present ADCα is of the following formula (I):

$$\text{Ab-(L-D)}_n \qquad \qquad (I)$$

or a pharmaceutically acceptable salt thereof,
wherein
Ab is an antibody, or an antigen binding fragment thereof, capable of binding to the human IGF-1R selected from:
  i) an antibody which comprises the three heavy-chain CDRs of sequence SEQ ID No. 1, 2 and 3 and the three light-chain CDRs of sequence SEQ ID No. 4, 5 and 6;
  ii) an antibody that competes for binding to IGF-1R with the antibody of i); and
  iii) an antibody that binds to the same epitope of IGF-1R as the antibody of i);
L is a linker;
D is a drug moiety of the following formula (II):

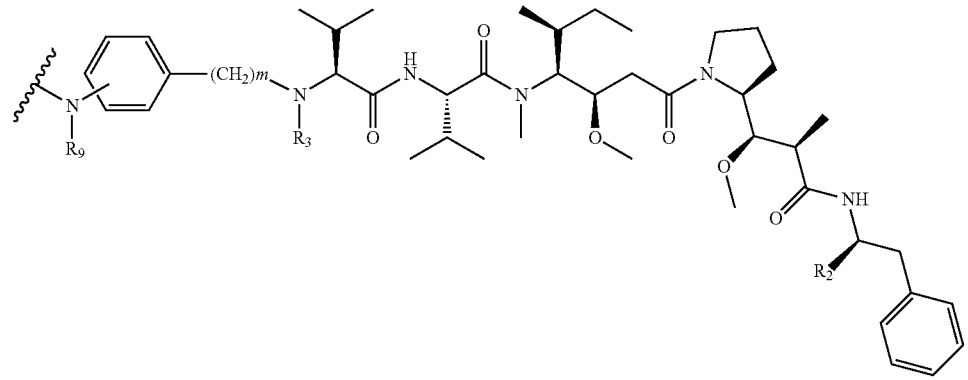

wherein:
  $R_2$ is COOH, COOCH$_3$ or thiazolyl;
  $R_3$ is H or (C$_1$-C$_6$)alkyl;
  $R_9$ is H or (C$_1$-C$_6$)alkyl;
  m is an integer comprised between 1 and 8;
  the wavy line indicates the point of attachment to L; and
  n is 1 to 12.

In an embodiment, ADCα comprises Ab is selected from:
a) an antibody comprising the three heavy-chain CDRs of sequence SEQ ID No. 7, 2 and 3 and the three light-chain CDRs of sequence SEQ ID No. 9, 5 and 11;
b) an antibody comprising the three heavy-chain CDRs of sequence SEQ ID No. 7, 2 and 3 and the three light-chain CDRs of sequence SEQ ID No. 10, 5 and 11;

c) an antibody comprising the three heavy-chain CDRs of sequence SEQ ID No. 7, 2 and 3 and the three light-chain CDRs of sequence SEQ ID No. 9, 5 and 12; and
d) an antibody comprising the three-heavy chain CDRs of sequence SEQ ID No. 8, 2 and 3 and the three light-chain CDRs of sequence SEQ ID No. 9, 5 and 11.

In an embodiment, ADCα comprises Ab is selected from:
a) an antibody comprising a heavy-chain variable domain of sequence SEQ ID No. 13 and the three light-chain CDRs of sequence SEQ ID No. 9, 5 and 11;
b) an antibody comprising a heavy-chain variable domain of sequence SEQ ID No. 14 and the three light-chain CDRs of sequence SEQ ID No. 10, 5 and 11;
c) an antibody comprising a heavy-chain variable domain of sequence SEQ ID No. 15 and the three light-chain CDRs of sequence SEQ ID No. 9, 5 and 12;
d) an antibody comprising a heavy-chain variable domain of sequence SEQ ID No. 16 and the three light-chain CDRs of sequence SEQ ID No. 9, 5 and 11; and
e) an antibody comprising a heavy-chain variable domain of sequence SEQ ID No. 17 and the three light-chain CDRs of sequence SEQ ID No. 9, 5 and 12.

In an embodiment, ADCα comprises Ab is selected from:
a) an antibody comprising a light-chain variable domain of sequence SEQ ID No. 18 and the three heavy-chain CDRs of sequence SEQ ID No. 7, 2 and 3;
b) an antibody comprising a light-chain variable domain of sequence SEQ ID No. 19 and the three heavy-chain CDRs of sequence SEQ ID No. 7, 2 and 3;
c) an antibody comprising a light-chain variable domain of sequence SEQ ID No. 20 and the three heavy-chain CDRs of sequence SEQ ID No. 7, 2 and 3;
d) an antibody comprising a light-chain variable domain of sequence SEQ ID No. 21 and the three heavy-chain CDRs of sequence SEQ ID No. 8, 2 and 3; and
e) an antibody comprising a light-chain variable domain of sequence SEQ ID No. 22 and the three heavy-chain CDRs of sequence SEQ ID No. 7, 2 and 3.

In an embodiment, ADCα comprises Ab is selected from:
i) the antibodies 208F2, 212A11, 214F8, 219D6 and 213B10;
ii) the antibodies which compete for binding to IGF-1R with the antibodies of i); and
iii) the antibodies which bind to the same epitope of IGF-1R as the antibodies of i).

Ab is preferably a humanized antibody.

In an embodiment of the ADCα, Ab is selected from an antibody comprising:
a) a heavy chain having CDR-H1, CDR-H2 and CDR-H3 of sequences SEQ ID Nos. 7, 2 and 3, respectively, and FR1, FR2 and FR3 derived from the human germline IGHV1-46*01 (SEQ ID No. 46), and the FR4 derived from the human germline IGHJ4*01 (SEQ ID No. 48); and
b) a light chain having CDR-L1, CDR-L2 and CDR-L3 of sequences SEQ ID Nos. 9, 5 and 11, respectively, and FR1, FR2 and FR3 derived from the human germline IGKV1-39*01 (SEQ ID No. 47), and the FR4 derived from the human germline IGKJ4*01 (SEQ ID No. 49).

Ab is selected from:
a) an antibody comprising a heavy-chain variable domain of sequence SEQ ID No. 33 or any sequence exhibiting at least 80% identity with SEQ ID No. 33 and the three light-chain CDRs of sequences SEQ ID Nos. 9, 5 and 11; and
b) an antibody comprising a heavy-chain variable domain of sequence SEQ ID No. 34 or any sequence exhibiting at least 80% identity with SEQ ID No. 34 and the three light-chain CDRs of sequences SEQ ID Nos. 9, 5 and 11.

In an embodiment of ADCα, Ab is selected from:
a) an antibody comprising a light-chain variable domain of sequence SEQ ID No. 35 or any sequence exhibiting at least 80% identity with SEQ ID No. 35 and the three heavy-chain CDRs of sequences SEQ ID Nos. 7, 2 and 3; and
b) an antibody comprising a heavy-chain variable domain of sequence SEQ ID No. 36 or any sequence exhibiting at least 80% identity with SEQ ID No. 36 and the three heavy-chain CDRs of sequences SEQ ID Nos. 7, 2 and 3.

In an embodiment of ADCα, Ab is selected from:
a) an antibody comprising or consisting of a heavy chain of sequence SEQ ID No. 37 or any sequence exhibiting at least 80% identity with SEQ ID No. 37 and a light chain of sequence SEQ ID No. 39 or any sequence exhibiting at least 80% identity with SEQ ID No. 39; and
b) an antibody comprising or consisting of a heavy chain of sequence SEQ ID No. 38 or any sequence exhibiting at least 80% identity with SEQ ID No. 38 and a light chain of sequence SEQ ID No. 40 or any sequence exhibiting at least 80% identity with SEQ ID No. 40.

In an embodiment of ADCα, Ab is selected from:
a) an antibody comprising a heavy-chain variable domain of sequence selected from SEQ ID Nos. 56, 62, 64, 66, 68, 70, 72, 74, 76, 78 and 80 or any sequence with at least 80% identity with SEQ ID No.56, 62, 64, 66, 68, 70, 72, 74, 76, 78 or 80; and the three light-chain CDRs of sequences SEQ ID Nos. 9, 5 and 11;
b) an antibody comprising a light-chain variable domain of sequence selected from SEQ ID Nos. 57 and 60 or any sequence with at least 80% identity with SEQ ID Nos. 57 or 60; and the three heavy-chain CDRs of sequences SEQ ID Nos. 7, 2 and 3; and
c) an antibody comprising a heavy-chain variable domain of sequence selected from SEQ ID Nos. 56, 62, 64, 66, 68, 70, 72, 74, 76, 78 and 80 or any sequence with at least 80% identity with SEQ ID Nos.56, 62, 64, 66, 68, 70, 72, 74, 76, 78 or 80; and a light-chain variable domain of sequence selected from SEQ ID Nos. 57 or 60 or any sequence with at least 80% identity with SEQ ID Nos. 57 or 60.

In an embodiment of ADCα, Ab is selected from:
a) a heavy chain of sequence selected from SEQ ID Nos. 58, 63, 65, 67, 69, 71, 73, 75, 77, 79 and 81 or any sequence with at least 80% identity with SEQ ID Nos. 58, 63, 65, 67, 69, 71, 73, 75, 77, 79 or 81; and
b) a light chain of sequence selected from SEQ ID Nos. 59 and 61 or any sequence with at least 80% identity with SEQ ID Nos. 59 or 61.

In an embodiment of ADCα, L is a linker of the following formula (III):

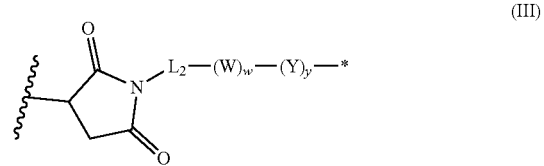

wherein
L$_2$ is (C$_4$-C$_{10}$)cycloalkyl-carbonyl, (C$_2$-C$_6$)alkyl or (C$_2$-C$_6$)alkyl-carbonyl;
W is an amino acid unit; w is an integer comprised between 0 and 5;
Y is PAB-carbonyl with PAB being

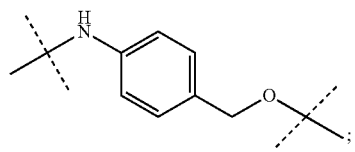

y is 0 or 1;
the asterisk indicates the point of attachment to D; and
the wavy line indicates the point of attachment to Ab.
An embodiment of the invention relates to ADCα wherein L$_2$ is of the following formula:

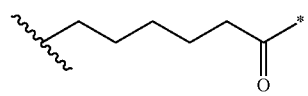 [SMILES: *CCCCCC(*)=O]

wherein
the asterisk indicates the point of attachment to (W)$_w$; and
the wavy line indicates the point of attachment to the nitrogen atom of the maleimide moiety of formula:

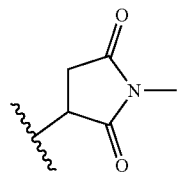 [SMILES: *C1CC(=O)N(C)C1=O]

In an embodiment of ADCα, w=0, or w=2 and then (W)$_w$ is selected from:

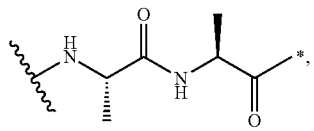

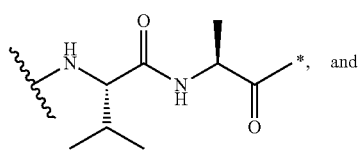, and

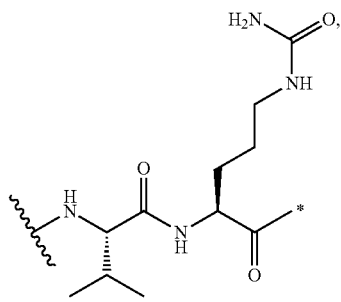

wherein
the asterisk indicates the point of attachment to (Y)$_y$; and
the wavy line indicates the point of attachment to L$_2$.
An embodiment of the invention relates to ADCα wherein L is selected from:

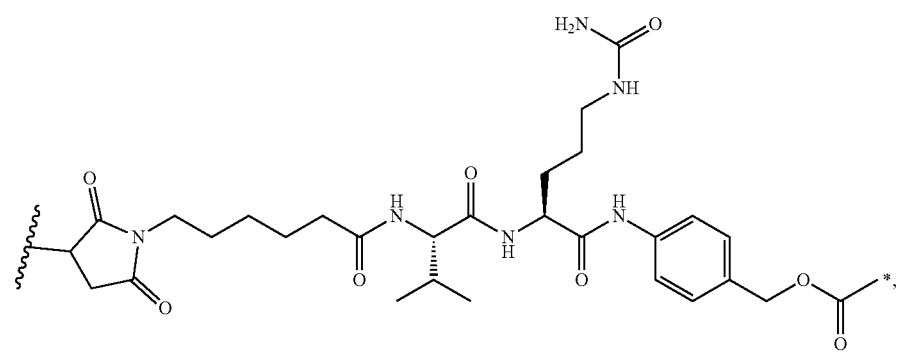

-continued
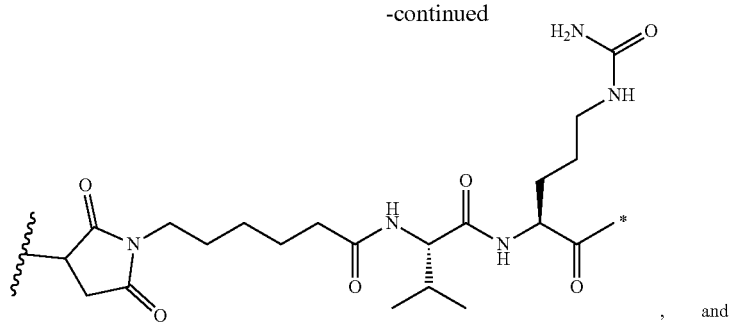
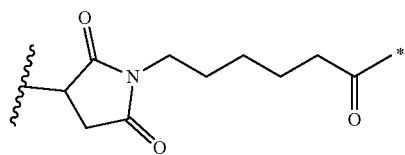
wherein the asterisk indicates the point of attachment to D, and the wavy line indicates the point of attachment to Ab.
An embodiment of the invention relates to ADCα wherein (L-D) is selected from:
(E-11)
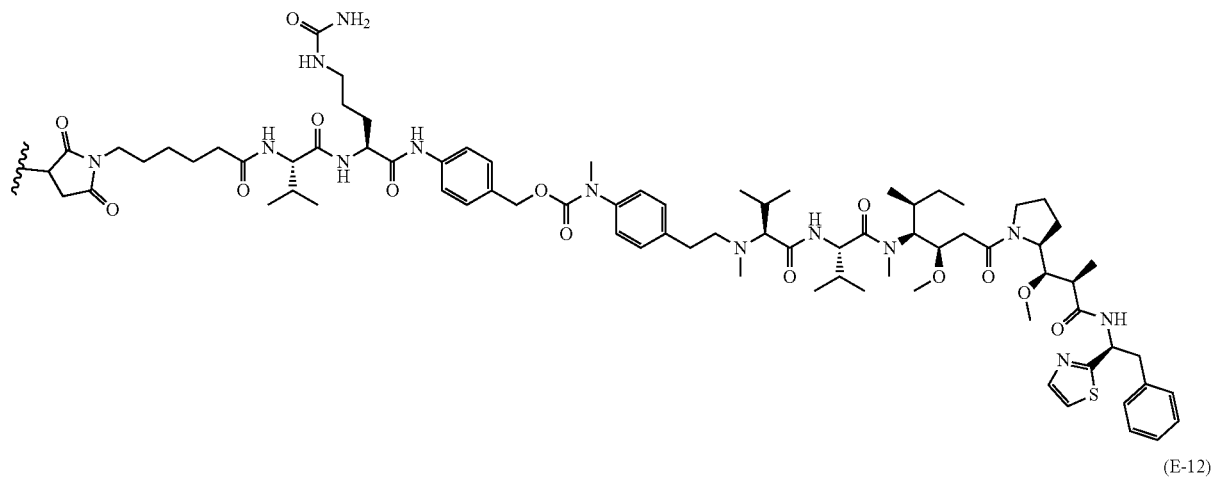
(E-12)
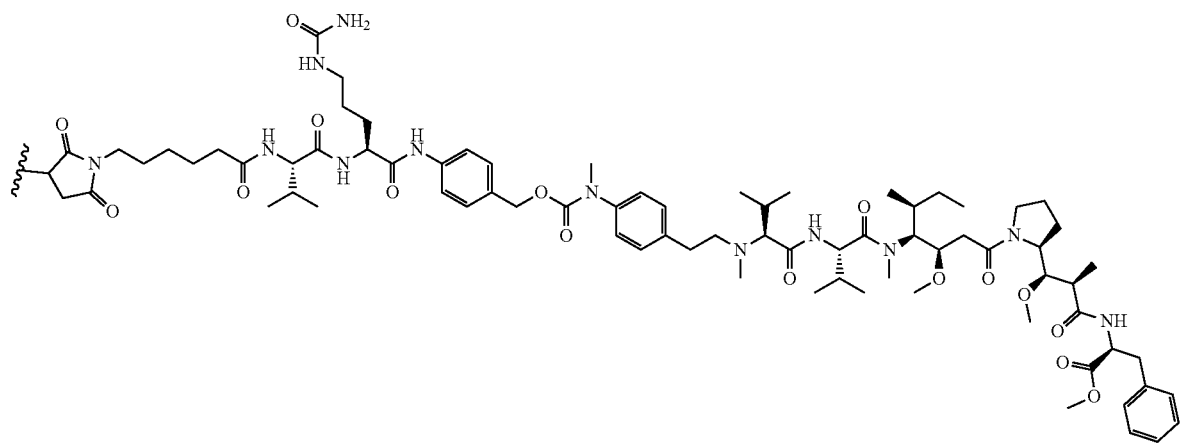

-continued
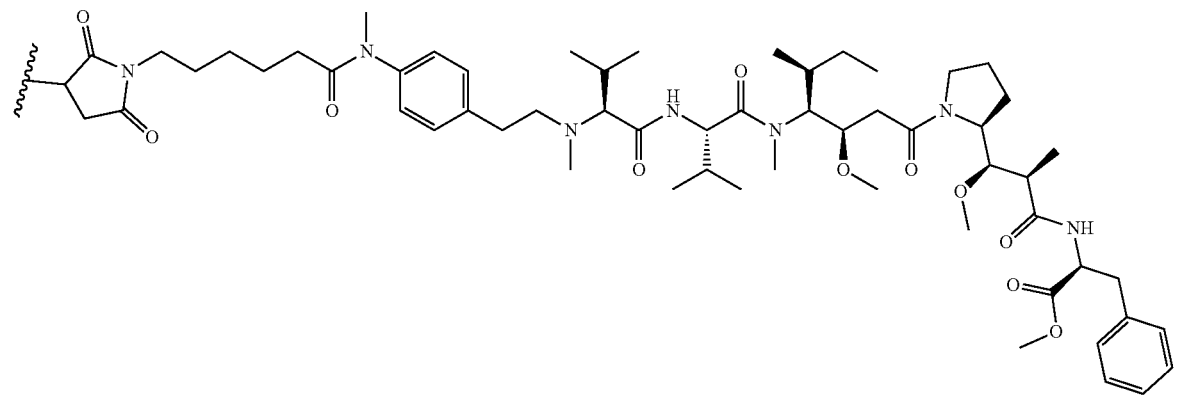
(G-12)
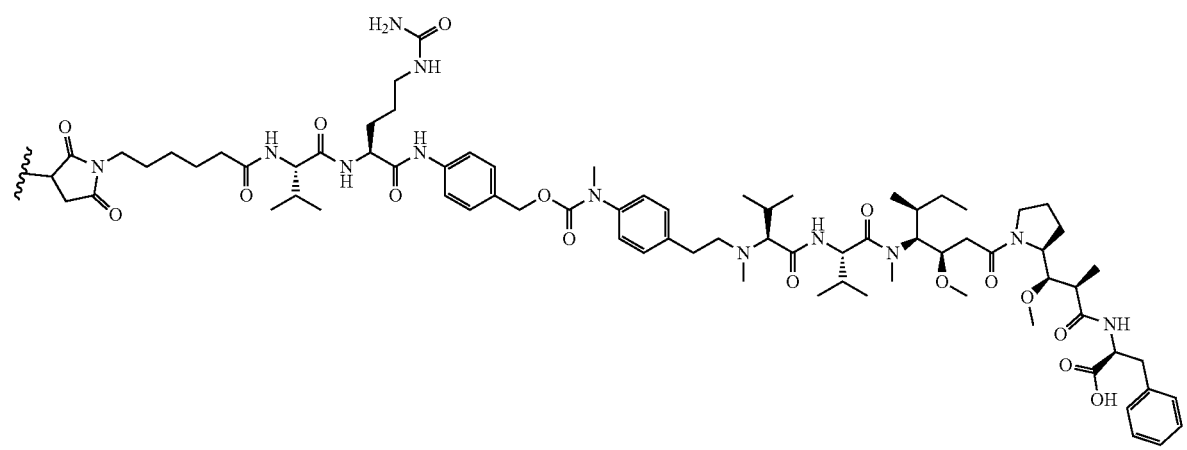
(E-13)
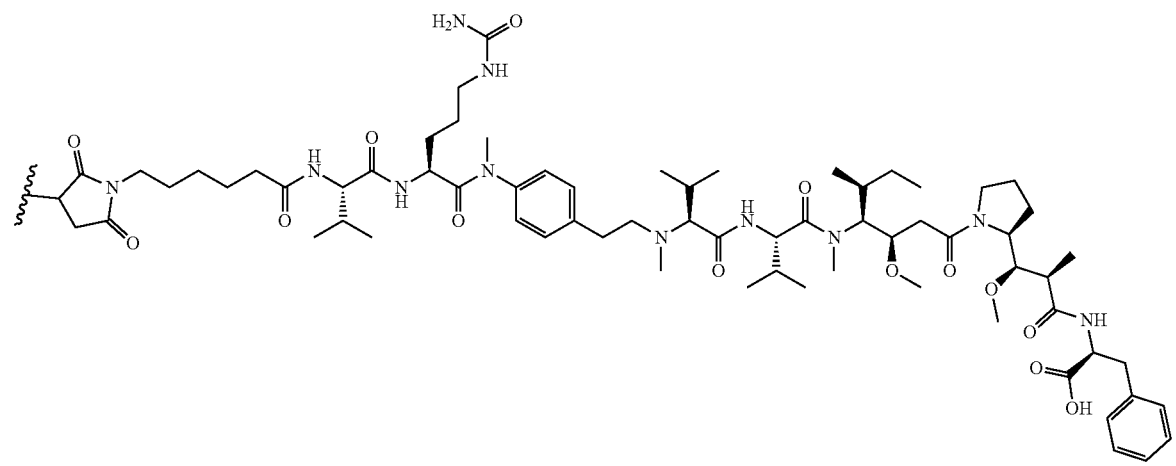
(F-13)

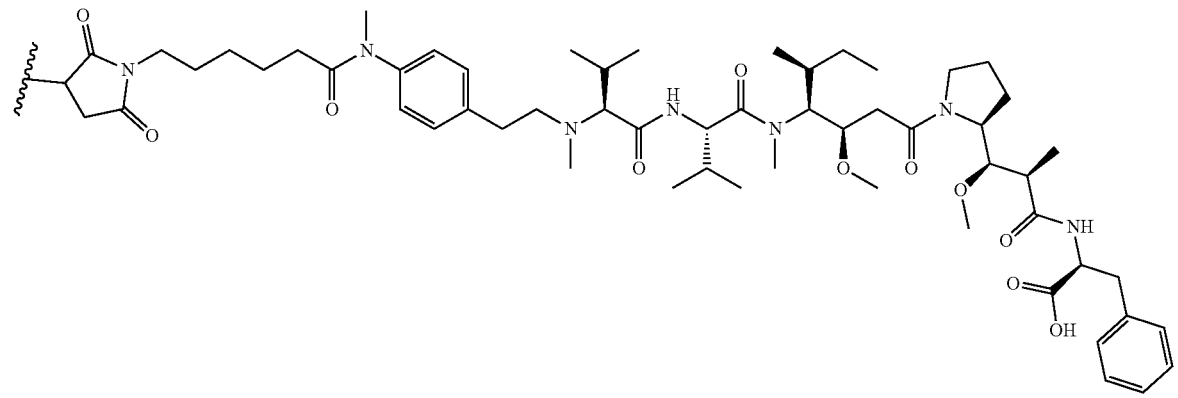
(G-13)
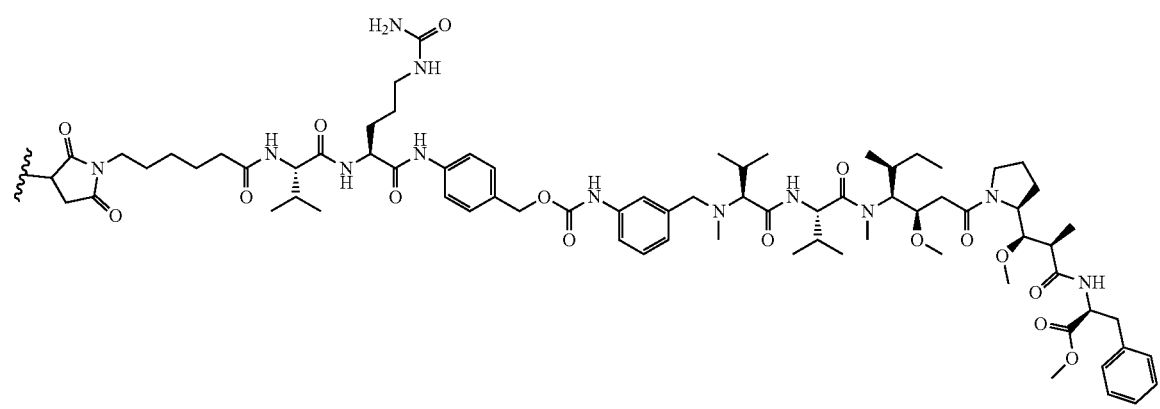
(E-15)
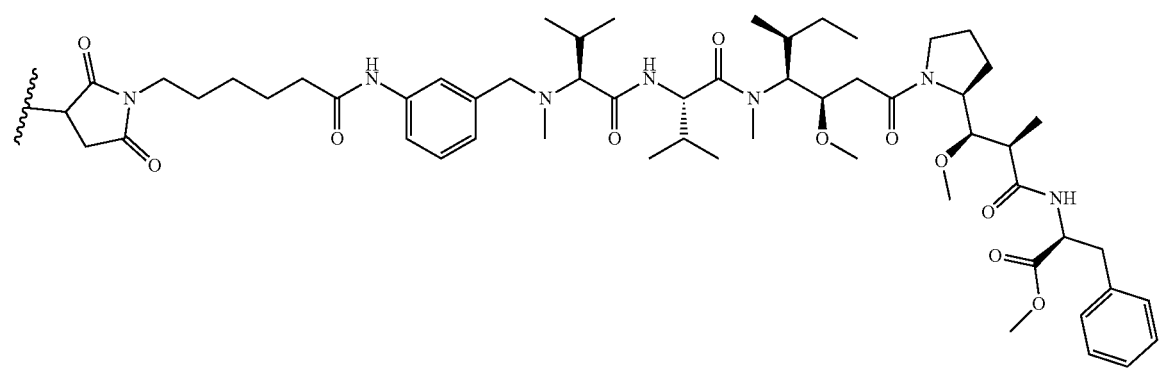
(G-15)

-continued
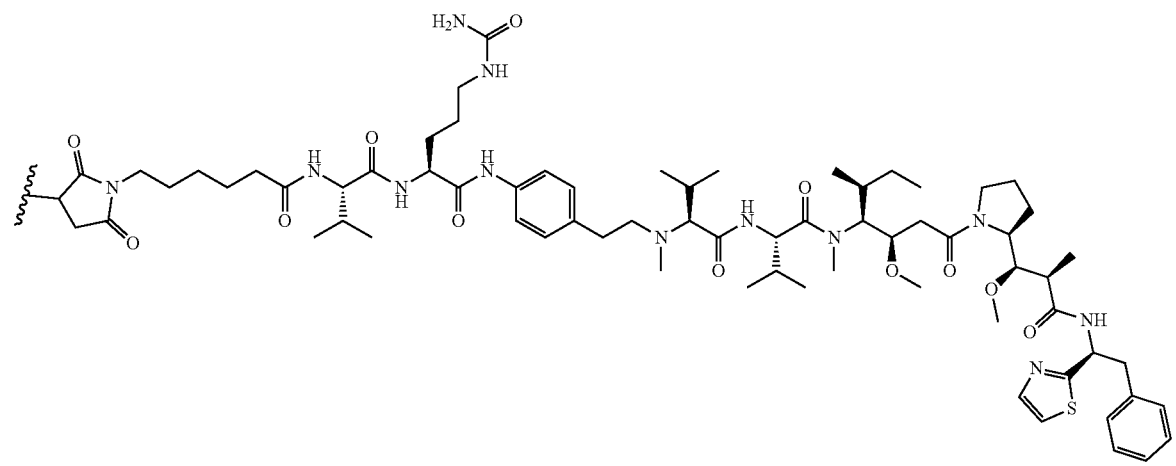
(F-61)
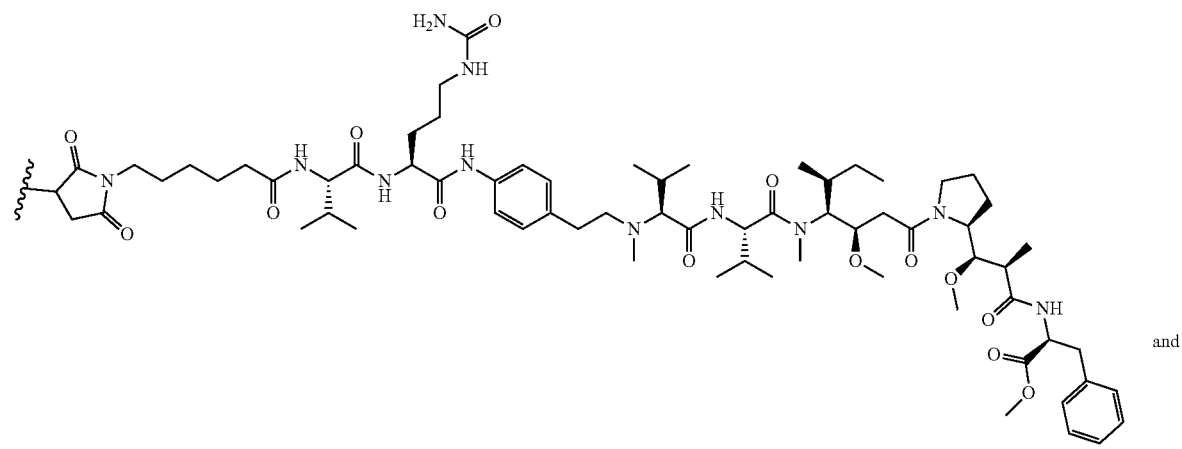
(F-62)
and
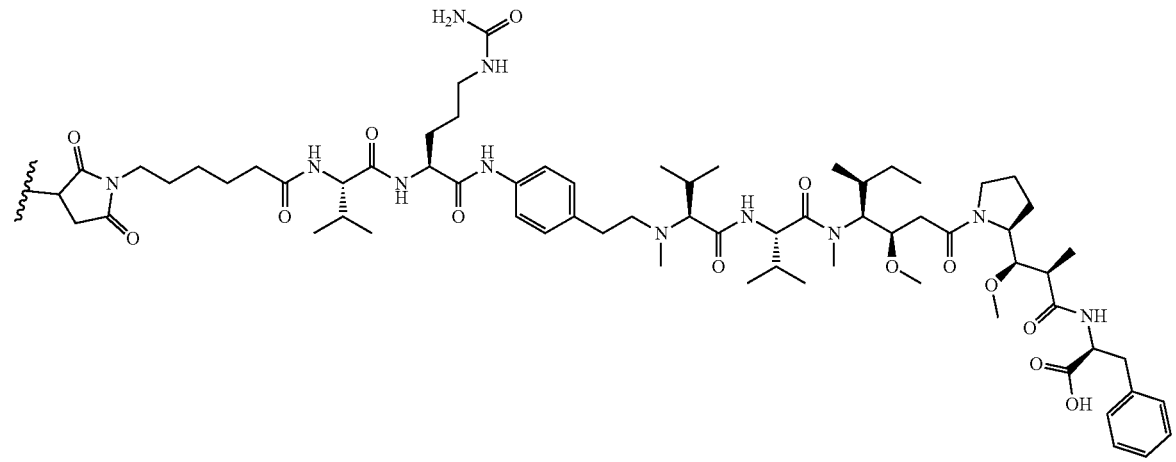
(F-63)
wherein the wavy line indicates the point of attachment to Ab.

An embodiment of the invention relates to ADCα having the formula selected from:
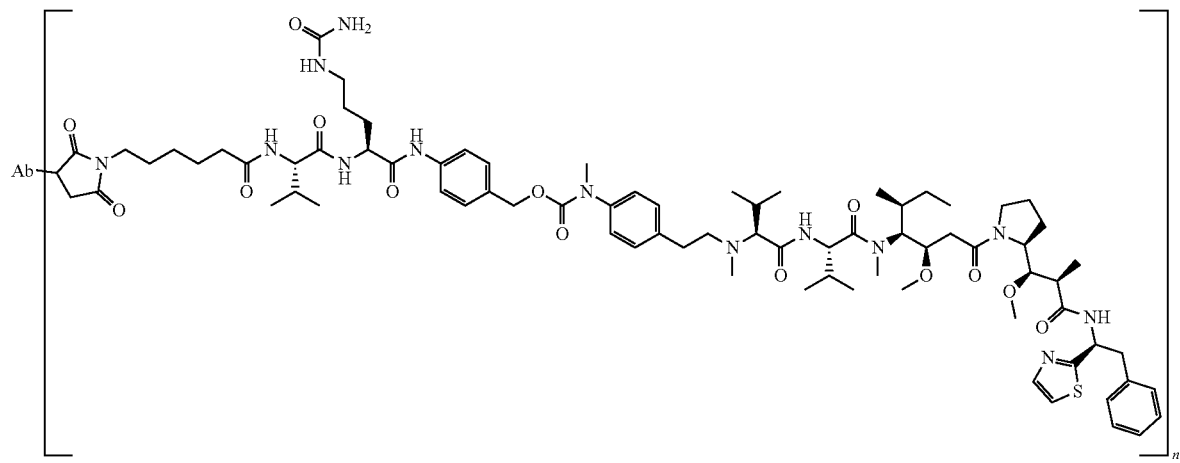
(Ab-E-11)
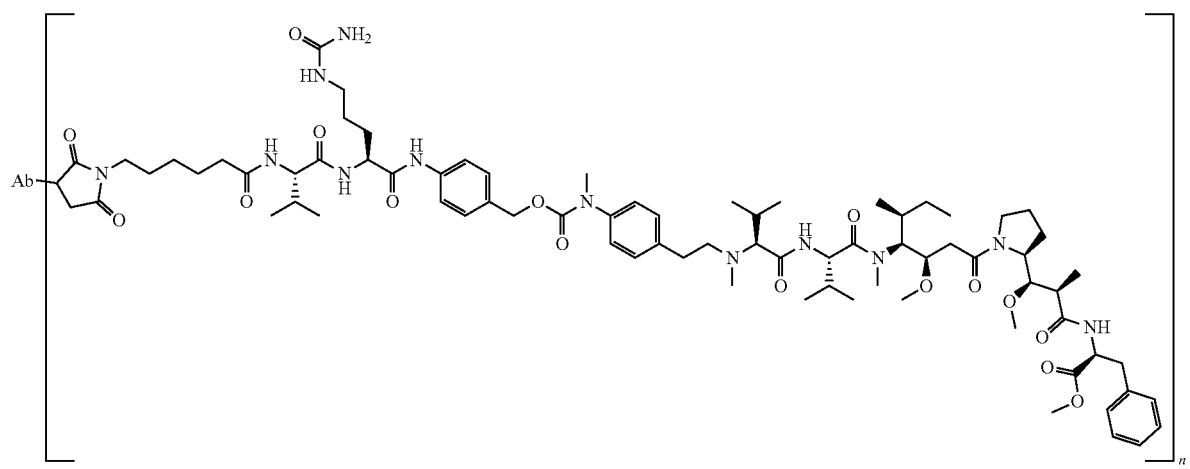
(Ab-E-12)
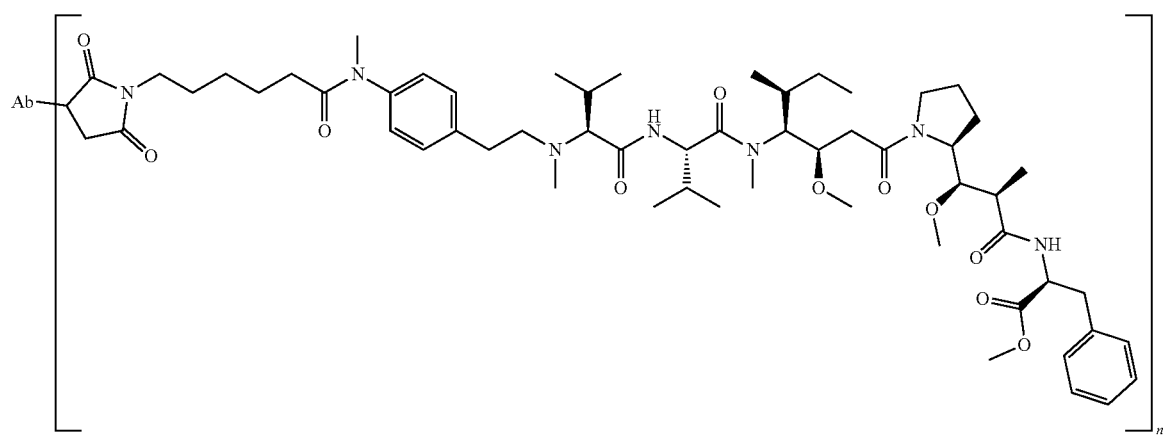
(Ab-G-12)

-continued
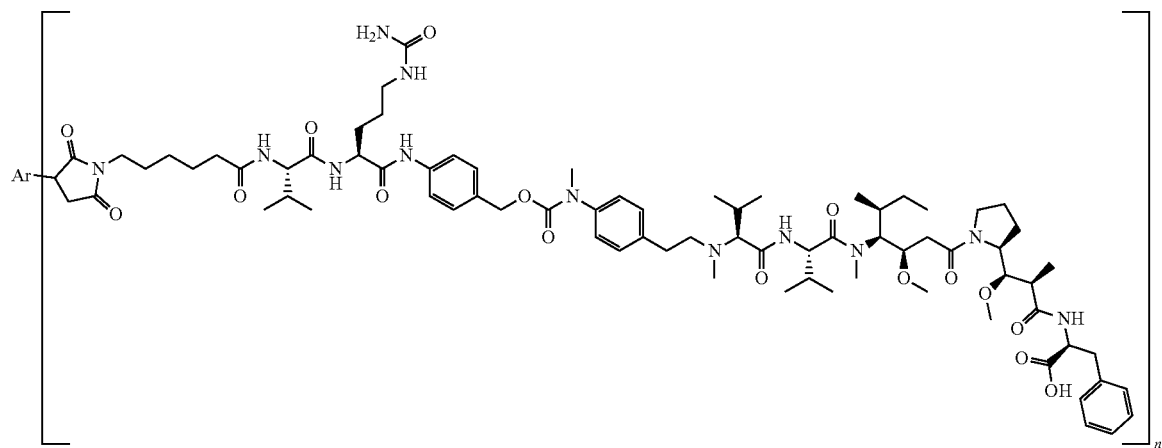
(Ab-E-13)
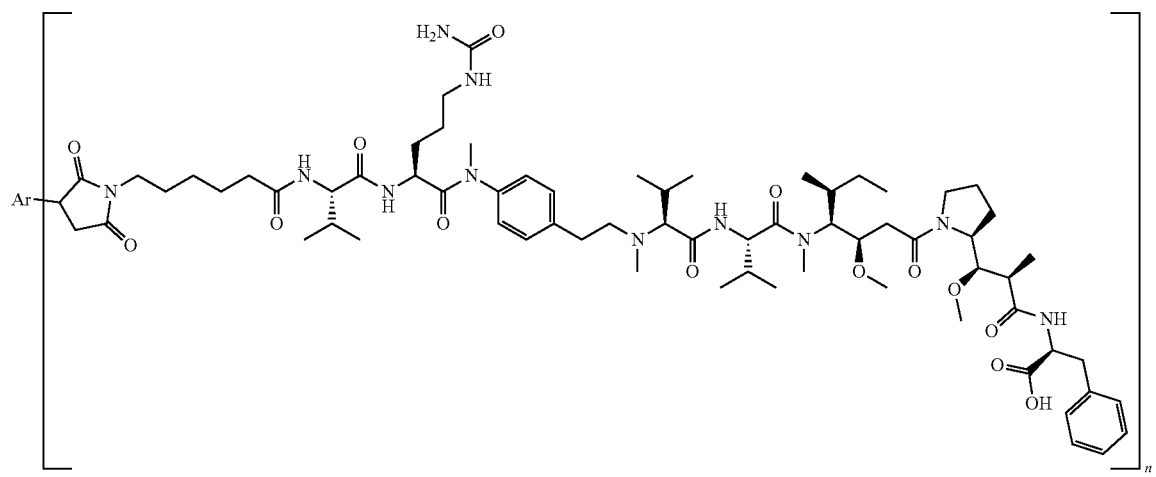
(Ab-F-13)
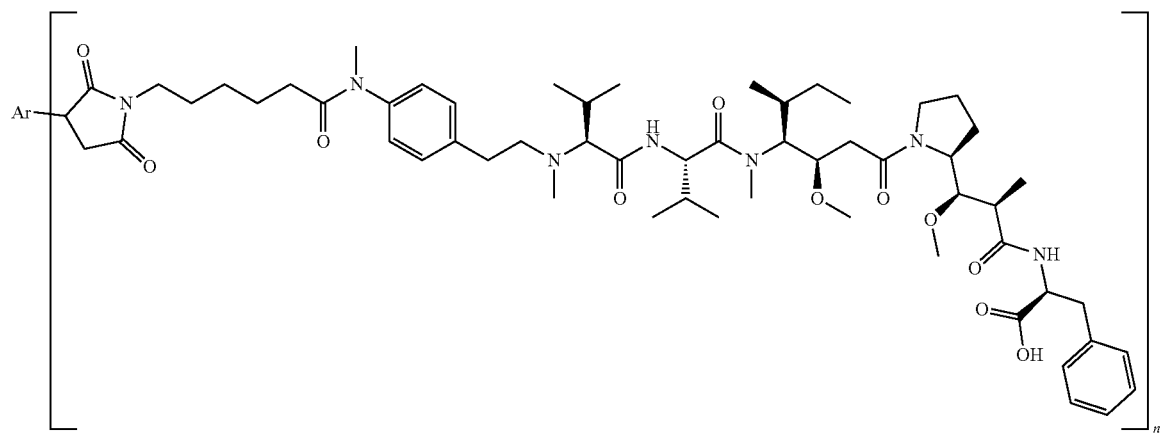
(Ab-G-13)

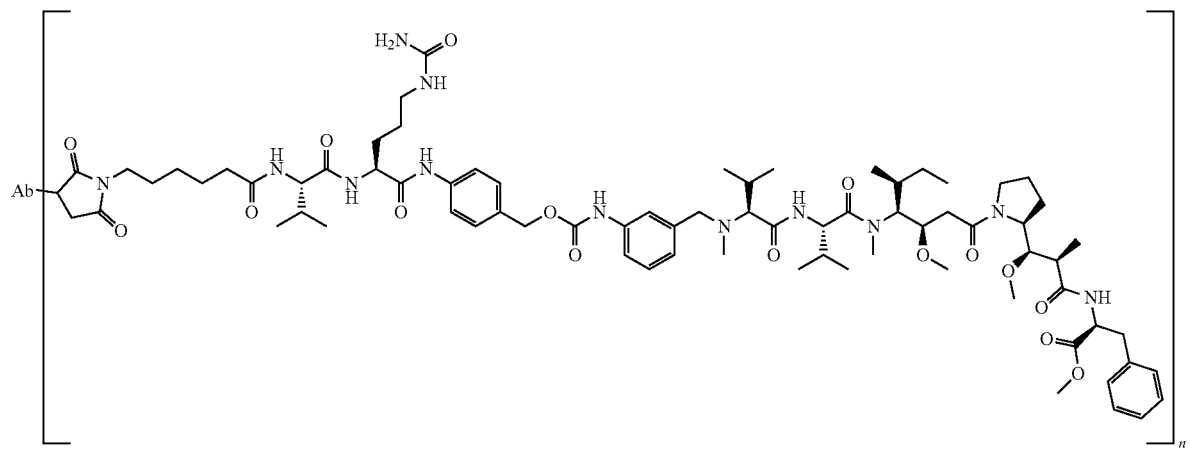
(Ab-E-15)
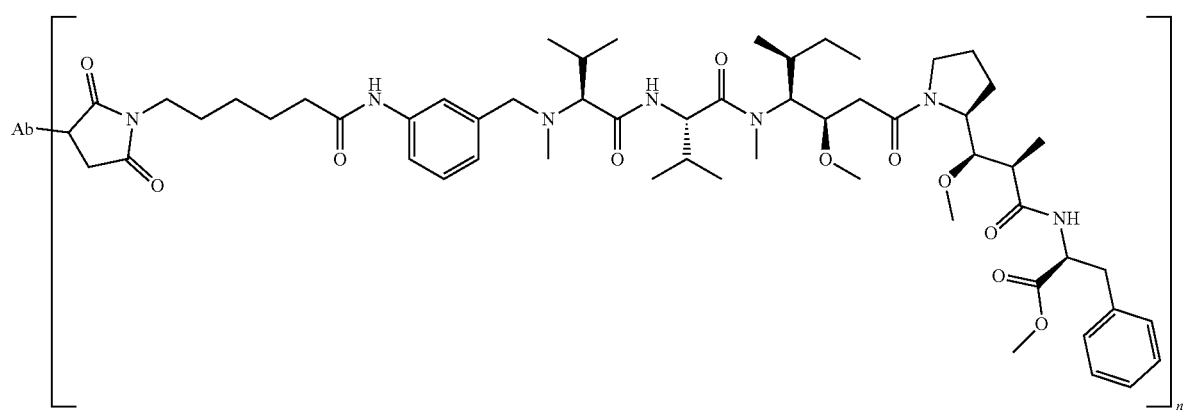
(Ab-G-15)
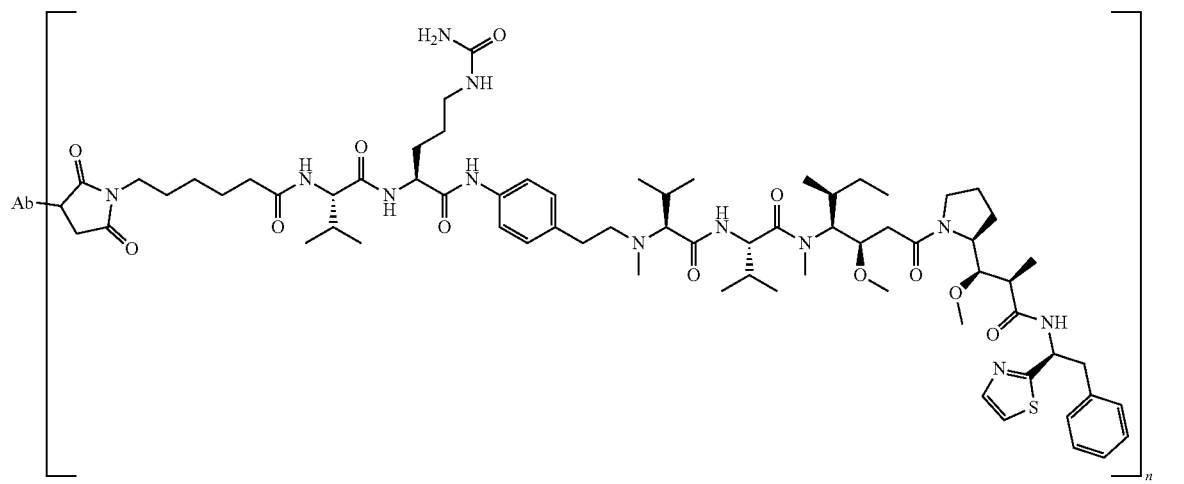
(Ab-F-61)

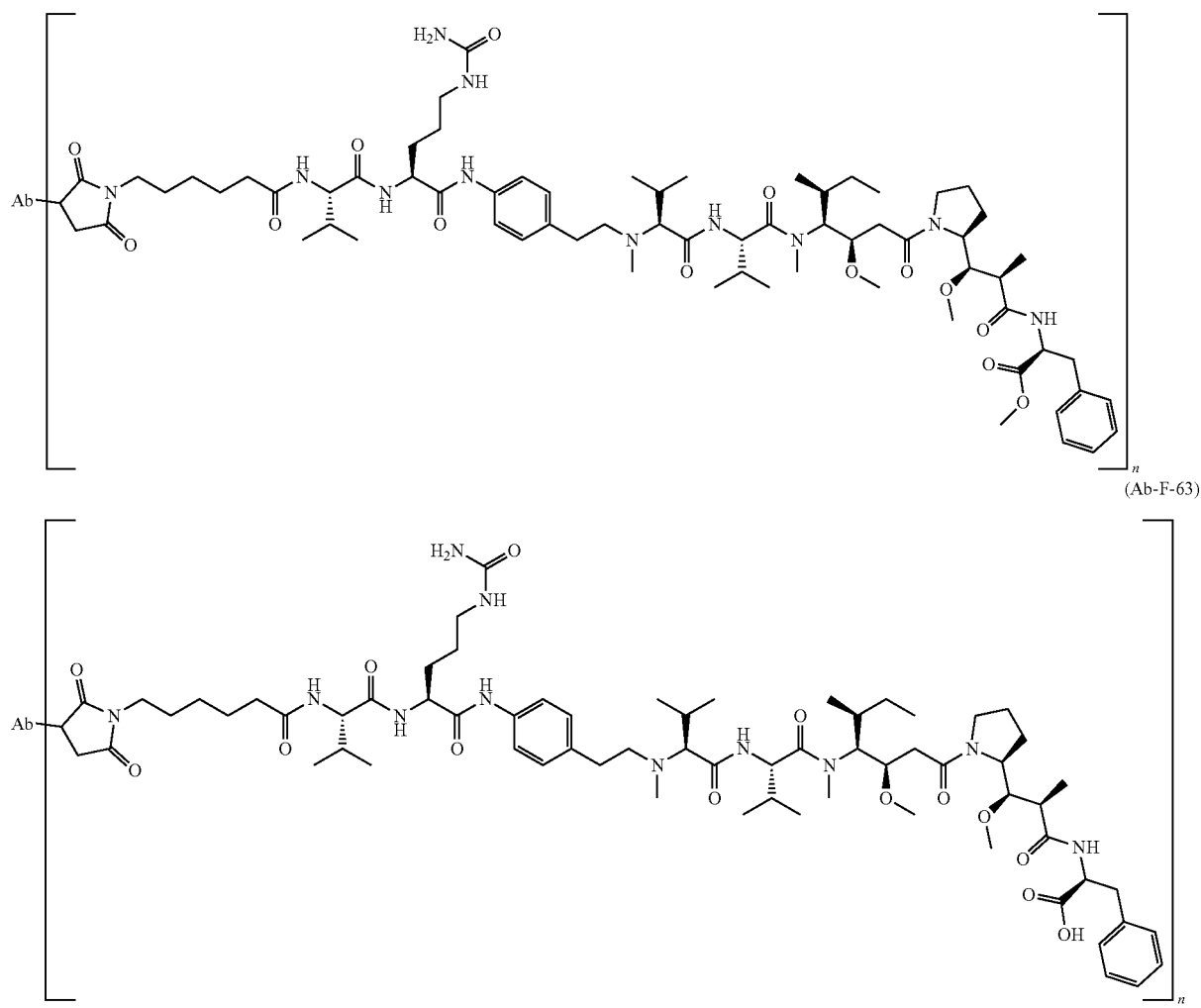

and the pharmaceutically acceptable salts thereof,
wherein Ab is selected in the group consisting of:
  i) the antibodies 208F2, 212A11, 214F8, 219D6 and 213B10;
  ii) the antibodies which compete for binding to IGF-1R with the antibodies of i); and
  iii) the antibodies which bind to the same epitope of IGF-1R as the antibodies of i).

An embodiment of the invention relates to an ADC wherein n is 2.

An embodiment of the invention relates to an ADC wherein n is 4.

In the first step of the method of the invention, a biological sample containing the ADC is contacted with a reagent specific for the Fc domain of an antibody.

As used herein, the term "biological sample" or "sample" refers to a whole organism or a subset of its tissues, cells or component parts (e.g. blood vessel, including artery, vein and capillary, body fluids, including but not limited to blood, serum, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

Preferably, a "biological sample" as used herein refers to any fluid sample that may be taken from a subject, such as a serum sample, a plasma sample, a urine sample, a blood sample, a lymph sample, etc. Further preferred biological samples include samples derived from blood, such as a blood sample, a plasma sample, or a serum sample. Indeed, such samples may be obtained by a completely harmless blood collection from the subject.

In a first embodiment, the ADC is present in the biological sample when said sample is taken from the subject. According to this embodiment, the stability of the ADC can be directly monitored in the subject's samples. Such an embodiment is particularly useful when e.g. the efficacy of a treatment is assessed. According to another embodiment, the ADCC is added to the biological sample after said sample was taken from the subject. The inventors have shown that the behaviour of an ADCC under these conditions is highly similar to the behaviour of said ADCC in vivo. Such an embodiment is particularly advantageous as the behaviour of an ADC in a sample can be assayed easily and reliably. For example, stable ADCs can be selected and isolated with such a method.

Reagents specific for the Fc domain of an antibody are well known in the art. Said reagents bind specifically the Fc domain of the antibody moiety of the ADC. Preferably, said reagents are capable of discriminating between several Fc domains based on the species of origin of the antibody. For example, in one embodiment, said reagent binds specifically any Fc domain of human origin, but not any Fc domain from any other species, e.g. mouse, rat, cynomolgus monkey, et. Such an embodiment is particularly advantageous in e.g., toxicology studies, since the ADC can thus be isolated specifically from the biological sample without contamination from the endogenous antibodies. Such reagents can be for example any type of antibody or antigen-binding fragments thereof which recognize and bind specifically to the Fc domain of an antibody. Advantageously, said antibody or antigen-binding fragment originates from a different species than the antibody whose Fc domain is targeted. For example, goat anti-human IgGs are commercially available (Southern Biotech, Birmingham, Ala., USA). Likewise, CaptureSelect™ ligands (Thermofisher) are based on Camelid-derived single domain [VHH] antibody fragments. Alternatively, it is possible to use reagents which discriminate between recombinant and native antibodies. Such reagents are particularly advantageous because they enable e.g. isolating chimeric or humanized antibodies from a human biological sample. Wang et al., (*MAbs.* 5(4): 540-554, 2013) describe a reagent that preferentially recognizes a panel of recombinant human mAbs over endogenous human immunoglobulins, as well as a method for isolating many other such reagents.

Preferably, said reagent is bound to a solid support, in order to facilitate recovery of the ADC-reagent complex. In general, the solid supports on which can be immobilized ADC/reagents complexes of the invention include any type of support having the structure and composition commonly found for filter media, membranes, etc. Solid carriers include, among resins, resins for affinity chromatography column, the polymer beads, magnetic beads, paramagnetic beads, membrane filter media materials, etc. Solid supports also include inter alia materials based on glass or metal, such as steel, gold, silver, aluminium, copper, silicon, glass, ceramic. Solid supports also include inter alia polymeric materials, such as polyethylene, polypropylene, polyamide, polyvinylidene fluoride, and combinations thereof. Most of these supports are commercially available. For example, beads from synthetic polymers such as polystyrene, polyacrylamide, polyacrylate, or latex are commercially available from numerous sources such as Bio-Rad Laboratories (Richmond, Calif.) and LKB Produkter (Stockholm, Sweden). Beads formed from natural macromolecules and particles such as agarose, cross-linked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia.

In some embodiments, the solid support may be coated with a material to facilitate attachment, binding, complex formation, standing or interacting with the reagent for binding ADC, or reagents comprising said compounds.

Methods of binding molecules to a solid support, either covalently or non-covalently, are well known to those of skill in the art. A variety of solid supports known to those of skill in the art, e.g., beads, plates, columns, dipsticks, membranes, and the like, can be used with the present invention. Preferably, said solid support is selected from beads and plates, such as e.g. the beads used in the examples. The ADC can be recovered from the beads by any of the methods known to the person of skills in the art. Examples of such methods are illustrated in the experimental section.

Analysis of the recovered ADC is performed by any method well-known in the art, including, but not limited to, mass spectrometry (MS), preparative disc-gel electrophoresis, isoelectric focusing, HPLC, reversed-phase HPLC, gel filtration, ion exchange and partition chromatography, precipitation and salting-out chromatography, extraction, and countercurrent distribution, and the like.

The structure of the ADC is preferably determined by MS following isolation of said ADC through binding to a specific reagent, as described above. MS allows for the simultaneous multiplex analysis of complex mixtures of biomolecules, depending on their molecular weight. MS thus enables the identification and quantification of fragments of antibodies bound to the cytotoxic, leading to the determination of the DAR.

MS requires less analyte material to provide high-quality information about peptides than other current methods. Because it can provide detailed structural information, mass spectrometry is a valuable analytical tool for biochemical mixture analysis and protein identification. For example, capillary liquid chromatography combined with electrospray ionization tandem mass spectrometry has been used for large-scale protein identification without gel electrophoresis.

Accordingly, in a preferred embodiment, purified ADCs are characterized by mass spectrometry (MS), tandem mass spectrometry (MS-MS), and/or MS 3 analysis. In this embodiment, ADCs which are isolated are then analysed by mass spectroscopy in order to determine the DAR of each ADC.

There are a variety of mass spectroscopy techniques which can be employed in the subject method. When the method of the present invention is practiced, simultaneous identification and quantification of a protein using a tandem mass spectrometer is general assumed. Examples of the mass spectrometer to be used for the method of the present invention include a quadrupolar time-of-flight tandem mass spectrometer (MS/MS), a Fourier-transform mass spectrometer (FT-MS) and the like. The apparatus configuration thereof may be similar to the conventional ones.

In certain embodiments, the proteins are further separated by reverse phase chromatography before analysis by MS. Advantageously, MS is used in the method of the invention for the determination of the DAR of an ADC with the help of separation techniques such as gas chromatography (GC) and liquid chromatography (LC). Preferably, the MS used in the method of the invention is coupled with liquid chromatography (LC-MS). It should be noted that, in order to obtain structural information with the ionization techniques compatible with LC-MS, it is preferable, although not compulsory, to use tandem mass spectrometry. Tandem mass spectrometry is accomplished by selecting out the ion of interest with a mass spectrometer, fragmenting the ion and measuring the masses of the fragment ions using another mass spectrometer.

In certain preferred embodiments, the proteins are cleaved into smaller peptide fragments. For instance, the proteins can be fragmented by enzymatic hydrolysis to produce peptide fragments having carboxy-terminal lysine or arginine residues. In certain preferred embodiments, the proteins are fragmented by treatment with trypsin.

In certain embodiments, the proteins are mass-modified with isotopic labels.

The inventors have found that elution of an ADC isolated by any of the methods described above without prior treatment induces ADC dissociation. Fragments of various sizes, ranging from e.g., 25 to 150 kDa, with different mass response factors can be detected. The % of each species cannot be determined, thus seriously impairing a meaningful calculation of the DAR.

However, the inventors have also found that reducing the disulfide bonds of the antibody moiety of the ADC after isolation and before analysis of the structure of said ADC prevents ADC dissociation. The introduction of a reduction step leads to only two populations of 25 and 50 kDa fragments which can be used to calculate the DAR.

Thus, in a preferred embodiment, the method of the invention comprises a further step of reducing the ADC after isolation. According to this embodiment, the invention relates to a method for analysing the structure of an ADC present in a biological sample of a subject, said method comprising the steps of:
  a) contacting said biological sample with a reagent binding specifically the Fc domain of the antibody moiety of the ADC;
  b) isolating the ADC molecules bound by said reagent;
  c) reducing the ADC isolated in step b); and
  d) analysing the structure of the ADC of step c).

As explained above, in a first embodiment, the biological sample is a sample which was taken from a subject, wherein said subject is a subject to whom said ADC was previously administered. Alternatively, the biological sample is a sample of the subject which was previously added with said ADC. Such an embodiment may be useful for assessing the stability of an ADC in e.g., plasma, without actually administering said ADC to the subject.

In a preferred embodiment, analysing the structure of the ADC in step d) involves determining the DAR of said ADC.

Preferably, the reduction reaction of step c) is a reduction of the disulfide bonds of the antibody moiety of the ADC isolated in step b). Any type of disulfide bond reducing agent known to the person skilled in the art can be used. Such agents include in particular, dithiothreitol (DTT), beta-mercaptoethanol, 2-aminoethanethiol, cysteine hydrochloride, Tris (2-carboxyethyl) phosphine, Tris (2-carboxyethyl) phosphine hydrochloride, etc. Such reagents have been widely used in biochemistry laboratories for at least 50 years. The skilled person will therefore be capable of determining adequate reaction conditions for the reduction of the method of the invention without any problem and such conditions need not be further detailed.

It will immediately be clear to the person of skills in the art that the method of the invention allows the monitoring of the stability of an ADC in a biological sample to which said ADC has been added or in a subject who has been injected with said ADC.

Thus, in another aspect, the invention provides a method for assessing the stability of an ADC, comprising the steps of:
  a) determining a first DAR for the ADC in a first biological sample using any of the methods described above;
  b) determining a second DAR for the ADC in a second biological sample using any of the methods described above;
  c) comparing said first DAR and said second DAR; and
  d) assessing the stability of said ADC based on the comparison of step c).

The inventors have previously shown that the in vitro behaviour of an ADC added to a biological sample faithfully reproduces the in vivo degradation of said ADC. Thus, the method of the invention is particularly useful for assessing the stability of an ADC. According to this embodiment, the first biological sample of step a) and the second biological sample of step b) are identical, and the method comprises a prior step of adding said ADC to said biological sample.

Thus, the method according to this embodiment is a method for assessing the stability of an ADC in a biological sample, comprising the steps of:
  a) determining a first DAR for the ADC in said biological sample at a first time point using any of the methods described above;
  b) determining a second DAR for the ADC in said biological sample at a second time point using any of the methods described above;
  c) comparing said first DAR and said second DAR; and
  d) assessing the stability of said ADC based on the comparison of step c).

Preferably, the first DAR and the second DAR are determined at different time points. More preferably, the first DAR is determined before the second DAR. In this case, a second DAR which is smaller than the first DAR indicates that at least one molecule of ADC has been dissociated.

The method of the invention is also particularly advantageous as it enables monitoring the stability of an ADC in a subject. For example, such a method can be useful for adapting the treatment of a patient in need thereof.

Thus, according to this specific embodiment, the invention provides a method for assessing the stability of an ADC in a subject who has been injected with said ADC, said method comprising the steps of:
  a) determining a first DAR for the ADC in a first biological sample of said subject using any of the methods described above;
  b) determining a second DAR for the ADC in a second biological sample of said subject using any of the methods described above;
  c) comparing said first DAR and said second DAR; and
  d) assessing the stability of said ADC based on the comparison of step c).

Preferably, the first biological sample and the second biological sample are taken from the subject at different time points. More preferably, the first biological sample is taken before the second biological sample. In this case, a second DAR which is smaller than the first DAR indicates that at least one molecule of ADC has been dissociated.

In this context, the method of the invention is particularly useful for monitoring the stability of an ADC in a subject and adapting consequently the treatment of said subject. For example, if the degradation rate of said ADC in said patient is higher than a control degradation rate, there is a risk that the amount of ADC reaching its target in the subject may be too low. As a result, the efficiency of the treatment would be lower than expected. In this case, the adaptation of the treatment may consist in the continuation or an augmentation of said treatment, such as e.g. the administration of a further dose of said ADC. In another embodiment, when the degradation rate of said ADC in said patient is lower than a control degradation rate, the amount of ADC remaining in the bloodstream of the subject may be substantially higher than in healthy subjects, potentially leading to side effects. Thus, in such a case, the adaptation of said treatment may consist in the reduction or suppression of said treatment.

Packaged materials comprising a combination of reagents in predetermined amounts with instructions for performing the method described above, e.g. kits, are also within the scope of the invention. The kit contains the reagents for binding and isolating an ADC in a biological sample. As explained above such reagents are reagents specific for the Fc domain of the antibody moiety of the ADC. Said reagent may be provided attached to a solid support, e.g., beads or a plaque. The kit may further contain a disulfide bond reducing agent, such as one listed above. In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first Fc-specific reagent bound to a solid support. A second container may contain a disulfide bond reducing agent, in lyophilized form or in solution. The label or package insert may provide a description of the composition as well as instructions for the intended in vitro or diagnostic use.

Other characteristics and advantages of the invention appear in the continuation of the description with the examples and the figures whose legends are represented below.

LEGEND OF THE FIGURES

Figure 1B:
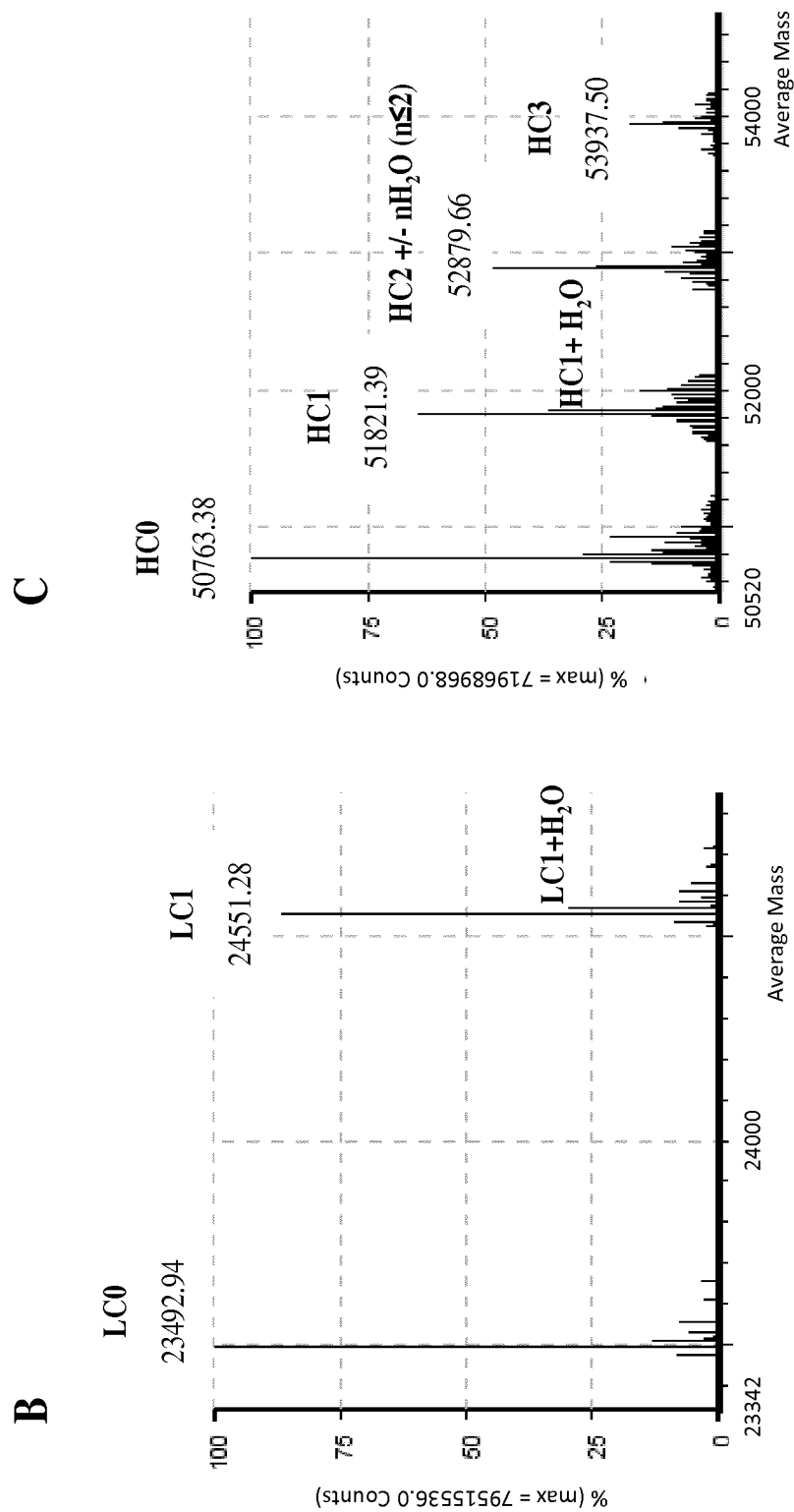

FIG. 1: Separation of ADC1 fragments obtained after immunoprecipitation from serum and reduction using a PLRP-S column and MS detection (A). Deconvoluted spectra of LC0, LC conjugated to 1 payload (LC1) (B) and HC0, HC conjugated to 1, 2 and 3 payloads (HC1, HC2 and HC3, respectively) (C)

FIG. 2: In vitro evolution of ADC1 fragments in sera from mice (A), rat (B) and cynomolgus monkey (C). ADC1 was spiked in serum at 100 µg/mL and incubated at 37° C. for 11 days. Aliquots were taken at the indicated time points, ADC was immunoprecipitated, reduced and analysed by LC-MS. Comparison of the mean DAR evolution versus time in the 3 different sera (D). The experiment was done in triplicate Error bars indicate SD.

Figure 3A:
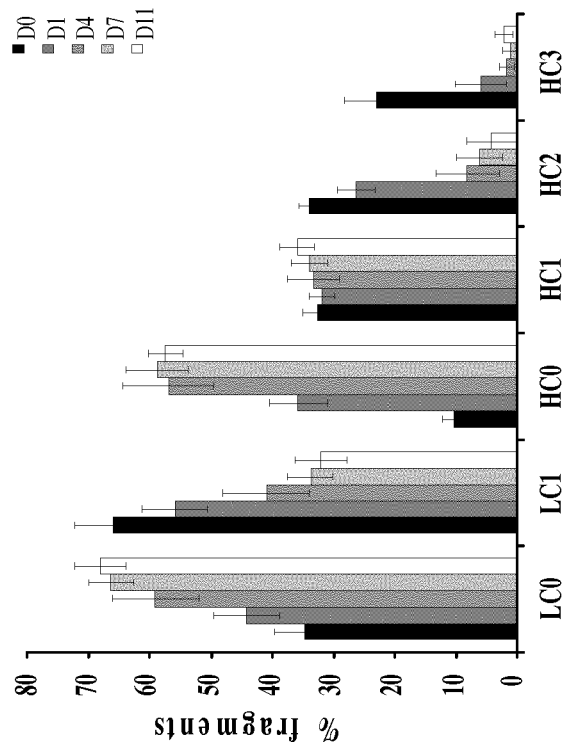
Figure 3A:
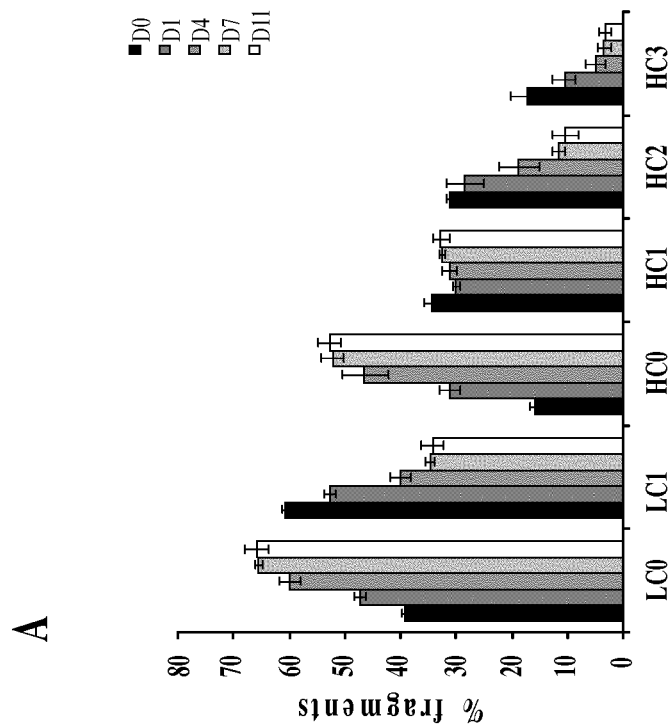
Figure 3B:
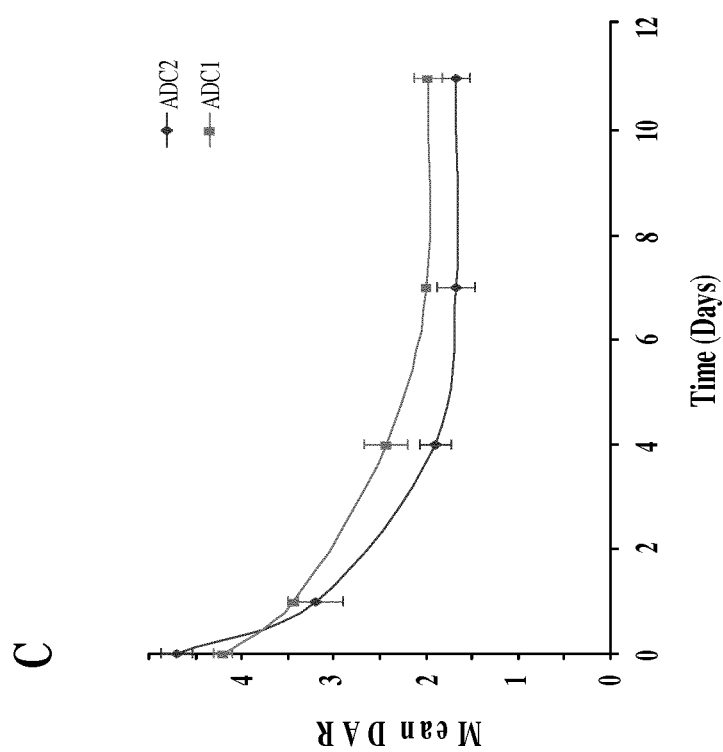

FIG. 3: In vitro stability studies of ADC1 (A) and ADC2 (B) in cynomolgus monkey serum by LC-MS ADC1 and ADC2 were spiked in cynomolgus serum at 100 µg/mL and incubated at 37° C. for 11 days. Aliquots were taken at the indicated time points, ADCs were immunoprecipitated, reduced and analysed by LC-MS. Comparison of the average DAR evolution versus time for the two ADCs (C). The experiment was done in triplicate. n=6; Error bars indicate SD.

Figure 4:
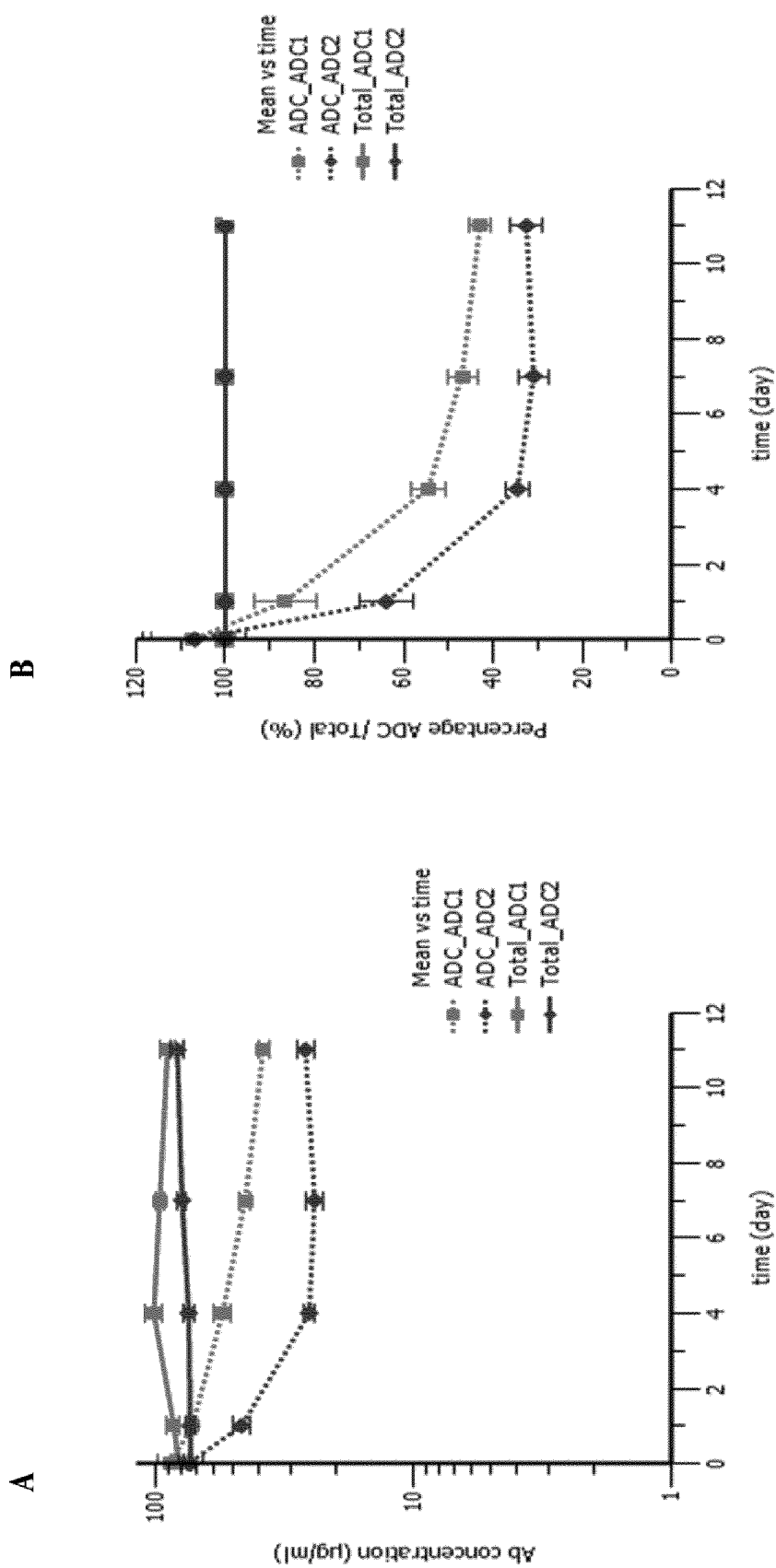

FIG. 4: In vitro stability data of ADC1 and ADC2 in cynomolgus monkey serum by ELISA. ADC1 and ADC2 were spiked in cynomolgus serum at 100 µg/mL and incubated at 37° C. for 11 days. Graph representing the concentrations of total Ab and ADCs were plotted versus the incubation time in days for both ADC1 and ADC2 (A). Data were normalized in percentage of the total Ab concentration at each time point. The percentages total Ab (100%) and ADCs were plotted versus the incubation time in days. n=6 (B); Error bars indicate SE.

FIG. 5: In vitro evolution of ADC1 fragments in sera from mice (A), rat (B) and cynomolgus monkey (C). ADC1 was injected at 5 mg/kg. Aliquots were taken at the indicated time points, ADC was immunoprecipitated, reduced and analysed by LC-MS. The experiment was done in triplicate. Error bars indicate SD.

Figure 6:
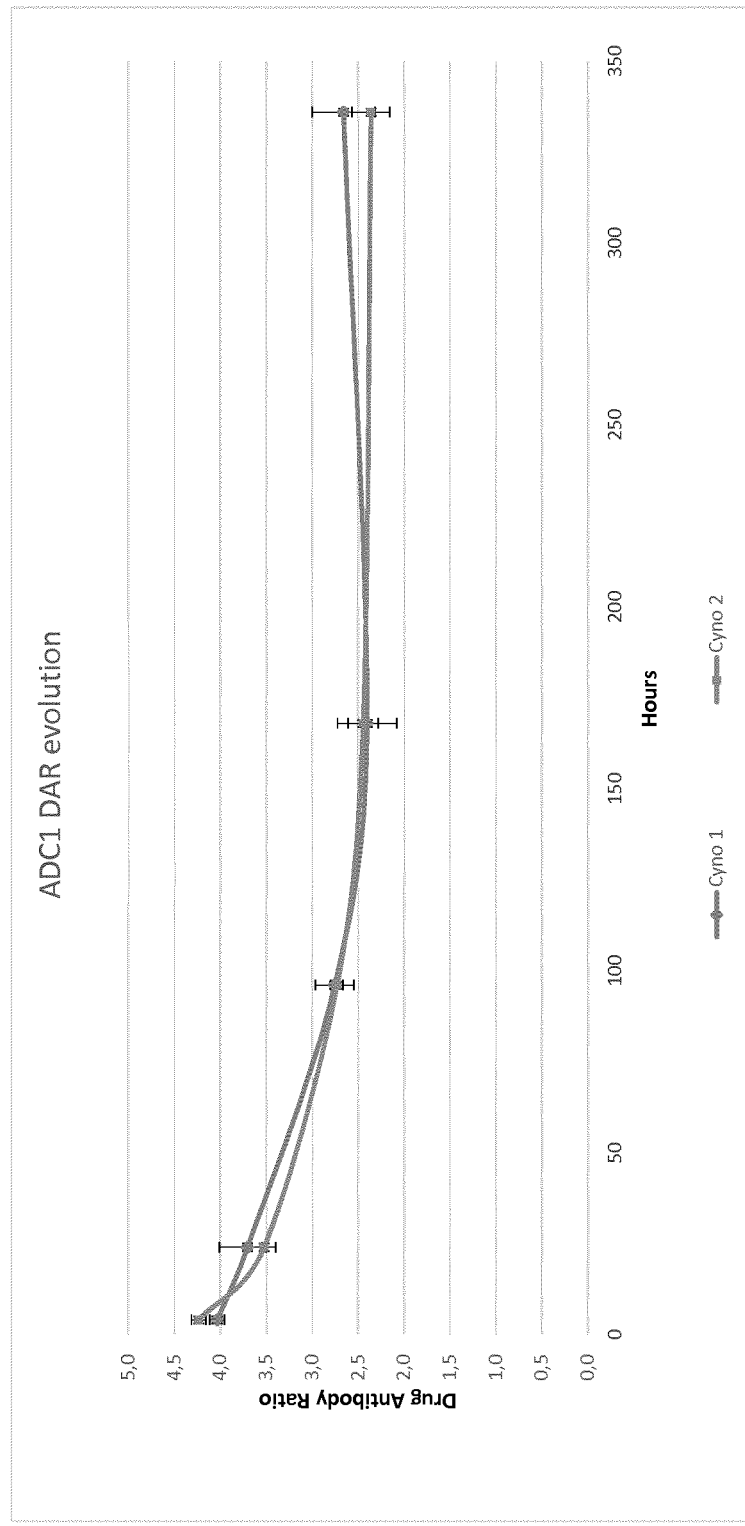

FIG. 6: Comparison of the DAR evolution in function of time in the 2 different Monkeys (Cyno 1 and Cyno 2). The experiment was done in triplicate. Error bars indicate SD.

Figure 7:
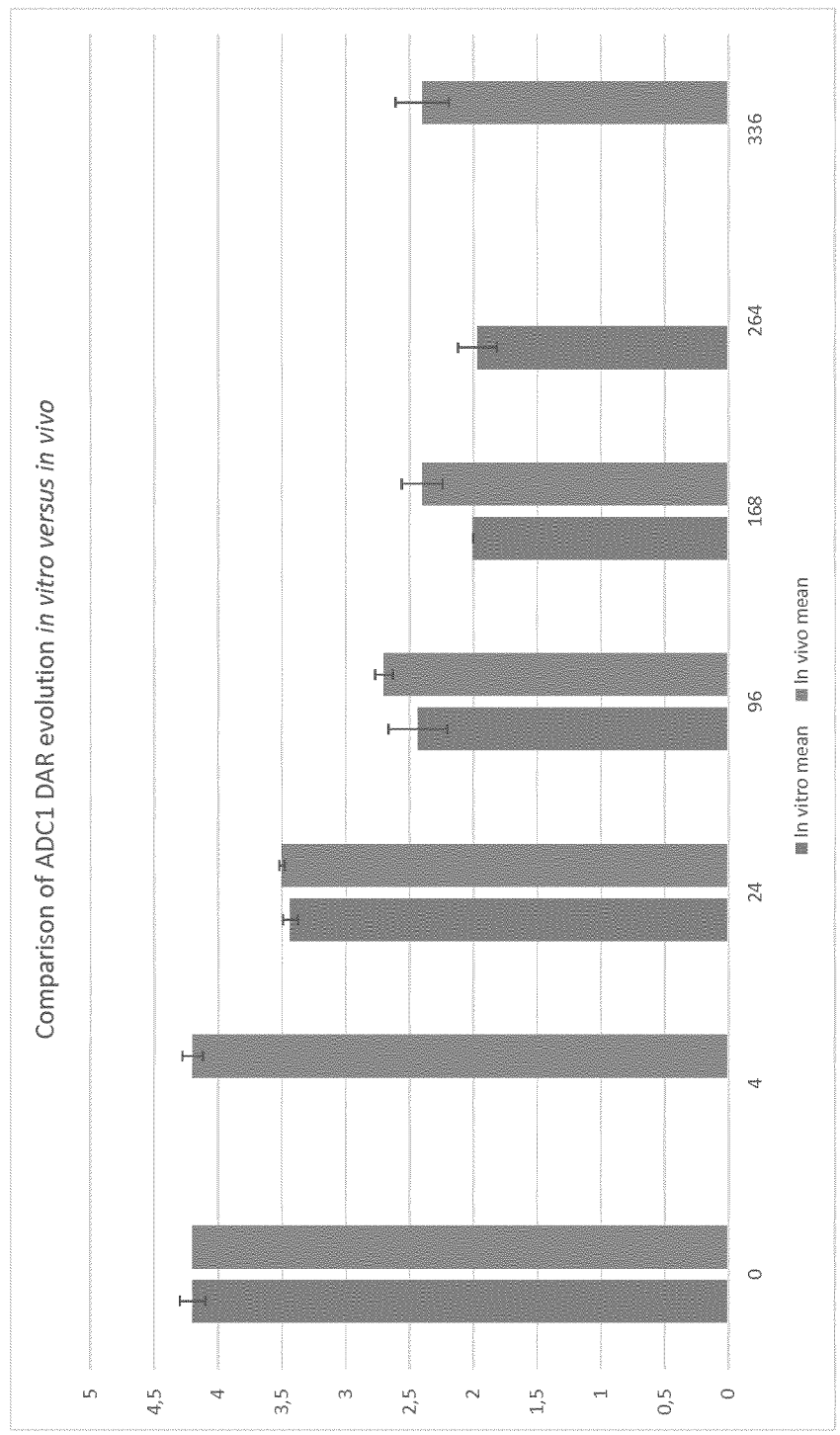

FIG. 7: Comparison of the mean DAR evolution in function of time in in vitro experiments (cynomolgus monkey serums, values of FIG. 3 C) and in vivo experiments (cynomolgus monkeys, values of FIG. 6). Error bars indicate SD.

EXAMPLES

Materials and Methods
Reagents and Materials

To prepare ADC1 and ADC2 conjugated at native cysteines with an average of four drugs per antibody, humanized mAbs were partially reduced and conjugated to maleimide-vc-auristatins (cleavable and non-cleavable linkers, two different auristatins) as previously described[18].

More particularly, ADC1 is an ADC targeting IGF-1R described in the examples of the application WO 2015/162291. ADC2 is Brentuximab vedotin (INN, trade name Adcetris), an ADC targeting CD30.

Cynomolgus (*Macaca fascicularis*) and rat (Sprague Dawley) sera were obtained from Bioprim (Perpignan, France) and mouse serum from athymic nude (Charles River Laboratories). CaptureSelect™ Human IgG-Fc PK Biotin conjugate was purchased from Life Technologies (Saint Aubin, France) and Dynabeads M-280 Streptavidin from Invitrogen (Saint Aubin, France). Guanidin hydrochlorid, Ethylenediaminetetraacetic acid (EDTA), Hydroxide sodium (NaOH), Trizma Base (Tris), Trifluoroacetic acid (TFA) and Sodium dihydrogen phosphate were obtained from Sigma-Aldrich (Saint-Quentin-Fallavier, France), acetonitrile (ACN) from Merck (Fontenay-sous-Bois, France) and Dithiothreitol (DTT) from Agilent Technologies (Les Ulis, France). Sodium chloride and Sodium phosphate dibasic were purchased from VWR (Fontenay-sous-Bois, France), HEPES and HBS-EP buffers from GE Healthcare (Vélizy-Villacoublay, France) and PBS from Biochrom (Fontenay-sous-Bois, France). All the aqueous solutions were prepared using ultra-pure water.

ADC Stability Study

ADCs were spiked in sterile mouse, rat or cynomolgus serum at a concentration of 100 µg/ml. Aliquots of 100 µl were incubated at +37° C. in Protein LoBind Tube (Eppendorf, Montesson, France). At specific times (day 1, day 4, day 7 and day 11) samples were removed from the oven and stored at −20° C. until sample processing and analysis.

ADC Samples Treatment for LC-MS Assay

ADCs were immunoprecipitated from sera using the following protocol. Briefly, 100 µl M-280 Streptavidin magnetics beads suspension were washed three times with HBS-EP buffer (0.01 M HEPES pH 7.4, 0.15 M NaCl, 3 mM EDTA, 0.005% v/v Surfactant P20) and incubated for 30 min at RT with the CaptureSelect™ Human IgG-Fc PK Biotin conjugate. Serum samples from stability studies were then added to the beads and incubated for 2 h at RT. After washing steps with HBS-EP buffer and HBS buffer (10 mM HEPES, 150 mM NaCl, 3 mM EDTA pH 7.6), the ADC was eluted with 0.4% TFA in water. After freeze drying, the samples were reconstituted and incubated with 34 mM DTT in denaturing buffer (6 M Guanidine, 0.1 M Tris, 2 mM EDTA pH 8.0) for 45 min at 56° C.

Acetic acid was then added to quench the reaction and samples were analysed by LC-MS.

LC-MS Analysis

Reverse phase separation was performed on an ultra-high performance liquid chromatography (UHPLC) system (Acquity UPLC H-Class Bio system, Waters) coupled to a Synapt G2si mass spectrometer, instrument control was performed using MassLynx® software (Waters).

The reduced samples were directly injected on a PLRP-S column (2.1×150 mm 8 µm, 1000 Å, Agilent) heated at 80° C. with a flow rate of 0.5 ml/min. Elution was performed with water as eluent A and acetonitrile as eluent B, both containing 0.05% TFA. The following elution gradient was applied, B was raised from 30% to 45% in 13 min and then from 45% to 95% in 2 min. The column was washed using 95% B and equilibrated using 30% B for 10 min. The autosampler temperature was set at 10° C. The mass spectrometer was operated in positive mode and data were recovered from m/z 500 to 3000 with voltages of 2.5 kV and 45 V for capillary and sample cone, respectively. The source and desolvation temperatures were set at 100° C. and 300° C., respectively.

Data Processing

Data were analysed using Biopharmalynx™ (Waters) software. Two representative time windows in the total ion chromatogram were selected to extract the corresponding mass spectrum of the LC fragments (LC, [LC+1 payload], [LC+1 payload+18 Da]) and HC fragments (HC, [HC+1 payload], [HC+1 payload+18 Da], [HC+2 payloads], [HC+2 payloads+18 Da], [HC+2 payloads+36 Da] and HC+3 payloads). Deconvolution was performed by MaxEnt™ to obtain the distribution profile of the different drug-loaded fragments. The MS peak area for each fragment was then used to calculate the average Drug to Antibody Ratio (DAR) using the following formula:

$$\text{Average } DAR = 2\left[\sum_{n=0}^{1}\left[nA_{LCn}/\sum_{n=0}^{1}(A_{LCn})\right] + \sum_{n=0}^{3}\left[nA_{HCn}/\sum_{n=0}^{3}(A_{HCn})\right]\right],$$

with A=peak area, n=loaded drug, LC=Light Chain and HC=Heavy Chain

Total Antibody and ADC ELISAs

Four different Ligand Binding Assay (LBAs) systems were used to determine Total Ab or ADC concentrations for ADC1 and ADC2[19]. More precisely, an antigen-specific assay was used for ADC1 and a universal method for ADC2. For the ADC quantification, specific anti-drugs were used relevant to the payload of the ADC.

Briefly, standard microtiter plates (MSD, Gaithersburg, USA) were coated at a concentration of 2 µg/ml Goat anti Human IgG, Monkey adsorbed antibody (SouthernBiotech) for Total Ab or of 3 µg/ml mouse monoclonal antibody raised against the payloads (Epitope Diagnostic Inc.) for ADC assays in PBS. After an overnight incubation at 4° C., plates were treated with blocking buffer (3% MSD Blocker A (MSD, Gaithersburg, USA)) for 1 h at 37° C. In parallel, the standard curves (1000 ng/ml-0.488 ng/ml) using reference immunoconjugates (ADC1 or ADC2) were prepared in assay buffer (1% MSD Blocker in TBS+0.02% Tween 20). Serum samples were diluted to 1:1000 or 1:5000 in a separate 2-ml deep 96-well polypropylene plate in MSD assay buffer. Standards and samples were then loaded onto the assay plate and incubated for 1 h at 37° C. After washing with 1×PBS, the detection step was done using a 2.5 µg/ml solution of the biotinylated antigen for the ADC1 (in house preparation) or a goat anti-human Ig Kappa sulfo-tag solution (in house preparation) diluted to 1 µg/ml in assay buffer for ADC2. After a 30-min incubation at 37° C., and a washing step, the detection was allowed by adding 150 µl of a 2×MSD-read T buffer containing surfactant (MSD, Gaithersburg, USA) just before reading using MSD Sector Imager.

Results

LC-MS Distribution Profile of ADC Fragments

The LC-MS analysis of reduced ADC1 (FIG. 1A) resulted in six major peaks as identified by Lyon R P et al[11,20]. The deconvoluted mass spectra of the six peaks for ADC1 reported in FIGS. 1B (for LC) and 1C (for HC) showed masses of 23492.9 Da and 24551.3 Da that matched with LC0 (MTheo=23493.2 Da) and LC+1 payload (MTheo=24551.6 Da) and masses of 50763.4 Da, 51821.4 Da, 52879.7 Da and 53937.5 Da that matched with HC0 (MTheo=50763.3 Da), HC+1 payload (MTheo=51821.7 Da), HC+2 payloads (MTheo=52880.0 Da), HC+3 payloads (MTheo=53938.4 Da). We also measured for each loaded-fragment, peaks with an increment of mass of +18 Da (for LC1, HC1) and +32 Da for HC2, matching with maleimide hydrolysis as already described by Shen et al[21]. The same types of results were also obtained for ADC2 (data not shown).

Figure 2A:
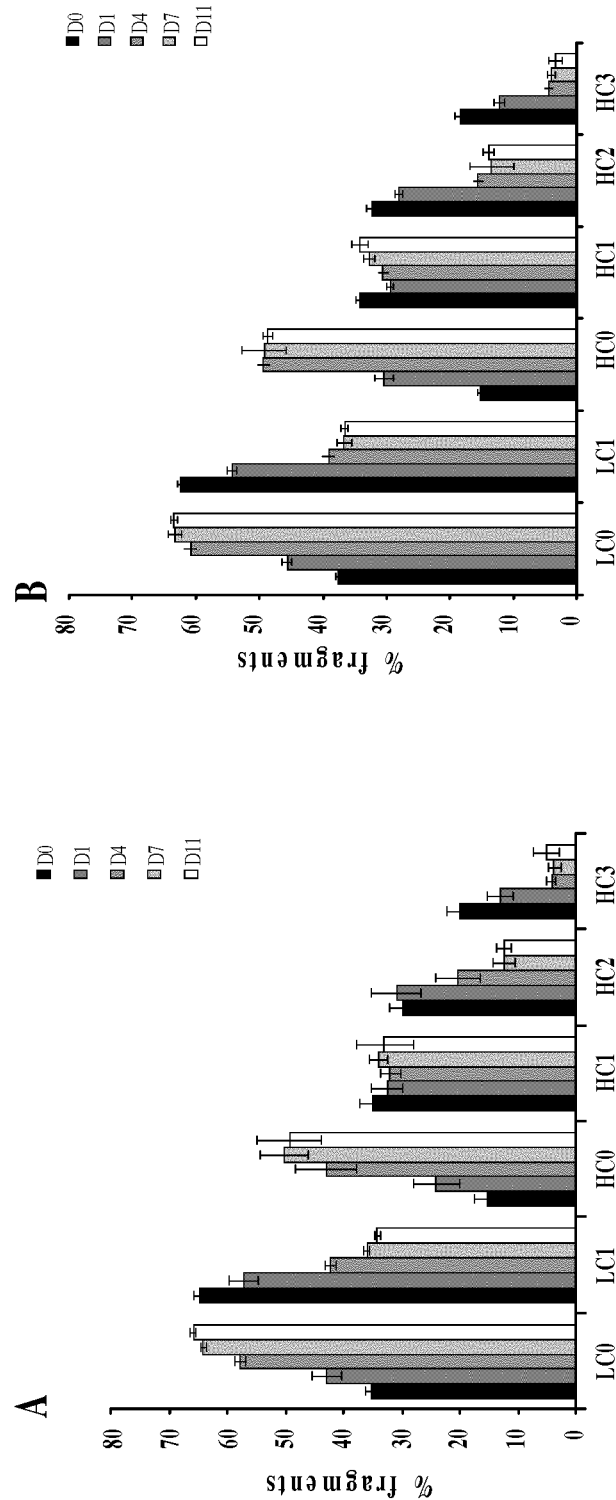
Figure 2B:
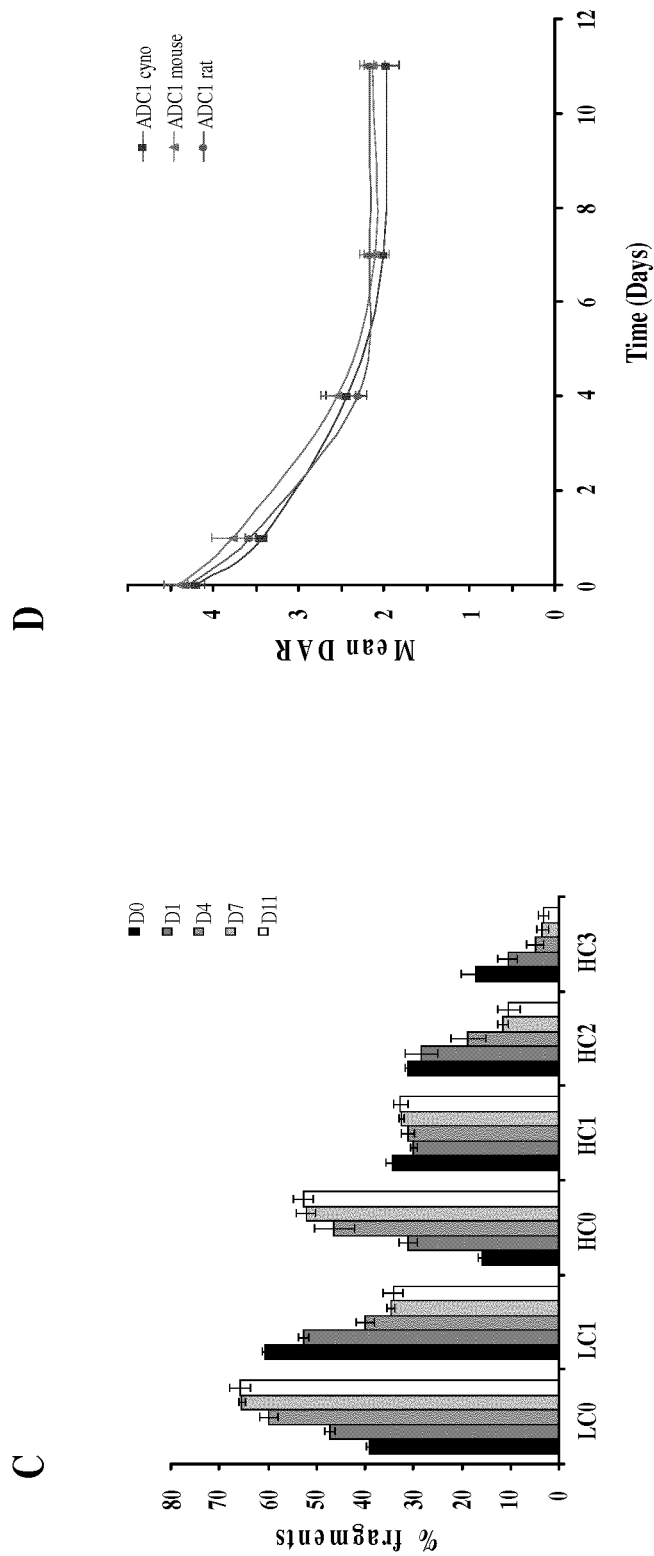

Stability of ADC1 in Sera from Mouse, Rat and Cynomolgus Monkey by LC-MS Analysis ADC1 was spiked in sera from mouse, rat and cynomolgus monkey at +37° C. The ADC was recovered by immunoprecipitation with the CaptureSelect™ Human IgG-Fc PK Biotin conjugate at different time points and analysed by LC-MS after reduction, to characterize the evolution of the different ADC fragments. In mouse serum (FIG. 2A), the LC and HC without payload (LC0 and HC0, respectively) increased from D0 to D4 and then were stabilized. This was correlated with the hydrolysis of the maleimide function of the payload preventing its further deconjugation in serum as reported by several groups[22-25]. Conversely, the fragments LC1, HC2 and HC3 decreased from day 0 to day 4 and then were stabilized. The HC1 fragment remained globally at the same level because its own deconjugation was offset by the ones of HC2 and HC3. The same deconjugation profile for ADC1 was observed in the serum from rat (FIG. 2B) and from cynomolgus monkey (FIG. 2C).

The average DAR evolution in serum from mice, from rat and cynomolgus is summarized in FIG. 2D. It decreased similarly in the three types of sera from DAR 4 at day 0 to DAR 2.5 at day 4 and then remained stable (around DAR 2) along the days 4 to 11. These data are in accordance with what is described in literature for a maleimide linker-based ADC, the mechanism of drug release from maleimide adducts likely involves a retro-michael reaction that takes place in serum as discussed above.

Comparison of the Stability of Two ADCs In Vitro in Cynomolgus Monkey Serum by LC-MS and ELISA The ADC1 and ADC2 were spiked (at 100 µg/µL) in cynomolgus serum and incubated at 37° C. for 11 days. Samples were analysed at different time points using both LC-MS analysis for the average DAR evaluation after immunoprecipitation with the CaptureSelect™ Human IgG-Fc PK Biotin conjugate, and sandwich ELISA-based methods for quantification of total Abs and ADCs[26].

The analyses of ADCs by LC-MS, at the indicated time points showed that fragments profiles for ADC1 (FIG. 3A) and ADC2 (FIG. 3B) were similar. The average DAR evolution decreased from DAR 4 and 4.5 at day 0, to DAR 2.5 and 2.0 at day 4 for ADC1 and ADC2, respectively and then was stable along the days 4 to 11 (FIG. 3C).

The amount of total antibody and ADC, in serum samples was evaluated in parallel by a quantitative sandwich ELISA. The total antibody assay detects both naked and conjugated antibody, whereas the ADC assay detects only antibody linked at least to one payload.

FIG. 4A clearly shows that in cynomolgus serum, the total Ab level (~100 µg/ml) remained stable over the 11-day period, for both ADC1 and ADC2. In contrast, the ADC concentration decreased during this period for both ADC1 and ADC2. The normalization of the data against the total Ab concentration at each time point (FIG. 4B) emphasizes that the ADC level decreased mainly during the four first days for both ADC1 and ADC2. Thereafter the ADC concentration tended to remain stable over the 7 following days. These data are correlated with those obtained by the LC-MS analysis, confirming that deconjugation occurs mainly during an initial 4-day period. The diminution of the ADC level by ELISA reflects the appearance of DAR0, however, no information relative to the average DAR is available, in contrast to the LC-MS method.

CONCLUSION

In this study, we present a new universal method to immunocapture and analyse by LC-MS the stability of ADCs in sera from preclinical species. Using a single protocol for samples preparation allows the stability study of ADCs in sera from mouse, rat and cynomolgus monkey. Furthermore, we demonstrated that this type of protocol can be applied to different ADCs, the results obtained in cynomolgus serum using immunoprecipitation with the CaptureSelect™ Human IgG-Fc PK Biotin conjugate and LC-MS analysis were validated using an ELISA orthogonal method. To summarize, as the ligand used for immunoprecipitation is targeting the Fc part of mAb, this protocol can be applied to compare and analyse the stability of virtually all ADCs and mAbs in sera for preclinical studies without the need to prepare specific tools. To our knowledge, this is the first time that this type of sample preparation coupled to LC-MS analysis is described to characterize DAR evolution for ADC in vitro stability studies. Finally, additional experiments show that this method can also be used to study the DAR evolution and the payload [11] localisation after the ADC administration in vivo.

A particular embodiment of the invention consists of the implementation of a reduction step before the MS analysis.

A particular embodiment of the invention consists of the use of HBS-EP/HBS as washing buffer.

A particular embodiment of the invention consists of the use of magnetic beads as support for the capture of the agent anti human Fc (such as for example CaptureSelect™ Human IgG-Fc immobilization).

Differentiation Elements Between mAb (ThermoFisher Protocol) and ADC (CIPF Protocol) Immunoprecipitation

|  | Thermo (mAb) | CIPF (ADC) |
|---|---|---|
| Support for CaptureSelect ™ Human IgG-Fc immobilization | MSIA | Magnetic beads |
| Washing buffer | PBS or Hepes | HBS-EP/HBS |
| Reduction before MS analysis | None | Yes : to simplify the number of molecules to be analysed |

Washing Steps:

The HBS-EP buffer (0.01 M HEPES pH 7.4, 0.15 M NaCl, 3 mM EDTA, 0.005% v/v Surfactant P20) was used instead of PBS because it contains a surfactant molecule which allows the elimination of plasma proteins non-specifically adsorbed on support.

The further washing step with HBS alone was introduced to remove the surfactant P20, not compatible with mass analysis.

Reduction Step:

This step was introduced because elution of the ADC (the drugs are conjugated on the sulfhydryl groups of the interchain cysteine residues) induces the ADC dissociation. The generated fragments have different molecular weights comprised between 25 and 150 KDa with different mass response factors, which not allows the determination of the % of each species used to calculate the drug to antibody ratio (DAR).

The introduction of the reduction step leads to only two populations of 25 and 50 KDa fragments used to calculate the DAR in order to follow the ADC de-conjugation in sera and to characterize precisely the cleavage and modification of the payloads.

This reduction step would also allow a more precise determination of the DAR evolution for ADCs with drugs conjugated on the amine groups of the lysine residues in sera, because without reduction, the highly-conjugated species would be underestimated.

In Vivo Stability of ADC1 in Cynomolgus Monkey (Male *Macaca fascicularis*) by LC-MS Analysis The ADC1 was administrated to two cynomolgus monkeys at doses of 5 mg/kg by intravenous route. Blood samples were collected before ADC injection and after 4, 24, 96, 168 and 336 hours following the injection. Samples sera were stored at −80° C.

Figure 5A:
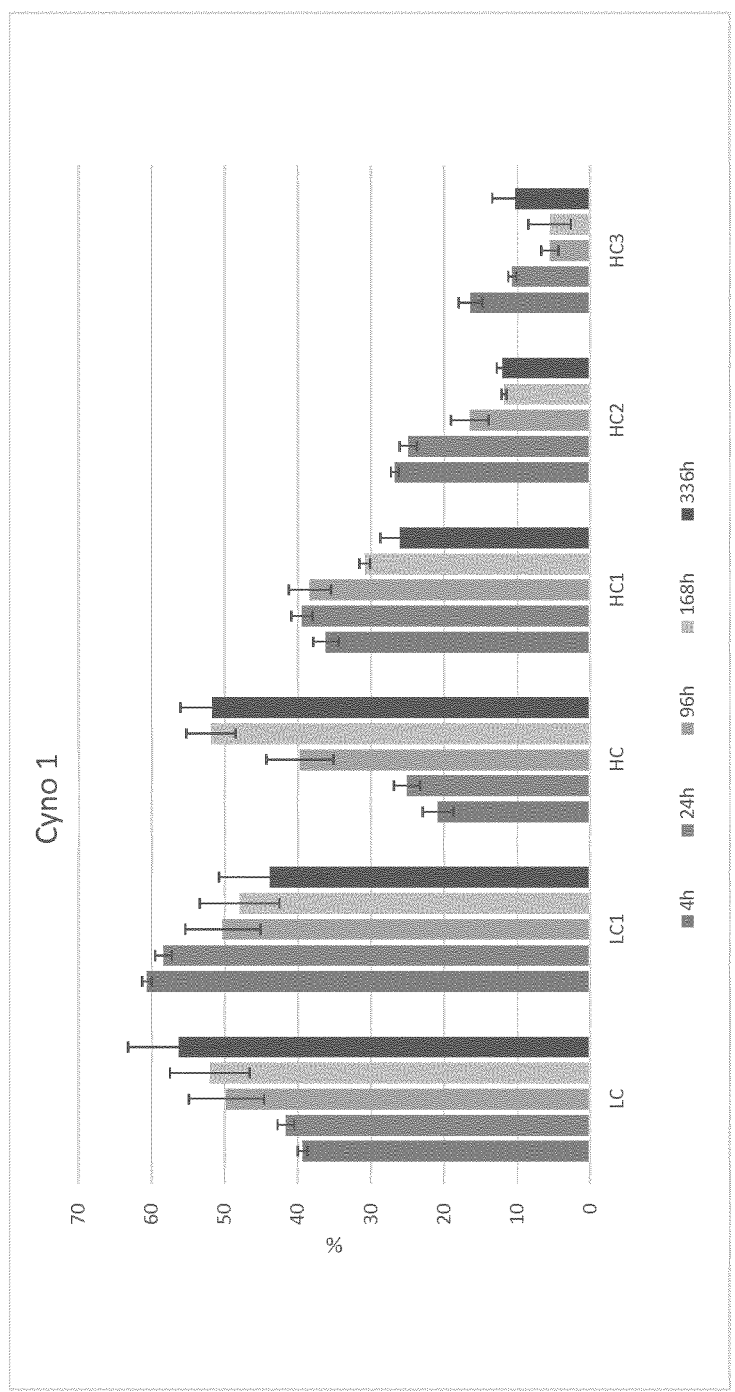
Figure 5B:
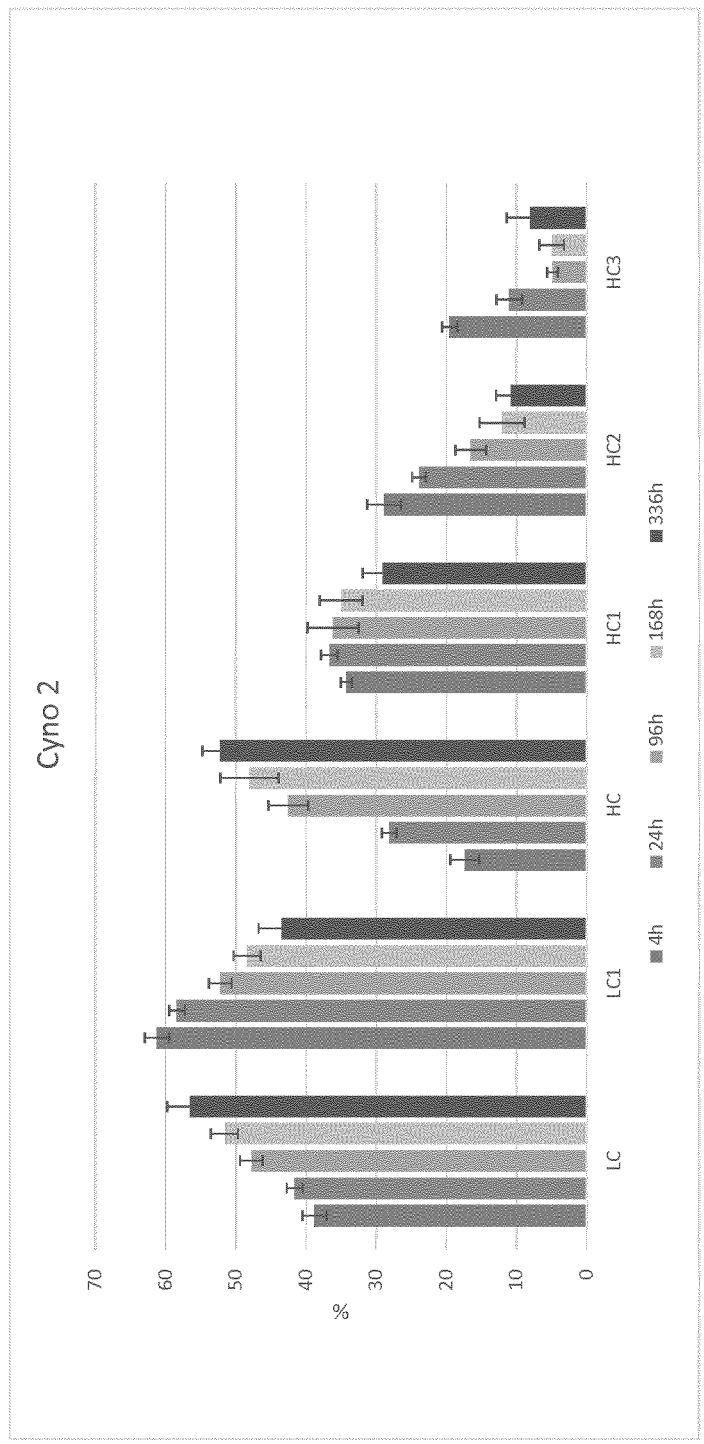

The ADC was recovered by immunoprecipitation (from both cynomolgus monkey sera) with the CaptureSelect™ Human IgG-Fc PK Biotin conjugate at different time points and analysed by LC-MS after reduction, to characterize the evolution of the different ADC fragments (FIGS. 5A and 5B). The LC and HC without payload (LC0 and HC0, respectively) increased from 4 H to 336 H. Conversely, LC1 and HC2 fragments decreased, HC1 increased until 96 H and then decreased.

The average DAR evolution is summarized in FIG. 6. It decreased similarly in both monkeys, from DAR 4 at day 0 to DAR 2.5 at day 7 and then remained stable (around DAR 2.5) from day 7 to day 14. These data are in accordance with what is described in literature for a maleimide linker-based ADC.

In Vivo and In Vitro ADC Serum Stability Comparison

As shown in FIG. 7, the in vivo ADC deconjugation profile in serum is similar to the one obtained in vitro. It decreased similarly from DAR 4 at day 0 to DAR 2.5 at day 7 and then remained stable from day 7 to day 14. No DAR evolution was observed between 7 and 14 days, which could be interpreted as the stabilisation effect of the succinimide ring opening described for similar linkers).

REFERENCES

[1] Beck, A. and Reichert, J. M., Antibody-drug conjugates: present and future. MAbs., 6 (2014) 15.

[2] Beck, A., Terral, G., Debaene, F., Wagner-Rousset, E., Marcoux, J., Janin-Bussat, M. C., Colas, O., Van Dorsselaer, A., and Cianferani, S., Cutting-edge mass spectrometry methods for the multi-level structural characterization of antibody-drug conjugates. Expert. Rev. Proteomics., (2016) 1.

[3] Beck, A., Haeuw, J. F., Wurch, T., Goetsch, L., Bailly, C., and Corvaia, N., The next generation of antibody-drug conjugates comes of age. Discov. Med., 10 (2010) 329.

[4] Wiggins, B., Liu-Shin, L., Yamaguchi, H., and Ratnaswamy, G., Characterization of cysteine-linked conjugation profiles of immunoglobulin G1 and immunoglobulin G2 antibody-drug conjugates. J. Pharm. Sci., 104 (2015) 1362.

[5] Chari, R. V., Miller, M. L., and Widdison, W. C., Antibody-drug conjugates: an emerging concept in cancer therapy. Angew. Chem. Int. Ed Engl., 53 (2014) 3796.

[6] Klinguer-Hamour, C., Strop, P., Shah, D. K., Ducry, L., Xu, A., and Beck, A., World Antibody-Drug Conjugate Summit, Oct. 15-16, 2013, San Francisco, Calif. MAbs., 6 (2014) 18.

[7] Valliere-Douglass, J. F., McFee, W. A., and Salas-Solano, O., Native intact mass determination of antibodies conjugated with monomethyl Auristatin E and F at interchain cysteine residues. Anal. Chem., 84 (2012) 2843.

[8] Debaene, F., Boeuf, A., Wagner-Rousset, E., Colas, O., Ayoub, D., Corvaia, N., Van Dorsselaer, A., Beck, A., and Cianferani, S., Innovative native MS methodologies for antibody drug conjugate characterization: High resolution native MS and IM-MS for average DAR and DAR distribution assessment. Anal. Chem., 86 (2014) 10674.

[9] Birdsall, R. E., McCarthy, S. M., Janin-Bussat, M. C., Perez, M., Haeuw, J. F., Chen, W., and Beck, A., A sensitive multidimensional method for the detection, characterization, and quantification of trace free drug species in antibody-drug conjugate samples using mass spectral detection. MAbs, (2015) 1.

[10] Wakankar, A., Chen, Y., Gokarn, Y., and Jacobson, F. S., Analytical methods for physicochemical characterization of antibody drug conjugates. MAbs, 3 (2011) 161.

[11] Janin-Bussat, M. C., Dillenbourg, M., Corvaia, N., Beck, A., and Klinguer-Hamour, C., Characterization of antibody drug conjugate positional isomers at cysteine residues by peptide mapping LC-MS analysis. J. Chromatogr. B Analyt. Technol. Biomed. Life Sci., 981-982 (2015) 9.

[12] Beck, A., Wagner-Rousset, E., Ayoub, D., Van Dorsselaer, A., and Sanglier-Cianferani, S., Characterization of therapeutic antibodies and related products. Anal. Chem., 85 (2013) 715.

[13] Tibbitts, J., Canter, D., Graff, R., Smith, A., and Khawli, L. A., Key factors influencing ADME properties of therapeutic proteins: A need for ADME characterization in drug discovery and development. MAbs, (2015) 00.

[14] Marcoux, J., Champion, T., Colas, O., Wagner-Rousset, E., Corvaia, N., Van Dorsselaer, A., Beck, A., and Cianferani, S., Native mass spectrometry and ion mobility characterization of trastuzumab emtansine, a lysine-linked antibody drug conjugate. Protein Sci., 24 (2015) 1210.

[15] Saber, H. and Leighton, J. K., An FDA oncology analysis of antibody-drug conjugates. Regul. Toxicol. Pharmacol., 71 (2015) 444.

[16] Hengel, S. M., Sanderson, R., Valliere-Douglass, J., Nicholas, N., Leiske, C., and Alley, S. C., Measurement of in vivo drug load distribution of cysteine-linked antibody-drug conjugates using microscale liquid chromatography mass spectrometry. Anal. Chem., 86 (2014) 3420.

[17] Sanderson, R. J., Nicholas, N. D., Baker Lee, C., Hengel, S. M., Lyon, R. P., Benjamin, D. R., and Alley, S. C., Antibody-conjugated drug assay for protease-cleavable antibodyGÇôdrug conjugates. Bioanalysis, 8 (2015) 55.

[18] Wagner-Rousset, E., Janin-Bussat, M. C., Colas, O., Excoffier, M., Ayoub, D., Haeuw, J. F., Rilatt, I., Perez, M., Corvaia, N., and Beck, A., Antibody-drug conjugate model fast characterization by LC-MS following IdeS proteolytic digestion. MAbs., 6 (2014) 173.

[19] Kaur, S., Xu, K., Saad, O. M., Dere, R. C., and Carrasco-Triguero, M., Bioanalytical assay strategies for the development of antibodyGÇôdrug conjugate biotherapeutics. Bioanalysis, 5 (2013) 201.

[20] Lyon, R. P., Meyer, D. L., Setter, J. R., and Senter, P. D., Conjugation of anticancer drugs through endogenous monoclonal antibody cysteine residues. Methods Enzymol., 502:123-38. doi: 10.1016/6978-0-12-416039-2.00006-9. (2012) 123.

[21] Shen, B. Q., Xu, K., Liu, L., Raab, H., Bhakta, S., Kenrick, M., Parsons-Reponte, K. L., Tien, J., Yu, S. F., Mai, E., Li, D., Tibbitts, J., Baudys, J., Saad, O. M., Scales, S. J., McDonald, P. J., Hass, P. E., Eigenbrot, C., Nguyen, T., Solis, W. A., Fuji, R. N., Flagella, K. M., Patel, D., Spencer, S. D., Khawli, L. A., Ebens, A., Wong, W. L., Vandlen, R., Kaur, S., Sliwkowski, M. X., Scheller, R. H., Polakis, P., and Junutula, J. R., Conjugation site modulates the in vivo stability and therapeutic activity of antibody-drug conjugates. Nat. Biotechnol., 30 (2012) 184.

[22] Alley, S. C., Benjamin, D. R., Jeffrey, S. C., Okeley, N. M., Meyer, D. L., Sanderson, R. J., and Senter, P. D., Contribution of linker stability to the activities of anticancer immunoconjugates. Bioconjug. Chem., 19 (2008) 759.

[23] Lyon, R. P., Setter, J. R., Bovee, T. D., Doronina, S. O., Hunter, J. H., Anderson, M. E., Balasubramanian, C. L., Duniho, S. M., Leiske, C. I., Li, F., and Senter, P. D., Self-hydrolyzing maleimides improve the stability and pharmacological properties of antibody-drug conjugates. Nat. Biotechnol., 32 (2014) 1059.

[24] Tumey, L. N., Charati, M., He, T., Sousa, E., Ma, D., Han, X., Clark, T., Casavant, J., Loganzo, F., Barletta, F., Lucas, J., and Graziani, E. I., Mild method for succinimide hydrolysis on ADCs: impact on ADC potency, stability, exposure, and efficacy. Bioconjug. Chem., 25 (2014) 1871.

[25] Fontaine, S. D., Reid, R., Robinson, L., Ashley, G. W., and Santi, D. V., Long-term stabilization of maleimide-thiol conjugates. Bioconjug. Chem., 26 (2015) 145.

[26] Xu, K., Liu, L., Dere, R., Mai, E., Erickson, R., Hendricks, A., Lin, K., Junutula, J. R., and Kaur, S., Characterization of the drug-to-antibody ratio distribution for antibodyGÇôdrug conjugates in plasma/serum. Bioanalysis, 5 (2013) 1057.

We claim:

1. A method for analysing the structure of an antibody-drug conjugate (ADC) present in a biological sample of a subject, wherein the ADC comprises an Fc domain of human origin, said method comprising the steps of:
a) contacting said biological sample with a reagent binding specifically the Fc domain of the antibody moiety of the ADC wherein the reagent binds an Fc domain of human origin, but not an Fc domain from any other species;
b) isolating the ADC molecules bound by said reagent;
c) reducing the ADC isolated in step b) with a reducing agent that allows reduction of the disulfide bonds of the antibody moiety of the isolated ADC, thereby preventing ADC dissociation; and
d) analysing the structure of the reduced ADC of step c).

2. The method of claim 1, wherein said subject is a subject previously administered with said ADC.

3. The method of claim 1, wherein said method comprises a preliminary step of adding said ADC to said biological sample.

4. The method of claim 1, wherein analysing the structure of the reduced ADC in step d) involves determining the drug-antibody ratio (DAR) of said reduced ADC.

5. The method of claim 1, wherein the structure of the reduced ADC is analysed in step d) by mass spectrometry.

6. The method of claim 1, wherein the ADC is a compound of formula (I):

Ab-(L-D)$_n$ (I)

or a pharmaceutically acceptable salt thereof,
wherein
Ab is an antibody, or an antigen binding fragment thereof, capable of binding to the human IGF-1R which comprises the three heavy-chain CDRs of sequence SEQ ID No. 1, 2 and 3 and the three light-chain CDRs of sequence SEQ ID No. 4, 5 and 6;
L is a linker;
D is a drug moiety of the following formula (II):

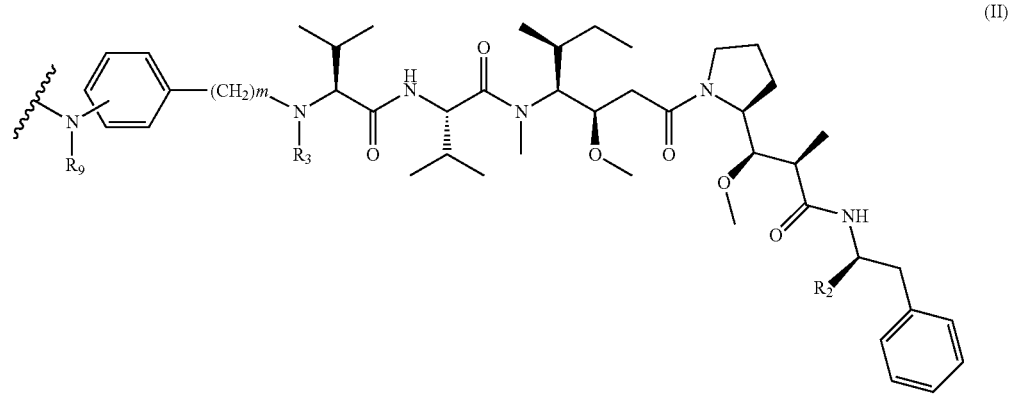

wherein:
  $R_2$ is COOH, COOCH$_3$ or thiazolyl;
  $R_3$ is H or (C$_1$-C$_6$)alkyl;
  $R_9$ is H or (C$_1$-C$_6$)alkyl;
  m is an integer comprised between 1 and 8;
  the wavy line indicates the point of attachment to L; and
  n is 1 to 12.

* * * * *

SEQUENCE LISTING

<160> NUMBER OF SEQ ID NOS: 81

<210> SEQ ID NO 1
<211> LENGTH: 8

```
<212> TYPE: PRT
<213> ORGANISM: artificial
<220> FEATURE:
<223> OTHER INFORMATION: Consensus CDR -H1
<220> FEATURE:
<221> NAME/KEY: MISC_FEATURE
<222> LOCATION: (3)..(3)
<223> OTHER INFORMATION: Thr may be replaced by Ser
<220> FEATURE:
<221> NAME/KEY: MISC_FEATURE
<222> LOCATION: (8)..(8)
<223> OTHER INFORMATION: Tyr may be replaced by Phe

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: artificial
<220> FEATURE:
<223> OTHER INFORMATION: Consensus CDR-H2

<400> SEQUENCE: 2

Ile Trp Pro Gly Asp Gly Ser Thr
1               5

<210> SEQ ID NO 3
<211> LENGTH: 13
<212> TYPE: PRT
<213> ORGANISM: artificial
<220> FEATURE:
<223> OTHER INFORMATION: Consensus CDR-H3

<400> SEQUENCE: 3

Ala Ser Pro Met Ile Thr Pro Asn Tyr Ala Met Asp Tyr
1               5                   10

<210> SEQ ID NO 4
<211> LENGTH: 6
<212> TYPE: PRT
<213> ORGANISM: artificial
<220> FEATURE:
<223> OTHER INFORMATION: Consensus CDR-L1
<220> FEATURE:
<221> NAME/KEY: MISC_FEATURE
<222> LOCATION: (4)..(4)
<223> OTHER INFORMATION: Ser may be replaced by Asn

<400> SEQUENCE: 4

Gln Asp Ile Ser Lys Tyr
1               5

<210> SEQ ID NO 5
<211> LENGTH: 3
<212> TYPE: PRT
<213> ORGANISM: artificial
<220> FEATURE:
<223> OTHER INFORMATION: Consensus CDR-L2

<400> SEQUENCE: 5

Tyr Thr Ser
1

<210> SEQ ID NO 6
<211> LENGTH: 9
<212> TYPE: PRT
<213> ORGANISM: artificial
```

```
<220> FEATURE:
<223> OTHER INFORMATION: Consensus CDR-L3
<220> FEATURE:
<221> NAME/KEY: MISC_FEATURE
<222> LOCATION: (5)..(5)
<223> OTHER INFORMATION: Thr may be replaced by Ala

<400> SEQUENCE: 6

Gln Gln Gly Ser Thr Leu Pro Tyr Thr
1               5

<210> SEQ ID NO 7
<211> LENGTH: 8
<212> TYPE: PRT
<213> ORGANISM: artificial
<220> FEATURE:
<223> OTHER INFORMATION: CDR-H1

<400> SEQUENCE: 7

Gly Tyr Thr Phe Thr Ser Tyr Tyr
1               5

<210> SEQ ID NO 8
<211> LENGTH: 8
<212> TYPE: PRT
<213> ORGANISM: artificial
<220> FEATURE:
<223> OTHER INFORMATION: CDR-H1

<400> SEQUENCE: 8

Gly Tyr Ser Phe Thr Ser Tyr Phe
1               5

<210> SEQ ID NO 9
<211> LENGTH: 6
<212> TYPE: PRT
<213> ORGANISM: artificial
<220> FEATURE:
<223> OTHER INFORMATION: CDR-L1

<400> SEQUENCE: 9

Gln Asp Ile Ser Lys Tyr
1               5

<210> SEQ ID NO 10
<211> LENGTH: 6
<212> TYPE: PRT
<213> ORGANISM: artificial
<220> FEATURE:
<223> OTHER INFORMATION: CDR-L1

<400> SEQUENCE: 10

Gln Asp Ile Asn Lys Tyr
1               5

<210> SEQ ID NO 11
<211> LENGTH: 9
<212> TYPE: PRT
<213> ORGANISM: artificial
<220> FEATURE:
<223> OTHER INFORMATION: CDR-L3

<400> SEQUENCE: 11

Gln Gln Gly Ser Thr Leu Pro Tyr Thr
1               5

<210> SEQ ID NO 12
```

```
<211> LENGTH: 9
<212> TYPE: PRT
<213> ORGANISM: artificial
<220> FEATURE:
<223> OTHER INFORMATION: CDR-L3

<400> SEQUENCE: 12

Gln Gln Gly Ser Ala Leu Pro Tyr Thr
1               5

<210> SEQ ID NO 13
<211> LENGTH: 120
<212> TYPE: PRT
<213> ORGANISM: artificial
<220> FEATURE:
<223> OTHER INFORMATION: c208F2, heavy chain, VH

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Lys Asp Lys Thr Thr Leu Thr Ala Asp Lys Ser Ser Asn Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 14
<211> LENGTH: 120
<212> TYPE: PRT
<213> ORGANISM: artificial
<220> FEATURE:
<223> OTHER INFORMATION: c212A11, heavy chain, VH

<400> SEQUENCE: 14

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120
```

```
<210> SEQ ID NO 15
<211> LENGTH: 120
<212> TYPE: PRT
<213> ORGANISM: artificial
<220> FEATURE:
<223> OTHER INFORMATION: c214F8, heavy chain, VH

<400> SEQUENCE: 15

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
        50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 16
<211> LENGTH: 120
<212> TYPE: PRT
<213> ORGANISM: artificial
<220> FEATURE:
<223> OTHER INFORMATION: c219D6, heavy chain, VH

<400> SEQUENCE: 16

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
        50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 17
<211> LENGTH: 120
<212> TYPE: PRT
<213> ORGANISM: artificial
<220> FEATURE:
<223> OTHER INFORMATION: c213B10, heavy chain, VH

<400> SEQUENCE: 17

Gln Val Gln Leu Gln Gln Ser Gly Ser Glu Leu Val Lys Pro Gly Ala
```

-continued

```
                 1               5                  10                 15
Ser Val Lys Met Ser Cys Lys Ala Ser Gly Tyr Thr Phe Thr Ser Tyr
                20                  25                 30

Tyr Ile His Trp Val Lys Gln Arg Pro Gly Gln Gly Leu Glu Trp Ile
            35                  40                 45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
                100                 105                110

Gly Ala Ser Val Thr Val Ser Ser
            115                 120
```

<210> SEQ ID NO 18
<211> LENGTH: 107
<212> TYPE: PRT
<213> ORGANISM: artificial
<220> FEATURE:
<223> OTHER INFORMATION: c208F2, light chain, VL

<400> SEQUENCE: 18

```
Asp Ile Gln Met Thr Gln Thr Thr Ser Ser Leu Ser Ala Ser Leu Gly
1               5                  10                 15

Asp Arg Val Thr Ile Ser Cys Arg Ala Ser Gln Asp Ile Ser Lys Tyr
            20                  25                 30

Leu Asn Trp Tyr Gln Gln Pro Asp Gly Thr Ile Lys Leu Leu Ile
            35                  40                 45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
                100                 105
```

<210> SEQ ID NO 19
<211> LENGTH: 107
<212> TYPE: PRT
<213> ORGANISM: artificial
<220> FEATURE:
<223> OTHER INFORMATION: c212A11, light chain, VL

<400> SEQUENCE: 19

```
Asp Ile Gln Met Thr Gln Thr Thr Ser Ser Leu Ser Ala Ser Leu Gly
1               5                  10                 15

Asp Arg Val Thr Ile Ser Cys Arg Ala Ser Gln Asp Ile Asn Lys Tyr
            20                  25                 30

Leu Asn Trp Tyr Gln Gln Pro Asp Gly Thr Val Lys Leu Leu Ile
            35                  40                 45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Ser Asn Leu Glu Gln
65                  70                  75                  80
```

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: artificial
<220> FEATURE:
<223> OTHER INFORMATION: c214F8, light chain, VL

<400> SEQUENCE: 20

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: artificial
<220> FEATURE:
<223> OTHER INFORMATION: c219D6, light chain, VL

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: artificial
<220> FEATURE:
<223> OTHER INFORMATION: c213B10, light chain, VL

<400> SEQUENCE: 22

Asp Ile Gln Met Thr Gln Thr Thr Ser Ser Leu Ser Ala Ser Leu Gly

```
                 1               5                  10                 15
Asp Arg Val Thr Ile Ser Cys Arg Ala Ser Gln Asp Ile Ser Lys Tyr
                20                  25                 30

Leu Asn Trp Tyr Gln Gln Pro Asp Gly Thr Ile Lys Leu Leu Ile
                35                  40                 45

Tyr Tyr Thr Ser Arg Leu His Ser Gly Val Pro Ser Arg Phe Ser Gly
                50                  55                 60

Arg Gly Ser Gly Thr Asp Tyr Ser Leu Thr Ile Thr Asn Leu Glu Gln
 65              70                 75                      80

Glu Asp Ile Ala Thr Tyr Phe Cys Gln Gln Gly Ser Ala Leu Pro Tyr
                 85                 90                     95

Thr Phe Gly Gly Gly Thr Lys Leu Glu Ile Lys
                100                 105

<210> SEQ ID NO 23
<211> LENGTH: 449
<212> TYPE: PRT
<213> ORGANISM: artificial
<220> FEATURE:
<223> OTHER INFORMATION: c208F2, heavy chain, full length

<400> SEQUENCE: 23

Gln Val Gln Leu Gln Gln Ser Gly Pro Glu Leu Val Lys Pro Gly Ala
1               5                  10                 15

Ser Val Lys Met Ser Cys Lys Ala Ser Gly Tyr Thr Phe Thr Ser Tyr
                20                  25                 30

Tyr Ile Tyr Trp Val Lys Gln Arg Pro Gly Gln Gly Leu Glu Trp Leu
                35                  40                 45

Gly Trp Ile Trp Pro Gly Asp Gly Ser Thr Lys Tyr Asn Glu Lys Phe
 50                  55                 60

Lys Asp Lys Thr Thr Leu Thr Ala Asp Lys Ser Ser Asn Thr Ala Tyr
 65              70                 75                      80

Met Phe Leu Ser Ser Leu Thr Ser Glu Asp Ser Ala Val Tyr Phe Cys
                 85                 90                     95

Ala Ser Pro Met Ile Thr Pro Asn Tyr Ala Met Asp Tyr Trp Gly Gln
                100                 105                110

Gly Ala Ser Val Thr Val Ser Ser Ala Ser Thr Lys Gly Pro Ser Val
                115                 120                125

Phe Pro Leu Ala Pro Ser Ser Lys Ser Thr Ser Gly Gly Thr Ala Ala
                130                 135                140

Leu Gly Cys Leu Val Lys Asp Tyr Phe Pro Glu Pro Val Thr Val Ser
145                 150                 155                160

Trp Asn Ser Gly Ala Leu Thr Ser Gly Val His Thr Phe Pro Ala Val
                165                 170                175

Leu Gln Ser Ser Gly Leu Tyr Ser Leu Ser Ser Val Val Thr Val Pro
                180                 185                190

Ser Ser Ser Leu Gly Thr Gln Thr Tyr Ile Cys Asn Val Asn His Lys
                195                 200                205

Pro Ser Asn Thr Lys Val Asp Lys Arg Val Glu Pro Lys Ser Cys Asp
                210                 215                220

Lys Thr His Thr Cys Pro Pro Cys Pro Ala Pro Glu Leu Leu Gly Gly
225                 230                 235                240

Pro Ser Val Phe Leu Phe Pro Pro Lys Pro Lys Asp Thr Leu Met Ile
                245                 250                255

Ser Arg Thr Pro Glu Val Thr Cys Val Val Val Asp Val Ser His Glu
```

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 24
<211> LENGTH: 449
<212> TYPE: PRT
<213> ORGANISM: artificial
<220> FEATURE:
<223> OTHER INFORMATION: c212A11, heavy chain, full length

<400> SEQUENCE: 24

Gln Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Tyr Ile His Trp Val Lys Gln Arg Pro Gly Gln Gly Leu Glu Trp Ile
        35                  40                  45
Gly Trp Ile Trp Pro Gly Asp Gly Ser Thr Lys Tyr Asn Glu Lys Phe
    50                  55                  60
Lys Gly Lys Thr Thr Leu Thr Ala Asp Lys Ser Ser Ser Thr Ala Tyr
65                  70                  75                  80
Met Phe Leu Ser Ser Leu Thr Ser Glu Asp Ser Ala Val Tyr Phe Cys
                85                  90                  95
Ala Ser Pro Met Ile Thr Pro Asn Tyr Ala Met Asp Tyr Trp Gly Gln
            100                 105                 110
Gly Ala Ser Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 25
<211> LENGTH: 449
<212> TYPE: PRT
<213> ORGANISM: artificial
<220> FEATURE:
<223> OTHER INFORMATION: c214F8, heavy chain, full length

<400> SEQUENCE: 25

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
        50                  55                  60

Lys Gly Lys Thr Thr Leu Thr Ala Asp Lys Ser Ser Ser Thr Ala Tyr
65                  70                  75                  80

-continued

```
Met Phe Leu Ser Ser Leu Thr Ser Glu Asp Ser Ala Val Tyr Phe Cys
             85                  90                  95

Ala Ser Pro Met Ile Thr Pro Asn Tyr Ala Met Asp Tyr Trp Gly Gln
        100                 105                 110

Gly Ala Ser Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 26
<211> LENGTH: 449
<212> TYPE: PRT
<213> ORGANISM: artificial
<220> FEATURE:
<223> OTHER INFORMATION: c219D6, heavy chain, full length
```

-continued

<400> SEQUENCE: 26

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
            20                  25                  30

Phe Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
    50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 27
<211> LENGTH: 449
<212> TYPE: PRT
<213> ORGANISM: artificial
<220> FEATURE:
<223> OTHER INFORMATION: c213B10, heavy chain, full length

<400> SEQUENCE: 27

Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
 50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly

<210> SEQ ID NO 28
<211> LENGTH: 214
<212> TYPE: PRT
<213> ORGANISM: artificial
<220> FEATURE:
<223> OTHER INFORMATION: c208F2, light chain, full length

<400> SEQUENCE: 28

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

```
<210> SEQ ID NO 29
<211> LENGTH: 214
<212> TYPE: PRT
<213> ORGANISM: artificial
<220> FEATURE:
<223> OTHER INFORMATION: c212A11, light chain, full length

<400> SEQUENCE: 29

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: artificial
<220> FEATURE:
<223> OTHER INFORMATION: c214F8, light chain, full length

<400> SEQUENCE: 30

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95
```

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 31
<211> LENGTH: 214
<212> TYPE: PRT
<213> ORGANISM: artificial
<220> FEATURE:
<223> OTHER INFORMATION: c219D6, light chain, full length

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 32
<211> LENGTH: 214
```

<212> TYPE: PRT
<213> ORGANISM: artificial
<220> FEATURE:
<223> OTHER INFORMATION: c213B10, light chain, full length

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 120
<212> TYPE: PRT
<213> ORGANISM: artificial
<220> FEATURE:
<223> OTHER INFORMATION: hz208F2 (var.1) heavy chain, VH

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

```
Gly Thr Leu Val Thr Val Ser Ser
        115                 120

<210> SEQ ID NO 34
<211> LENGTH: 120
<212> TYPE: PRT
<213> ORGANISM: artificial
<220> FEATURE:
<223> OTHER INFORMATION: hz208F2 (var. 3), VH

<400> SEQUENCE: 34

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 35
<211> LENGTH: 107
<212> TYPE: PRT
<213> ORGANISM: artificial
<220> FEATURE:
<223> OTHER INFORMATION: hz208F2 (var. 1), VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: artificial
<220> FEATURE:
<223> OTHER INFORMATION: hz208F2 (var.3), VL

<400> SEQUENCE: 36
```

-continued

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
            85                  90                  95

Thr Phe Gly Gly Gly Thr Lys Val Glu Ile Lys
            100                 105

<210> SEQ ID NO 37
<211> LENGTH: 449
<212> TYPE: PRT
<213> ORGANISM: artificial
<220> FEATURE:
<223> OTHER INFORMATION: hz208F2 (var. 1), heavy chain, full length

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Trp Pro Gly Asp Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

-continued

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly

<210> SEQ ID NO 38
<211> LENGTH: 449
<212> TYPE: PRT
<213> ORGANISM: artificial
<220> FEATURE:
<223> OTHER INFORMATION: hz208F2 (var.3), heavy chain full length

<400> SEQUENCE: 38

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 39
<211> LENGTH: 214
<212> TYPE: PRT
<213> ORGANISM: artificial
<220> FEATURE:
<223> OTHER INFORMATION: hz208F2 (var. 1), light chain, full length

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 214
<212> TYPE: PRT
<213> ORGANISM: artificial
<220> FEATURE:
<223> OTHER INFORMATION: hz208F2 (var.3), light chain, full length

<400> SEQUENCE: 40

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 41
<211> LENGTH: 120
<212> TYPE: PRT
<213> ORGANISM: artificial
<220> FEATURE:
<223> OTHER INFORMATION: hz208F2 (var.2) heavy chain, VH
<220> FEATURE:
<221> NAME/KEY: MISC_FEATURE
<222> LOCATION: (20)..(20)
<223> OTHER INFORMATION: Met may be replaced by Val
<220> FEATURE:
<221> NAME/KEY: MISC_FEATURE
<222> LOCATION: (34)..(34)
<223> OTHER INFORMATION: Ile may be replaced by Met
<220> FEATURE:
<221> NAME/KEY: MISC_FEATURE
<222> LOCATION: (35)..(35)
<223> OTHER INFORMATION: Tyr may be replaced by His
<220> FEATURE:
<221> NAME/KEY: MISC_FEATURE
<222> LOCATION: (38)..(38)
<223> OTHER INFORMATION: Lys may be replaced by Arg
<220> FEATURE:
<221> NAME/KEY: MISC_FEATURE
<222> LOCATION: (48)..(48)
<223> OTHER INFORMATION: Leu may be replaced by Met
<220> FEATURE:
<221> NAME/KEY: MISC_FEATURE
<222> LOCATION: (50)..(50)
<223> OTHER INFORMATION: Trp may be replaced by Ile
<220> FEATURE:
<221> NAME/KEY: MISC_FEATURE
<222> LOCATION: (59)..(59)
<223> OTHER INFORMATION: Lys may be replaced by Ser
<220> FEATURE:
<221> NAME/KEY: MISC_FEATURE
<222> LOCATION: (61)..(61)
<223> OTHER INFORMATION: Asn may be replaced by Ala
<220> FEATURE:
<221> NAME/KEY: MISC_FEATURE
<222> LOCATION: (62)..(62)
<223> OTHER INFORMATION: Glu may be replaced by Gln
<220> FEATURE:
<221> NAME/KEY: MISC_FEATURE
<222> LOCATION: (70)..(70)
<223> OTHER INFORMATION: Leu may be replaced by Met
<220> FEATURE:
<221> NAME/KEY: MISC_FEATURE
<222> LOCATION: (72)..(72)
<223> OTHER INFORMATION: Ala may be replaced by Arg
<220> FEATURE:
<221> NAME/KEY: MISC_FEATURE
<222> LOCATION: (74)..(74)
<223> OTHER INFORMATION: Lys may be replaced by Thr
<220> FEATURE:
<221> NAME/KEY: MISC_FEATURE
<222> LOCATION: (76)..(76)
<223> OTHER INFORMATION: Ser may be replaced by Thr
<220> FEATURE:
<221> NAME/KEY: MISC_FEATURE
<222> LOCATION: (77)..(77)
<223> OTHER INFORMATION: Asn may be replaced by Ser
<220> FEATURE:
<221> NAME/KEY: MISC_FEATURE
<222> LOCATION: (79)..(79)
<223> OTHER INFORMATION: Ala may be replaced by Val
<220> FEATURE:
<221> NAME/KEY: MISC_FEATURE
<222> LOCATION: (82)..(82)
<223> OTHER INFORMATION: Phe may be replaced by Glu
<220> FEATURE:
<221> NAME/KEY: MISC_FEATURE
<222> LOCATION: (95)..(95)
<223> OTHER INFORMATION: Phe may be replaced by Tyr

<400> SEQUENCE: 41
```

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
            115                 120
```

<210> SEQ ID NO 42
<211> LENGTH: 107
<212> TYPE: PRT
<213> ORGANISM: artificial
<220> FEATURE:
<223> OTHER INFORMATION: hz208F2 (var. 2), light chain, VL
<220> FEATURE:
<221> NAME/KEY: MISC_FEATURE
<222> LOCATION: (22)..(22)
<223> OTHER INFORMATION: Ser may be replaced by Thr
<220> FEATURE:
<221> NAME/KEY: MISC_FEATURE
<222> LOCATION: (53)..(53)
<223> OTHER INFORMATION: Arg may be replaced by Ser
<220> FEATURE:
<221> NAME/KEY: MISC_FEATURE
<222> LOCATION: (55)..(55)
<223> OTHER INFORMATION: His may be replaced by Gln
<220> FEATURE:
<221> NAME/KEY: MISC_FEATURE
<222> LOCATION: (65)..(65)
<223> OTHER INFORMATION: Arg may be replaced by Ser
<220> FEATURE:
<221> NAME/KEY: MISC_FEATURE
<222> LOCATION: (71)..(71)
<223> OTHER INFORMATION: Tyr may be replaced by Phe
<220> FEATURE:
<221> NAME/KEY: MISC_FEATURE
<222> LOCATION: (72)..(72)
<223> OTHER INFORMATION: Ser may be replaced by Thr
<220> FEATURE:
<221> NAME/KEY: MISC_FEATURE
<222> LOCATION: (77)..(77)
<223> OTHER INFORMATION: Asn may be replaced by Ser
<220> FEATURE:
<221> NAME/KEY: MISC_FEATURE
<222> LOCATION: (87)..(87)
<223> OTHER INFORMATION: Phe may be replaced by Tyr

<400> SEQUENCE: 42

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
```

```
                    65                  70                  75                  80
Glu Asp Phe Ala Thr Tyr Phe Cys Gln Gln Gly Ser Thr Leu Pro Tyr
                            85                  90                  95

Thr Phe Gly Gly Gly Thr Lys Val Glu Ile Lys
                100                 105

<210> SEQ ID NO 43
<211> LENGTH: 329
<212> TYPE: PRT
<213> ORGANISM: artificial
<220> FEATURE:
<223> OTHER INFORMATION: Constant domain (VH) IgG1

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
```

<210> SEQ ID NO 44
<211> LENGTH: 326
<212> TYPE: PRT
<213> ORGANISM: artificial
<220> FEATURE:
<223> OTHER INFORMATION: Constant domain (VH) IgG4 (S228P)

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 45
<211> LENGTH: 107
<212> TYPE: PRT

-continued

<213> ORGANISM: artificial
<220> FEATURE:
<223> OTHER INFORMATION: Domain kappa (VL)

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 46
<211> LENGTH: 98
<212> TYPE: PRT
<213> ORGANISM: artificial
<220> FEATURE:
<223> OTHER INFORMATION: Human germline IGHV1-46*01

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 47
<211> LENGTH: 95
<212> TYPE: PRT
<213> ORGANISM: artificial
<220> FEATURE:
<223> OTHER INFORMATION: Human germline IGKV1-39*01

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 48
<211> LENGTH: 15
<212> TYPE: PRT
<213> ORGANISM: artificial
<220> FEATURE:
<223> OTHER INFORMATION: Human germline IGHJ4*01

<400> SEQUENCE: 48

Tyr Phe Asp Tyr Trp Gly Gln Gly Thr Leu Val Thr Val Ser Ser
1               5                   10                  15

<210> SEQ ID NO 49
<211> LENGTH: 12
<212> TYPE: PRT
<213> ORGANISM: artificial
<220> FEATURE:
<223> OTHER INFORMATION: Human germline IGKJ4*01

<400> SEQUENCE: 49

Leu Thr Phe Gly Gly Gly Thr Lys Val Glu Ile Lys
1               5                   10

<210> SEQ ID NO 50
<211> LENGTH: 1367
<212> TYPE: PRT
<213> ORGANISM: artificial
<220> FEATURE:
<223> OTHER INFORMATION: IGF-1R (human)

<400> SEQUENCE: 50

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr

```
            195                 200                 205
Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
610                 615                 620
```

```
Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn Phe Ile His Leu Ile Ile Ala Leu Pro Val Ala Val
            930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
            995                 1000                1005

Ser Phe Gly Met Val Tyr Glu Gly Val Ala Lys Gly Val Val Lys
    1010            1015               1020

Asp Glu Pro Glu Thr Arg Val Ala Ile Lys Thr Val Asn Glu Ala
    1025            1030               1035
```

```
Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 51
<211> LENGTH: 932
<212> TYPE: PRT
<213> ORGANISM: artificial
<220> FEATURE:
<223> OTHER INFORMATION: IGF-1R ECD (human)

<400> SEQUENCE: 51

Met Lys Ser Gly Ser Gly Gly Gly Ser Pro Thr Ser Leu Trp Gly Leu
1               5                   10                  15
```

-continued

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe

```
                435                 440                 445
Ala Phe Asn Pro Lys Leu Cys Val Ser Glu Ile Tyr Arg Met Glu Glu
450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
        755                 760                 765
Glu Glu Leu Glu Thr Glu Tyr Pro Phe Phe Glu Ser Arg Val Asp Asn
770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
        835                 840                 845
Phe Leu Lys Trp Pro Glu Pro Glu Asn Pro Asn Gly Leu Ile Leu Met
850                 855                 860
```

-continued

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn
            930

<210> SEQ ID NO 52
<211> LENGTH: 512
<212> TYPE: PRT
<213> ORGANISM: artificial
<220> FEATURE:
<223> OTHER INFORMATION: IGF-1R ECD Nterminal (human)

<400> SEQUENCE: 52

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

-continued

```
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
```

<210> SEQ ID NO 53
<211> LENGTH: 4
<212> TYPE: PRT
<213> ORGANISM: artificial
<220> FEATURE:
<223> OTHER INFORMATION: tetrapeptide (linker)

<400> SEQUENCE: 53

Gly Phe Leu Gly
1

<210> SEQ ID NO 54
<211> LENGTH: 4
<212> TYPE: PRT
<213> ORGANISM: artificial
<220> FEATURE:
<223> OTHER INFORMATION: tetrapeptide (linker)

<400> SEQUENCE: 54

Ala Leu Ala Leu
1

<210> SEQ ID NO 55
<211> LENGTH: 5
<212> TYPE: PRT
<213> ORGANISM: artificial
<220> FEATURE:
<223> OTHER INFORMATION: tetrapeptide (linker)

<400> SEQUENCE: 55

Pro Val Gly Val Val
1               5

<210> SEQ ID NO 56
<211> LENGTH: 120
<212> TYPE: PRT
<213> ORGANISM: artificial
<220> FEATURE:
<223> OTHER INFORMATION: hz208F2 heavy chain H037, VH

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 57
<211> LENGTH: 107
<212> TYPE: PRT
<213> ORGANISM: artificial
<220> FEATURE:
<223> OTHER INFORMATION: hz208F2 light chain L018, VL

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
    50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 58
<211> LENGTH: 449
<212> TYPE: PRT
<213> ORGANISM: artificial
<220> FEATURE:
<223> OTHER INFORMATION: hz208F2 heavy chain H037 full length

<400> SEQUENCE: 58

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
                35                  40                  45
Gly Trp Ile Trp Pro Gly Asp Gly Ser Thr Lys Tyr Ala Gln Lys Phe
            50                  55                  60
Gln Gly Arg Val Thr Met Thr Arg Asp Lys Ser Ser Thr Val Tyr
65                  70                  75                  80
Met Glu Leu Ser Ser Leu Arg Ser Glu Asp Thr Ala Val Tyr Phe Cys
                85                  90                  95
Ala Ser Pro Met Ile Thr Pro Asn Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
```

```
Glu Ala Leu His Asn His Tyr Thr Gln Lys Ser Leu Ser Leu Ser Pro
            435                 440                 445
Gly

<210> SEQ ID NO 59
<211> LENGTH: 214
<212> TYPE: PRT
<213> ORGANISM: artificial
<220> FEATURE:
<223> OTHER INFORMATION: hz208F2 light chain L018 full length

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 107
<212> TYPE: PRT
<213> ORGANISM: artificial
<220> FEATURE:
<223> OTHER INFORMATION: hz208F2 light chain L021, VL

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60
```

```
Arg Gly Ser Gly Thr Asp Phe Ser Leu Thr Ile Ser Ser Leu Gln Pro
 65                  70                  75                  80

Glu Asp Phe Ala Thr Tyr Phe Cys Gln Gln Gly Ser Thr Leu Pro Tyr
                 85                  90                  95

Thr Phe Gly Gly Gly Thr Lys Val Glu Ile Lys
            100                 105
```

<210> SEQ ID NO 61
<211> LENGTH: 214
<212> TYPE: PRT
<213> ORGANISM: artificial
<220> FEATURE:
<223> OTHER INFORMATION: hz208F2 light chain L021 full length

<400> SEQUENCE: 61

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Arg Gly Ser Gly Thr Asp Phe Ser Leu Thr Ile Ser Ser Leu Gln Pro
 65                  70                  75                  80

Glu Asp Phe Ala Thr Tyr Phe Cys Gln Gln Gly Ser Thr Leu Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 62
<211> LENGTH: 120
<212> TYPE: PRT
<213> ORGANISM: artificial
<220> FEATURE:
<223> OTHER INFORMATION: hz208F2 heavy chain H047, VH

<400> SEQUENCE: 62

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Ile His Trp Val Arg Gln Ala Pro Gly Gln Gly Leu Glu Trp Met
```

```
                35                  40                  45
Gly Trp Ile Trp Pro Gly Asp Gly Ser Thr Lys Tyr Ala Gln Lys Phe
         50                  55                  60

Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Tyr Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 63
<211> LENGTH: 449
<212> TYPE: PRT
<213> ORGANISM: artificial
<220> FEATURE:
<223> OTHER INFORMATION: hz208F2 heavy chain H047 full length

<400> SEQUENCE: 63

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Ile His Trp Val Arg Gln Ala Pro Gly Gln Gly Leu Glu Trp Met
         35                  40                  45

Gly Trp Ile Trp Pro Gly Asp Gly Ser Thr Lys Tyr Ala Gln Lys Phe
     50                  55                  60

Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Tyr Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 64
<211> LENGTH: 120
<212> TYPE: PRT
<213> ORGANISM: artificial
<220> FEATURE:
<223> OTHER INFORMATION: hz208F2 heavy chain H049, VH

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 65
<211> LENGTH: 449
<212> TYPE: PRT
<213> ORGANISM: artificial
<220> FEATURE:
<223> OTHER INFORMATION: hz208F2 heavy chain H049 full length

<400> SEQUENCE: 65

Gln Val Gln Leu Val Gln Ser Gly Ala Glu Val Lys Lys Pro Gly Ala
```

-continued

```
 1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
                35                  40                  45
Gly Trp Ile Trp Pro Gly Asp Gly Ser Thr Lys Tyr Ala Gln Lys Phe
                50                  55                  60
Gln Gly Arg Val Thr Met Thr Arg Asp Lys Ser Ser Thr Val Tyr
 65                 70                  75                  80
Met Glu Leu Ser Ser Leu Arg Ser Glu Asp Thr Ala Val Tyr Tyr Cys
                85                  90                  95
Ala Ser Pro Met Ile Thr Pro Asn Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
```

-continued

```
Glu Ala Leu His Asn His Tyr Thr Gln Lys Ser Leu Ser Leu Ser Pro
        435                 440                 445
Gly

<210> SEQ ID NO 66
<211> LENGTH: 120
<212> TYPE: PRT
<213> ORGANISM: artificial
<220> FEATURE:
<223> OTHER INFORMATION: hz208F2 heavy chain H051, VH

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 67
<211> LENGTH: 449
<212> TYPE: PRT
<213> ORGANISM: artificial
<220> FEATURE:
<223> OTHER INFORMATION: hz208F2 heavy chain H051 full length

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly
```

<210> SEQ ID NO 68
<211> LENGTH: 120
<212> TYPE: PRT
<213> ORGANISM: artificial
<220> FEATURE:
<223> OTHER INFORMATION: hz208F2 heavy chain H052, VH

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60
```

```
Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 69
<211> LENGTH: 449
<212> TYPE: PRT
<213> ORGANISM: artificial
<220> FEATURE:
<223> OTHER INFORMATION: hz208F2 heavy chain H052 full length

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 70
<211> LENGTH: 120
<212> TYPE: PRT
<213> ORGANISM: artificial
<220> FEATURE:
<223> OTHER INFORMATION: hz208F2 heavy chain H057, VH

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 71
<211> LENGTH: 449
<212> TYPE: PRT
<213> ORGANISM: artificial
<220> FEATURE:
<223> OTHER INFORMATION: hz208F2 heavy chain H057 full length

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

Tyr Ile His Trp Val Arg Gln Ala Pro Gly Gln Gly Leu Glu Trp Met
            35                  40                  45
Gly Trp Ile Trp Pro Gly Asp Gly Ser Thr Lys Tyr Ala Gln Lys Phe
 50                  55                  60
Gln Gly Arg Val Thr Met Thr Arg Asp Lys Ser Thr Asn Thr Val Tyr
 65                  70                  75                  80
Met Glu Leu Ser Ser Leu Arg Ser Glu Asp Thr Ala Val Tyr Tyr Cys
                 85                  90                  95
Ala Ser Pro Met Ile Thr Pro Asn Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly

<210> SEQ ID NO 72
<211> LENGTH: 120
<212> TYPE: PRT
<213> ORGANISM: artificial
<220> FEATURE:
<223> OTHER INFORMATION: hz208F2 heavy chain H068, VH

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 73
<211> LENGTH: 449
<212> TYPE: PRT
<213> ORGANISM: artificial
<220> FEATURE:
<223> OTHER INFORMATION: hz208F2 heavy chain H068 full length

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
                180                 185                 190
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 74
<211> LENGTH: 120
<212> TYPE: PRT
<213> ORGANISM: artificial
<220> FEATURE:
<223> OTHER INFORMATION: hz208F2 heavy chain H070, VH

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

-continued

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 75
<211> LENGTH: 449
<212> TYPE: PRT
<213> ORGANISM: artificial
<220> FEATURE:
<223> OTHER INFORMATION: hz208F2 heavy chain H070 full length

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 76
<211> LENGTH: 120
<212> TYPE: PRT
<213> ORGANISM: artificial
<220> FEATURE:
<223> OTHER INFORMATION: hz208F2 heavy chain H071, VH

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
            85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 77
<211> LENGTH: 449
<212> TYPE: PRT
<213> ORGANISM: artificial
<220> FEATURE:
<223> OTHER INFORMATION: hz208F2 heavy chain H071 full length

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60
```

-continued

```
Gln Gly Arg Val Thr Met Thr Arg Asp Thr Ser Thr Asn Thr Val Tyr
 65                  70                  75                  80

Met Glu Leu Ser Ser Leu Arg Ser Glu Asp Thr Ala Val Tyr Tyr Cys
             85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 78
<211> LENGTH: 120
<212> TYPE: PRT
```

<213> ORGANISM: artificial
<220> FEATURE:
<223> OTHER INFORMATION: hz208F2 heavy chain H076, VH

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 79
<211> LENGTH: 449
<212> TYPE: PRT
<213> ORGANISM: artificial
<220> FEATURE:
<223> OTHER INFORMATION: hz208F2 heavy chain H076 full length

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 80
<211> LENGTH: 120
<212> TYPE: PRT
<213> ORGANISM: artificial
<220> FEATURE:
<223> OTHER INFORMATION: hz208F2 heavy chain H077, VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
            85                  90                  95

Ala Ser Pro Met Ile Thr Pro Asn Tyr Ala Met Asp Tyr Trp Gly Gln
        100                 105                 110

Gly Thr Leu Val Thr Val Ser Ser

-continued

```
            115                 120

<210> SEQ ID NO 81
<211> LENGTH: 449
<212> TYPE: PRT
<213> ORGANISM: artificial
<220> FEATURE:
<223> OTHER INFORMATION: hz208F2 heavy chain H077 full length

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

-continued

```
               355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly
```